US007060808B1

(12) United States Patent
Goldstein et al.

(10) Patent No.: US 7,060,808 B1
(45) Date of Patent: Jun. 13, 2006

(54) HUMANIZED ANTI-EGF RECEPTOR MONOCLONAL ANTIBODY

(75) Inventors: Neil I. Goldstein, Maplewood, NJ (US); Nicholas A. Giorgio, New York, NY (US); Steven Tarran Jones, Radlett (GB); Jose William Saldanha, Enfield (GB)

(73) Assignee: ImClone Systems Incorporated, New York, NY (US)

( * ) Notice: Subject to any disclaimer, the term of this patent is extended or adjusted under 35 U.S.C. 154(b) by 0 days.

(21) Appl. No.: 08/973,065

(22) PCT Filed: Jun. 7, 1996

(86) PCT No.: PCT/US96/09847

§ 371 (c)(1),
(2), (4) Date: Mar. 19, 1998

(87) PCT Pub. No.: WO96/40210

PCT Pub. Date: Dec. 19, 1996

Related U.S. Application Data

(63) Continuation-in-part of application No. 08/573,289, filed on Dec. 15, 1995, now abandoned, which is a continuation-in-part of application No. 08/482,982, filed on Jun. 7, 1995, now abandoned.

(51) Int. Cl.
*C07H 21/04* (2006.01)
(52) U.S. Cl. .............. 536/23.1; 536/23.53; 530/387.3; 530/388.85; 435/69.1; 435/69.6; 435/325; 435/252.3
(58) Field of Classification Search .............. 435/69.1, 435/325, 252.3
See application file for complete search history.

(56) References Cited

U.S. PATENT DOCUMENTS

| 4,943,533 | A | * | 7/1990 | Mendelsohn et al. |
| 5,225,539 | A | | 7/1993 | Winter |
| 5,859,205 | A | * | 1/1999 | Adair et al. |
| 6,407,213 | B1 | | 6/2002 | Carter et al. |
| 6,632,927 | B1 | | 10/2003 | Adair et al. |
| 6,639,055 | B1 | | 10/2003 | Carter et al. |

FOREIGN PATENT DOCUMENTS

| EP | 0 460 167 | | 10/1995 |
| WO | WO 91/0996 | * | 7/1991 |
| WO | WO A 92/22653 | | 12/1992 |

OTHER PUBLICATIONS

Vinkemeier, J. Cell Science 106:319, 1993.*
Paul, Fundamental Immunology 242, Chapter 8, p 242, 1993.*
Panka et al., Proc. Natl. Acad. Sci. 85:3080-3084, 1988.*
Amit et al., Science 233:747-53, 1986.*
Morrison et al., Ann. Rev. Immnol. 2:239-56, 1984.*
Lyons et al., Protein engineering 3:703-708, 1990.*
Walter., Proc. Natl. Acad. Sci. USA 77:5197:5200, 1980.*
Axelsson, Acta Chemica Scandinavica B 39:69-77, 1985.*
Paulus et al., Behring inst Mitt No 78:118-132, 1985.*
Riechmann et al., Nature 332:323-327, 1988.*
Rudikoff et al., Proc. Natl. Acad. Sci. USA 79:1979-83, 1982.*
Kettleborough, et al., PCT Application WO95/25167 Sep. 21, 1995.
Hurwitz, et al., Int. J. Cancer 37, 739-745 (1986).
Scher, et al. Clinical Cancer Research 1, 545-550 (May 1995).
Baselga, et al., Journal of the National Cancer Institute 85, 1327-1333 (1993).
Beerli, et al., Biochemical and Biophysical Research Communications 204, 666-672 (1994).
Divgi, et al., Journal of The National Cancer Institute 83, 97-104 (1991).
Naramura, et al., Cancer Immunology Immunotherapy 37, 343-349 (1993).
Naramura, et al., Immunology Letters 39, 91-99 (1994).
Schechter, et al., Int. J. Cancer 48, 167-172 (1991).
Wels, et al., International Journal of Cancer 60, 137-144 (1995).
J. Baselga et al., "Antitumor Effects of Doxorubicin in Combination With Anti-epidermal Growth Factor Receptor Monoclonal Antibodies", Journal of the National Cancer Institute, vol. 85, No. 16, pp. 1327-1333, Aug. 18, 1993.
Carter et al., "Humanization of an anti-p185HER2 antibody for human cancer therapy" Proc. Natl. Acad. Sci. USA, vol. 89, pp. 4285-4289, May 1992.
C. Chothia et al., "Conformations of immunoglobulin hypervariable regions" Nature, vol. 342, pp. 877-883, Dec. 1989.
Graziani et al., "Regulation of Protein Kinases Activity by Quercetin in Ehrlich Ascites Tumor Cells" Biochimica et Biophysica Acta, vol. 714, pp. 415-421, 1981.
G. James et al., "Benzidiazepine Peptidimimetics: Potent Inhibitors of Ras Farnesylation in Animal Cells" Science, vol. 260, pp. 1937-1942, Jun. 25, 1993.

(Continued)

*Primary Examiner*—Larry R. Helms
*Assistant Examiner*—Parithosh K. Tungaturthi
(74) *Attorney, Agent, or Firm*—Kenyon & Kenyon

(57) ABSTRACT

A nucleic acid is provided which encodes a humanized antibody or fragment thereof, which encodes a protein which binds to human EGF-receptor. Monoclonal antibody 225 is the complementary determining region (CDR) donor.

24 Claims, 23 Drawing Sheets

OTHER PUBLICATIONS

K. Sato et al., "Reshaping a Human Antibody to Inhibit the Interleukin 6-dependent Tumor Cell Growth" Cancer Research, vol. 53, pp. 851-856, Feb. 15, 1993.

R. Taub et al., "A Monoclonal Antibody against the Platelet Fibrinogen Receptor Contains a Sequence That Mimics a Receptor Recognition Domain in Fibrinogen" Journal of Biological Chemistry, vol. 264, No. 1, Jan. 5, 1989.

Yang et al., "Doxorubicin conjugated with a monoclonal antibody directed to a human melanoma-associated proteoglycan suppresses the growth of established tumor xenografts in nude mice" Proc. Natl. Acad. Sci. vol. 85, pp. 1189-1193, Feb. 1988.

* cited by examiner

Figure 11: Schematic representation of the pKN100 mammalian expression vector used for the expression of the kapp light chains of the chimeric C225 and reshaped human H225 antibody.
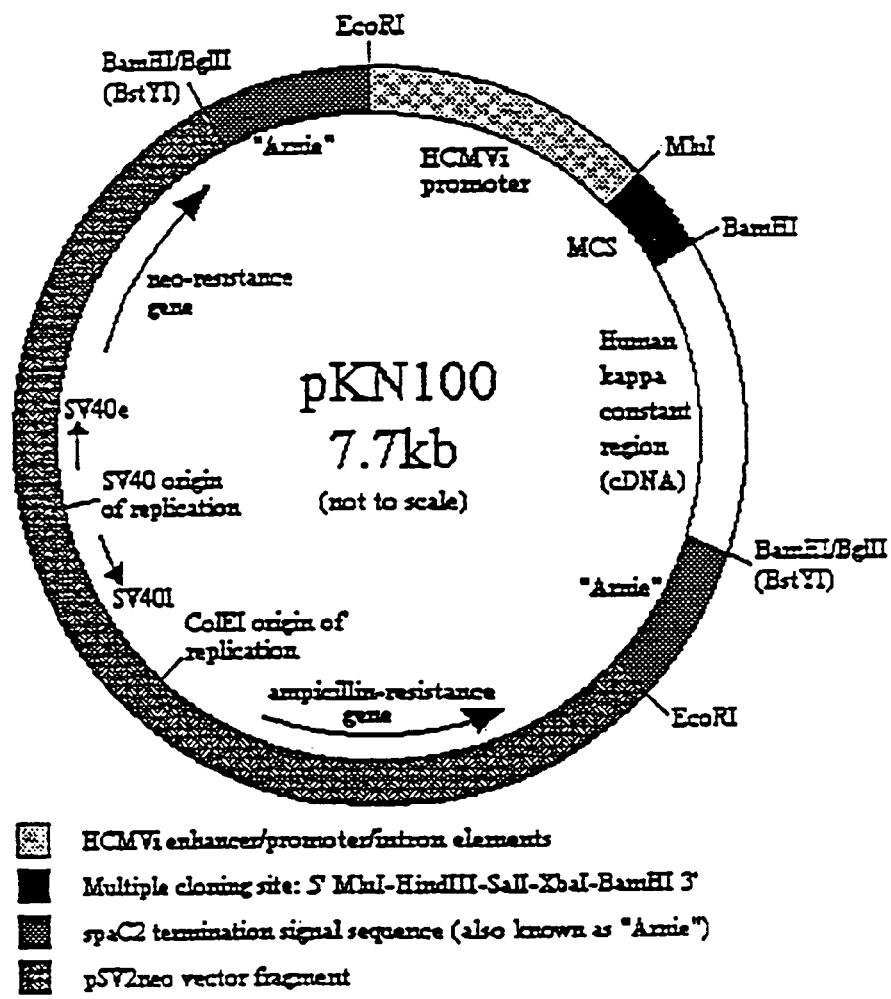

Figure 12: Schematic representation of the pG1D105 mammalian expression vector used for the expression of the heavy chains of the chimeric C225 and reshaped human H225 antibody.
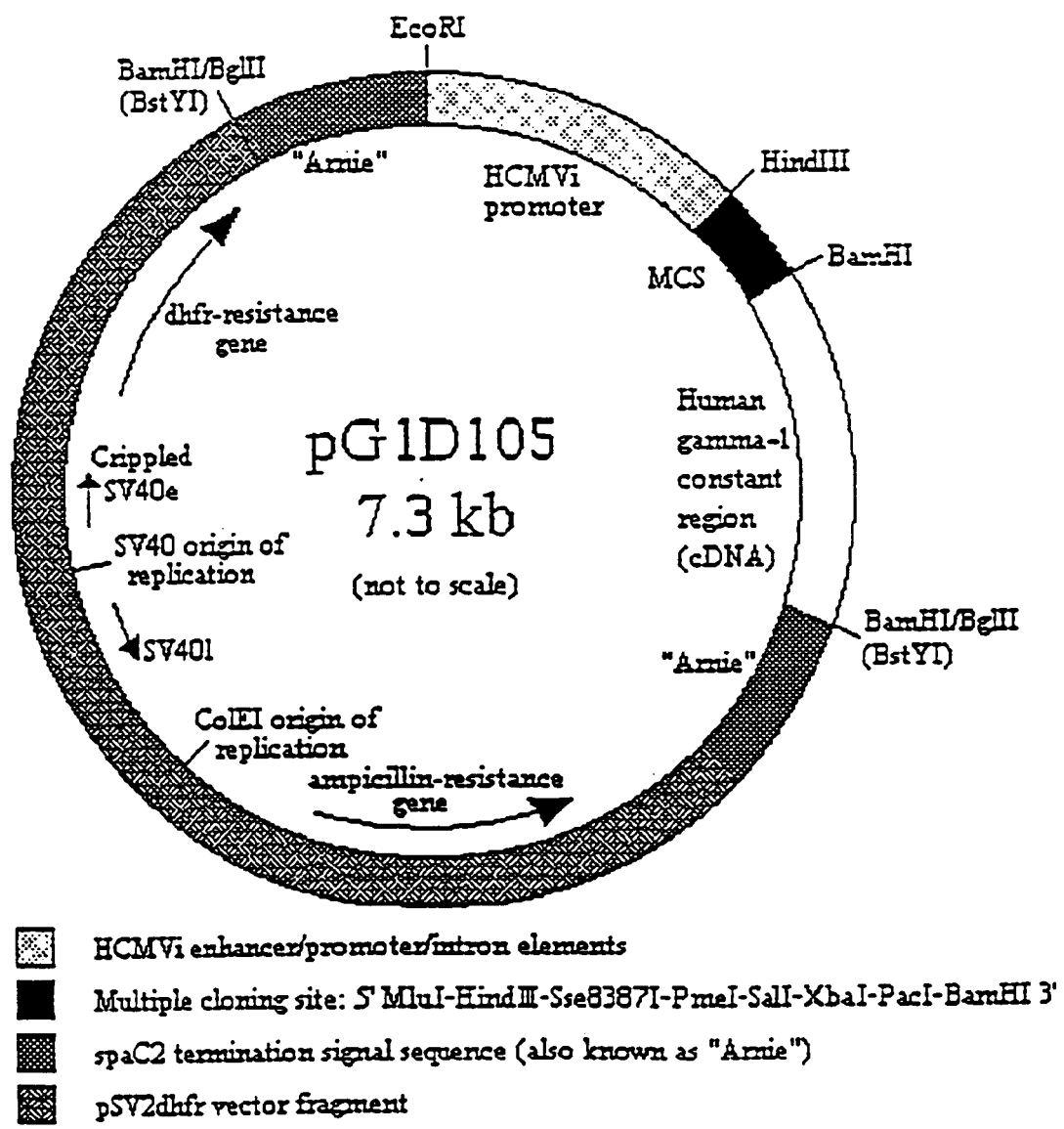

Figure 13: DNA and peptide sequences of the kappa light chain variable region of the M225 antibody. The PCR-clones from which this information was obtained were amplified using the degenerate primer MKV4 (7).

```
MKV4        atgagggcccctgctcagtttcttggcttcttg
            a          a  t     aa atgagggcccctgctcagtttcttggcttcttgcttttctggattccagcctccagaagt
  1         ---------+---------+---------+---------+---------+---------+  60
            tactcccggggacgagtcaaagaaccgaagaacgaaaagacctaaggtcggaggtcttca

M  R  A  P  A  Q  F  L  G  F  L  L  F  W  I  P  A  S  R  S gacatcttgctgactcagtctccagtcatcctgtctgtgagtccaggagaaagagtcagt
 61         ---------+---------+---------+---------+---------+---------+ 120
            ctgtagaacgactgagtcagaggtcagtaggacagacactcaggtcctctttctcagtca

D  I  L  L  T  Q  S  P  V  I  L  S  V  S  P  G  E  R  V  S ttctcctgcagggccagtcagagtattggcacaaacatacactggtatcagcaaagaaca
121         ---------+---------+---------+---------+---------+---------+ 180
            aagaggacgtcccggtcagtctcataaccgtgtttgtatgtgaccatagtcgtttcttgt

F  S  C  R  A  S  Q  S  I  G  T  N  I  H  W  Y  Q  Q  R  T aatggttctccaaggcttctcataaagtatgcttctgagtctatctctgggatcccttcc
181         ---------+---------+---------+---------+---------+---------+ 240
            ttaccaagaggttccgaagagtatttcatacgaagactcagatagagaccctagggaagg

N  G  S  P  R  L  L  I  K  Y  A  S  E  S  I  S  G  I  P  S aggtttagtggcagtggatcagggacagatttactcttagcatcaacagtgtggagtct
241         ---------+---------+---------+---------+---------+---------+ 300
            tccaaatcaccgtcacctagtccctgtctaaaatgagaatcgtagttgtcacacctcaga

R  F  S  G  S  G  S  G  T  D  F  T  L  S  I  N  S  V  E  S gaagatattgcagattattactgtcaacaaaataataactggccaaccacgttcggtgct
301         ---------+---------+---------+---------+---------+---------+ 360
            cttctataacgtctaataatgacagttgttttattattgaccggttggtgcaagccacga

E  D  I  A  D  Y  Y  C  Q  Q  N  N  N  W  P  T  T  F  G  A gggaccaagctggagctgaaa
361         ---------+---------+- 381
            ccctggttcgacctcgacttt

G  T  K  L  E  L  K
```

Figure 14: DNA and peptide sequences of the heavy chain variable region of the M225 antibody. The PCR-clones from which this information was obtained were amplified using the degenerate primer MHV6 (7).

```
MHV6        atggctgtcttggcgctgctcttctgc
             c a g    a atggctgtcttggcgctgctcttctgcctggtgacattcccaagctgtgtcctatcccag
  1     ----------+---------+---------+---------+---------+---------+ 60
        taccgacagaaccgcgacgagaagacggaccactgtaagggttcgacacaggatagggtc

M  A  V  L  A  L  L  F  C  L  V  T  F  P  S  C  V  L  S  Q gtgcagctgaagcagtcaggacctggcctagtgcagccctcacagagcctgtccatcacc
 61     ----------+---------+---------+---------+---------+---------+ 120
        gacgtcgacttcgtcagtcctggaccggatcacgtcgggagtgtctcggacaggtagtgg

V  Q  L  K  Q  S  G  P  G  L  V  Q  P  S  Q  S  L  S  I  T tgcacagtctctggtttctcattaactaactatggtgtacactgggttcgccagtctcca
121     ----------+---------+---------+---------+---------+---------+ 180
        acgtgtcagagaccaaagagtaattgattgataccacatgtgacccaagcggtcagaggt

C  T  V  S  G  F  S  L  T  N  Y  G  V  H  W  V  R  Q  S  P ggaaagggtctggagtggctgggagtgatatggagtggtggaaacacagactataataca
181     ----------+---------+---------+---------+---------+---------+ 240
        cctttcccagacctcaccgaccctcactatacctcaccacctttgtgtctgatattatgt

G  K  G  L  E  W  L  G  V  I  W  S  G  G  N  T  D  Y  N  T cctttcacatccagactgagcatcaacaaggacaattccaagagccaagttttctttaaa
241     ----------+---------+---------+---------+---------+---------+ 300
        ggaaagtgtaggtctgactcgtagttgttcctgttaaggttctcggttcaaaagaaattt

P  F  T  S  R  L  S  I  N  K  D  N  S  K  S  Q  V  F  F  K atgaacagtctgcaatctaatgacacagccatatattactgtgccagagccctcacctac
301     ----------+---------+---------+---------+---------+---------+ 360
        tacttgtcagacgttagattactgtgtcggtatataatgacacggtctcgggagtggatg

M  N  S  L  Q  S  N  D  T  A  I  Y  Y  C  A  R  A  L  T  Y tatgattacgagtttgcttactggggccaagggactctggtcactgtctctgca
361     ----------+---------+---------+---------+---------+----- 414
        atactaatgctcaaacgaatgacccggttccctgagaccagtgacagagacgt

Y  D  Y  E  F  A  Y  W  G  Q  G  T  L  V  T  V  S  A
```

Figure 15: DNA and peptide sequences of the kappa light chain variable region of the C225 antibody.

```
    aagcttgccgccaccatgagggcccctgctcagtttcttggcttcttgcttttctggatt
1   ---------+---------+---------+---------+---------+---------+  60
    ttcgaacggcggtggtactcccggggacgagtcaaagaaccgaagaacgaaaagacctaa

M   R   A   P   A   Q   F   L   G   F   L   L   F   W   I ccagcctccagaagtgacatcttgctgactcagtctccagtcatcctgtctgtgagtcca
61  ---------+---------+---------+---------+---------+---------+ 120
    ggtcggaggtcttcactgtagaacgactgagtcagaggtcagtaggacagacactcaggt

P   A   S   R   S   D   I   L   L   T   Q   S   P   V   I   L   S   V   S   P ggagaaagagtcagtttctcctgcagggccagtcagagtattggcacaaacatacactgg
121 ---------+---------+---------+---------+---------+---------+ 180
    cctctttctcagtcaaagaggacgtcccggtcagtctcataaccgtgtttgtatgtgacc

G   E   R   V   S   F   S   C   R   A   S   Q   S   I   G   T   N   I   H   W tatcagcaaagaacaaatggttctccaaggcttctcataaagtatgcttctgagtctatc
181 ---------+---------+---------+---------+---------+---------+ 240
    atagtcgtttcttgtttaccaagaggttccgaagagtatttcatacgaagactcagatag

Y   Q   Q   R   T   N   G   S   P   R   L   L   I   K   Y   A   S   E   S   I tctgggatcccttccaggtttagtggcagtggatcagggacagatttactcttagcatc
241 ---------+---------+---------+---------+---------+---------+ 300
    agaccctagggaaggtccaaatcaccgtcacctagtccctgtctaaaatgagaatcgtag

S   G   I   P   S   R   F   S   G   S   G   S   G   T   D   F   T   L   S   I aacagtgtggagtctgaagatattgcagattattactgtcaacaaaataataactggcca
301 ---------+---------+---------+---------+---------+---------+ 360
    ttgtcacacctcagacttctataacgtctaataatgacagttgttttattattgaccggt

N   S   V   E   S   E   D   I   A   D   Y   Y   C   Q   Q   N   N   N   W   P accacgttcggtgctgggaccaagctggagctgaaacgtgagtggatccttctaga
361 ---------+---------+---------+---------+---------+------  416
    tggtgcaagccacgaccctggttcgacctcgactttgcactcacctaggaagatct

T   T   F   G   A   G   T   K   L   E   L   K
```

Figure 16: DNA and peptide sequences of the heavy chain variable region of the C225 antibody.

```
       aagcttgccgccaccatggctgtcttggggctgctcttctgcctggtgacattcccaagc
  1    ---------+---------+---------+---------+---------+---------+  60
       ttcgaacggcggtggtaccgacagaaccccgacgagaagacggaccactgtaagggttcg

M  A  V  L  G  L  L  F  C  L  V  T  F  P  S tgtgtcctatcccaggtgcagctgaagcagtcaggacctggcctagtgcagccctcacag
 61    ---------+---------+---------+---------+---------+---------+ 120
       acacaggatagggtccacgtcgacttcgtcagtcctggaccggatcacgtcgggagtgtc

C  V  L  S  Q  V  Q  L  K  Q  S  G  P  G  L  V  Q  P  S  Q agcctgtccatcacctgcacagtctctggtttctcattaactaactatggtgtacactgg
121    ---------+---------+---------+---------+---------+---------+ 180
       tcggacaggtagtggacgtgtcagagaccaaagagtaattgattgataccacatgtgacc

S  L  S  I  T  C  T  V  S  G  F  S  L  T  N  Y  G  V  H  W gttcgccagtctccaggaaagggtctggagtggctgggagtgatatggagtggtggaaac
181    ---------+---------+---------+---------+---------+---------+ 240
       caagcggtcagaggtcctttcccagacctcaccgaccctcactatacctcaccacctttg

V  R  Q  S  P  G  K  G  L  E  W  L  G  V  I  W  S  G  G  N acagactataatacacctttcacatccagactgagcatcaacaaggacaattccaagagc
241    ---------+---------+---------+---------+---------+---------+ 300
       tgtctgatattatgtggaaagtgtaggtctgactcgtagttgttcctgttaaggttctcg

T  D  Y  N  T  P  F  T  S  R  L  S  I  N  K  D  N  S  K  S caagttttctttaaaatgaacagtctgcaatctaatgacacagccatatattactgtgcc
301    ---------+---------+---------+---------+---------+---------+ 360
       gttcaaaagaaattttacttgtcagacgttagattactgtgtcggtatataatgacacgg

Q  V  F  F  K  M  N  S  L  Q  S  N  D  T  A  I  Y  Y  C  A agagccctcacctactatgattacgagtttgcttactggggccaagggactctggtcact
361    ---------+---------+---------+---------+---------+---------+ 420
       tctcgggagtggatgatactaatgctcaaacgaatgacccggttccctgagaccagtga

R  A  L  T  Y  Y  D  Y  E  F  A  Y  W  G  Q  G  T  L  V  T gtctctgcaggtgagtggatcc
421    ---------+---------+--- 442
       cagagacgtccactcacctagg

V  S  A
```

Figure 17: DNA and peptide sequences of the kappa light chain variable region of the C225 antibody with the modified leader sequence from the kappa light chain of L7'CL antibody (28).

```
       aagcttgccgccaccatggtatccacacctgagttccttgtattttgcttttctggatt
  1    ----------+----------+----------+----------+----------+----------+ 60
       ttcgaacggcggtggtaccataggtgtggactcaaggaacataaaaacgaaaagacctaa

M  V  S  T  P  E  F  L  V  F  L  L  F  W  I ccagcctccagaggtgacatcttgctgactcagtctccagtcatcctgtctgtgagtcca
 61    ----------+----------+----------+----------+----------+----------+ 120
       ggtcggaggtctccactgtagaacgactgagtcagaggtcagtaggacagacactcaggt

P  A  S  R  G  D  I  L  L  T  Q  S  P  V  I  L  S  V  S  P ggagaaagagtcagtttctcctgcagggccagtcagagtattggcacaaacatacactgg
121    ----------+----------+----------+----------+----------+----------+ 180
       cctctttctcagtcaaagaggacgtcccggtcagtctcataaccgtgtttgtatgtgacc

G  E  R  V  S  F  S  C  R  A  S  Q  S  I  G  T  N  I  H  W tatcagcaaagaacaaatggttctccaaggcttctcataaagtatgcttctgagtctatc
181    ----------+----------+----------+----------+----------+----------+ 240
       atagtcgtttcttgtttaccaagaggttccgaagagtatttcatacgaagactcagatag

Y  Q  Q  R  T  N  G  S  P  R  L  L  I  K  Y  A  S  E  S  I tctgggatcccttccaggtttagtggcagtggatcagggacagattttactcttagcatc
241    ----------+----------+----------+----------+----------+----------+ 300
       agaccctagggaaggtccaaatcaccgtcacctagtccctgtctaaaatgagaatcgtag

S  G  I  P  S  R  F  S  G  S  G  S  G  T  D  F  T  L  S  I aacagtgtggagtctgaagatattgcagattattactgtcaacaaaataataactggcca
301    ----------+----------+----------+----------+----------+----------+ 360
       ttgtcacacctcagacttctataacgtctaataatgacagttgttttattattgaccggt

N  S  V  E  S  E  D  I  A  D  Y  Y  C  Q  Q  N  N  N  W  P accacgttcggtgctgggaccaagctggagctgaaacgtgagtggatccttctaga
361    ----------+----------+----------+----------+----------+------ 416
       tggtgcaagccacgaccctggttcgacctcgactttgcactcacctaggaagatct

T  T  F  G  A  G  T  K  L  E  L  K
```

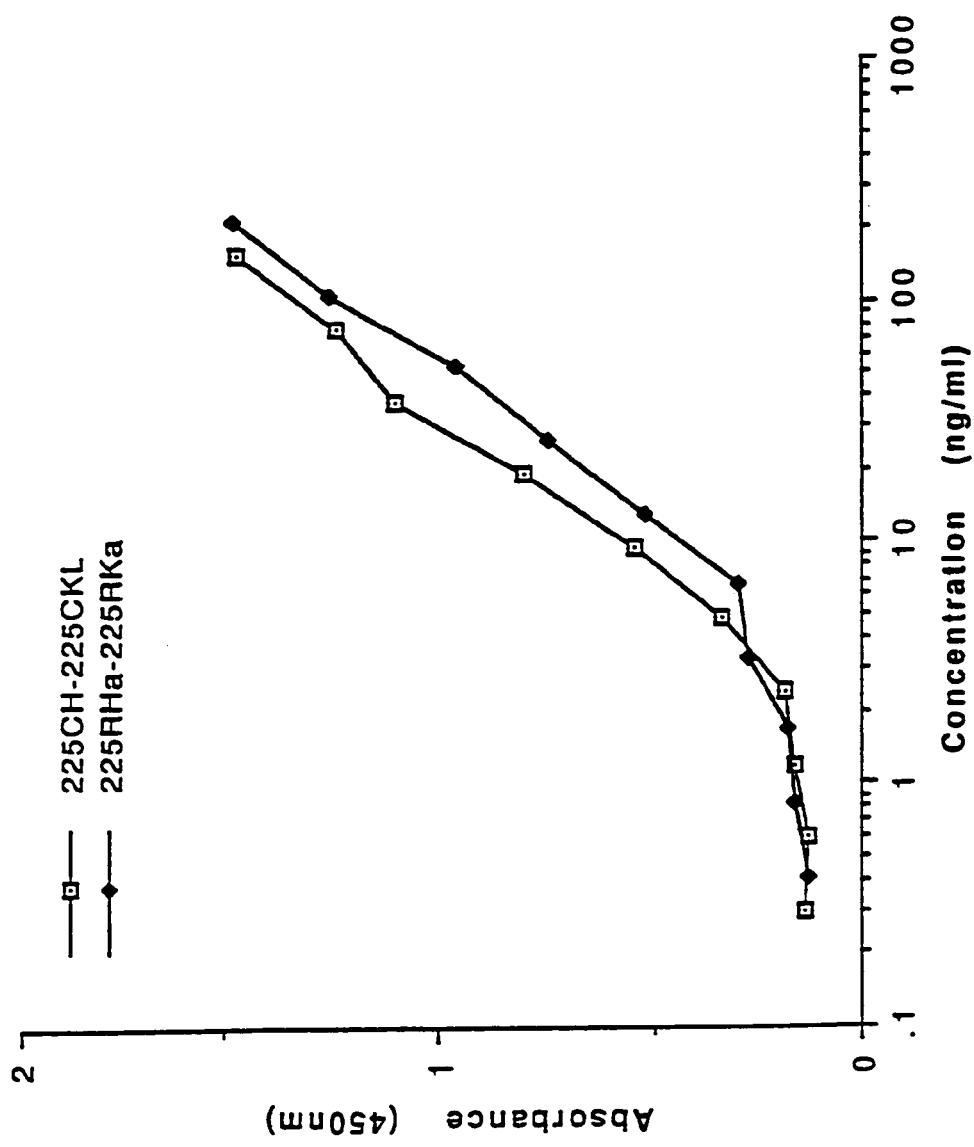
Figure 18: Typical example of the results of a cell ELISA to measure the binding affinty of chimeric C225 and reshaped human H225 (225RK$_A$/225RH$_A$) antibodies to epidermal growth factor receptor expressed on the surface of A431 cells.

Figure 19: DNA and peptide sequences of the first version (225RK$_A$) of the kappa light chain variable region of the reshaped human H225 antibody.

```
     aagcttgccgccaccatggaagccccagctcagcttctcttcctcttgcttctctggctc
  1  ------------+---------+---------+---------+---------+---------+  60
     ttcgaacggcggtggtaccttcggggtcgagtcgaagagaaggagaacgaagagaccgag

M  E  A  P  A  Q  L  L  F  L  L  L  W  L ccagataccaccggagaaatcgtactgactcagtctccagccaccctgtctttgagtcca
 61  ------------+---------+---------+---------+---------+---------+  120
     ggtctatggtggcctctttagcatgactgagtcagaggtcggtgggacagaaactcaggt

P  D  T  T  G  E  I  V  L  T  Q  S  P  A  T  L  S  L  S  P ggagaaagagccaccctctcctgcagggccagtcagagtattggcacaaacatacactgg
121  ------------+---------+---------+---------+---------+---------+  180
     cctctttctcggtgggagaggacgtcccggtcagtctcataaccgtgtttgtatgtgacc

G  E  R  A  T  L  S  C  R  A  S  Q  S  I  G  T  N  I  H  W tatcagcaaagacctggccaggctccaaggcttctcataaagtatgcttctgagtctatc
181  ------------+---------+---------+---------+---------+---------+  240
     atagtcgtttctggaccggtccgaggttccgaagagtatttcatacgaagactcagatag

Y  Q  Q  R  P  G  Q  A  P  R  L  L  I  K  Y  A  S  E  S  I tctggaatccctgccaggtttagtggcagtggatcagggacagatttttactcttaccatc
241  ------------+---------+---------+---------+---------+---------+  300
     agaccttagggacggtccaaatcaccgtcacctagtccctgtctaaaatgagaatggtag

S  G  I  P  A  R  F  S  G  S  G  S  G  T  D  F  T  L  T  I agcagtctggagcctgaagatttgcagtttattactgtcaacaaaataataactggcca
301  ------------+---------+---------+---------+---------+---------+  360
     tcgtcagacctcggacttctaaaacgtcaaataatgacagttgttttattattgaccggt

S  S  L  E  P  E  D  F  A  V  Y  Y  C  Q  Q  N  N  N  W  P accacgttcggtggagggaccaaggtggagatcaaacgtgagtggatccttctaga
361  ------------+---------+---------+---------+---------+------  416
     tggtgcaagccacctccctggttccacctctagtttgcactcacctaggaagatct

T  T  F  G  G  G  T  K  V  E  I  K
```

Figure 20: DNA and peptide sequences of the first version (225RH$_A$) of the heavy chain variable region of the reshaped human H225 antibody.

```
      aagcttgccgccaccatggagtttgggctgagctggcttttcttgtggctattttaaaa
  1   ----------+----------+----------+----------+----------+----------+  60
      ttcgaacggcggtggtacctcaaacccgactcgaccgaaaaagaacaccgataaaatttt

M  E  F  G  L  S  W  L  F  L  V  A  I  L  K ggtgtccagtgtgaggtgcagctggtcgagtctgggggaggcttggtacagcctgggggg
 61   ----------+----------+----------+----------+----------+----------+ 120
      ccacaggtcacactccacgtcgaccagctcagacccctccgaaccatgtcggacccccc

G  V  Q  C  E  V  Q  L  V  E  S  G  G  G  L  V  Q  P  G  G tccctgagactctcctgtgcagtctccggattctcattaactaactatggtgtacactgg
121   ----------+----------+----------+----------+----------+----------+ 180
      agggactctgagaggacacgtcagaggcctaagagtaattgattgataccacatgtgacc

S  L  R  L  S  C  A  V  S  G  F  S  L  T  N  Y  G  V  H  W gttcgccaggctacaggaaagggtctggagtggctgggagtgatatggagtggtggaaac
181   ----------+----------+----------+----------+----------+----------+ 240
      caagcggtccgatgtccttcccagacctcaccgaccctcactatacctcaccacctttg

V  R  Q  A  T  G  K  G  L  E  W  L  G  V  I  W  S  G  G  N acagactataatacacctttcacaagtcgactgaccatctccaaggaaaatgccaagaac
241   ----------+----------+----------+----------+----------+----------+ 300
      tgtctgatattatgtggaaagtgttcagctgactggtagaggttccttttacggttcttg

T  D  Y  N  T  P  F  T  S  R  L  T  I  S  K  E  N  A  K  N tccctgtatctgcaaatgaacagtctcagagccggggacacagccgtgtattactgtgcc
301   ----------+----------+----------+----------+----------+----------+ 360
      agggacatagacgtttacttgtcagagtctcggcccctgtgtcggcacataatgacacgg

S  L  Y  L  Q  M  N  S  L  R  A  G  D  T  A  V  Y  Y  C  A agagccctcacctactatgattacgagtttgcttactggggccaagggactatggtcact
361   ----------+----------+----------+----------+----------+----------+ 420
      tctcgggagtggatgatactaatgctcaaacgaatgacccggttccctgataccagtga

R  A  L  T  Y  Y  D  Y  E  F  A  Y  W  G  Q  G  T  M  V  T gtctcttcaggtgagtggatcc
421   ----------+----------+-- 442
      cagagaagtccactcacctagg

V  S  S
```

Figure 21: Amino acid sequences of the two versions (225RK$_A$ and 225RK$_B$) of the kappa light chain variable region of the reshaped human H225 antibody. Residues are numbered according to Kabat et al. (20). Mouse framework residues conserved in the reshaped human frameworks are highlighted in bold.

FRAMEWORK 1

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| M225/C225V$_L$ | D | I | L | L | T | Q | S | P | V | I | L | S | V | S | P | G | E | R | V | S | F | S | C |
| LS7'CL | E | I | V | L | T | Q | S | P | A | T | L | S | L | S | P | G | E | R | A | T | L | S | C |
| 225RK$_A$ | E | I | V | L | T | Q | S | P | A | T | L | S | L | S | P | G | E | R | A | T | L | S | C |
| 225RK$_B$ | | | | | | | | | | | | | | | | | | | | | | | |

CDR 1 | FR 2

| | 24 | 25 | 26 | 27 | 27A | 27B | 27C | 27D | 27E | 27F | 28 | 29 | 30 | 31 | 32 | 33 | 34 | 35 | 36 | 37 | 38 | 39 |
|---|---|---|---|---|---|---|---|---|---|---|---|---|---|---|---|---|---|---|---|---|---|---|
| M225/C225V$_L$ | R | A | S | Q | - | - | - | - | - | - | S | I | G | T | N | I | H | W | Y | Q | Q | R |
| LS7'CL | R | A | S | Q | - | - | - | - | - | - | S | V | S | S | Y | L | A | W | Y | Q | Q | R |
| 225RK$_A$ | R | A | S | Q | - | - | - | - | - | - | S | I | G | T | N | I | H | W | Y | Q | Q | R |
| 225RK$_B$ | | | | | | | | | | | | | | | | | | | | | | |

FRAMEWORK 2 | CDR 2 | FR 3

| | 40 | 41 | 42 | 43 | 44 | 45 | 46 | 47 | 48 | 49 | 50 | 51 | 52 | 53 | 54 | 55 | 56 | 57 | 58 | 59 | 60 | 61 |
|---|---|---|---|---|---|---|---|---|---|---|---|---|---|---|---|---|---|---|---|---|---|---|
| M225/C225V$_L$ | T | N | G | S | P | R | L | L | I | K | Y | A | S | E | S | I | S | G | I | P | S | R |
| LS7'CL | P | G | Q | A | P | R | L | L | I | Y | D | A | S | N | R | A | T | G | I | P | A | R |
| 225RK$_A$ | P | G | Q | A | P | R | L | L | I | K | Y | A | S | E | S | I | S | G | I | P | A | R |
| 225RK$_B$ | | | | | | | | | | | Y | | | | | | | | | | | |

FRAMEWORK 3

| | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 |
|---|---|---|---|---|---|---|---|---|---|---|---|---|---|---|---|---|---|---|---|---|---|---|---|---|
| M225/C225V$_L$ | F | S | S | S | G | S | G | T | D | F | T | L | S | I | N | S | V | E | S | E | D | I | A | D |
| LS7'CL | F | S | G | S | G | S | G | T | D | F | T | L | T | I | S | S | L | E | P | E | D | F | A | V |
| 225RK$_A$ | F | S | S | S | G | S | G | T | D | F | T | L | T | I | S | S | L | E | P | E | D | F | A | V |
| 225RK$_B$ | | | | | | | | | | | | | | | | | | | | | | | | |

FR 3 | CDR 3 | FRAMEWORK 4

| | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|
| M225/C225V$_L$ | Y | Y | C | Q | Q | N | N | N | W | P | T | T | F | G | A | G | T | K | L | E | L | K |
| LS7'CL | Y | Y | C | Q | Q | R | S | N | W | P | L | T | F | G | G | G | T | K | V | E | I | K |
| 225RK$_A$ | Y | Y | C | Q | Q | N | N | N | W | P | T | T | F | G | G | G | T | K | V | E | I | K |
| 225RK$_B$ | | | | | | | | | | | | | | | | | | | | | | |

Figure 22: Amino acid sequences of the five versions (225RH$_A$, 225RH$_B$, 225RH$_C$, 225RH$_D$, 225RH$_E$) of the heavy chain variable region of the reshaped human H225 antibody. Residues are numbered according to Kabat *et al.* (20). Mouse framework residues conserved in the reshaped human frameworks are highlighted in bold.

| | FRAMEWORK 1 | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| M225/C225V$_H$ | Q | V | Q | L | K | Q | S | G | P | G | L | V | Q | P | S | Q | S | L | S | I | T | C | T | V |
| 38P1'CL | E | V | Q | L | V | E | S | G | G | G | L | V | Q | P | G | G | S | L | R | L | S | C | A | A |
| 225RH$_A$ | E | V | Q | L | V | E | S | G | G | G | L | V | Q | P | G | G | S | L | R | L | S | C | A | V |
| 225RH$_B$ | | | | | | | | | | | | | | | | | | | | | | | | |
| 225RH$_C$ | | | | | | | | | | | | | | | | | | | | | | | | |
| 225RH$_D$ | | | | | | | | | | | | | | | | | | | | | | | | |
| 225RH$_E$ | | | | | | | | | | | | | | | | | | | | | | | | |

| | FRAMEWORK 1 | | | | | | CDR 1 | | | | | | | | FRAMEWORK 2 | | | | | | | | |
|---|---|---|---|---|---|---|---|---|---|---|---|---|---|---|---|---|---|---|---|---|---|---|---|
| | 25 | 26 | 27 | 28 | 29 | 30 | 31 | 32 | 33 | 34 | 35 | 35A | 35B | 36 | 37 | 38 | 39 | 40 | 41 | 42 | 43 | 44 |
| M225/C225V$_H$ | S | G | F | S | L | T | N | Y | G | V | H | - | - | W | V | R | Q | S | P | G | K | G |
| 38P1'CL | S | G | F | T | F | S | S | Y | D | M | H | - | - | W | V | R | Q | A | T | G | K | G |
| 225RH$_A$ | S | G | F | S | L | T | N | Y | G | V | H | - | - | W | V | R | Q | A | T | G | K | G |
| 225RH$_B$ | | | | | | | | | | | | | | | | | | P | | | | |
| 225RH$_C$ | | | | | | | | | | | | | | | | | | | | | | |
| 225RH$_D$ | | | | | | | | | | | | | | | | | | P | | | | |
| 225RH$_E$ | | | | | | | | | | | | | | | | | | | | | | |

| | FRAMEWORK 2 | | | | | | | | CDR 2 | | | | | | | | | | | | |
|---|---|---|---|---|---|---|---|---|---|---|---|---|---|---|---|---|---|---|---|---|---|
| | 45 | 46 | 47 | 48 | 49 | 50 | 51 | 52 | 52A | 52B | 52C | 53 | 54 | 55 | 56 | 57 | 58 | 59 | 60 | 61 | 62 | 63 | 64 |
| M225/C225V$_H$ | L | E | W | L | G | V | I | W | - | - | - | S | G | G | N | T | D | Y | N | T | P | F | T |
| 38P1'CL | L | E | W | V | S | A | I | G | - | - | - | T | A | G | D | T | Y | Y | P | G | S | V | K |
| 225RH$_A$ | L | E | W | L | G | V | I | W | - | - | - | S | G | G | N | T | D | Y | N | T | P | F | T |
| 225RH$_B$ | | | | | | | | | | | | | | | | | | | | | | | |
| 225RH$_C$ | | | | | | | | | | | | | | | | | | | | | | | |
| 225RH$_D$ | | | | | | | | | | | | | | | | | | | | | | | |
| 225RH$_E$ | | | | | | | | | | | | | | | | | | | | | | | |

Figure 22: continued...

|  | FRAMEWORK 3 | | | | | | | | | | | | | | | | | | | | | |
|---|---|---|---|---|---|---|---|---|---|---|---|---|---|---|---|---|---|---|---|---|---|---|
|  | 65 | 66 | 67 | 68 | 69 | 70 | 71 | 72 | 73 | 74 | 75 | 76 | 77 | 78 | 79 | 80 | 81 | 82 | 82A | 82B | 82C | 83 | 84 |
| M225/C225V$_H$ | S | R | L | S | I | N | K | D | N | S | K | S | Q | V | F | F | K | M | N | S | L | Q | S |
| 38P1'CL | G | R | F | T | I | S | R | E | N | A | K | N | S | L | Y | L | Q | M | N | S | L | R | A |
| 225RH$_A$ | S | R | L | T | I | ,S | K | E | N | A | K | N | S | L | Y | L | Q | M | N | S | L | R | A |
| 225RH$_B$ |   |   |   |   |   |   |   |   |   |   |   |   |   |   |   |   |   |   |   |   |   |   |   |
| 225RH$_C$ |   |   |   | S |   | N |   |   |   |   |   |   |   |   |   |   |   |   |   |   |   |   |   |
| 225RH$_D$ |   |   |   | S |   | N |   |   |   |   |   |   |   |   |   |   |   |   |   |   |   |   |   |
| 225RH$_E$ |   |   |   |   |   |   |   |   |   |   |   |   |   |   | V |   |   |   |   |   |   |   |   |

|  | FRAMEWORK 3 | | | | | | | | | | | | | | | CDR 3 | | | | | | | | |
|---|---|---|---|---|---|---|---|---|---|---|---|---|---|---|---|---|---|---|---|---|---|---|---|---|
|  | 85 | 86 | 87 | 88 | 89 | 90 | 91 | 92 | 93 | 94 | 95 | 96 | 97 | 98 | 99 | 100 | 100A | 100B | 100C | 100D | 100E | 100F | 100G |
| M225/C225V$_H$ | N | D | T | A | I | Y | Y | C | A | R | A | L | T | Y | Y | D | Y | E | - | - | - | - | - |
| 38P1'CL | G | D | T | A | V | Y | Y | C | A | R | S | F | S | E | T | E | D | A | - | - | - | - | - |
| 225RH$_A$ | G | D | T | A | V | Y | Y | C | A | R | A | L | T | Y | Y | D | Y | E | - | - | - | - | - |
| 225RH$_B$ |   |   |   |   |   |   |   |   |   |   |   |   |   |   |   |   |   |   |   |   |   |   |   |
| 225RH$_C$ |   |   |   |   |   |   |   |   |   |   |   |   |   |   |   |   |   |   |   |   |   |   |   |
| 225RH$_D$ |   |   |   |   |   |   |   |   |   |   |   |   |   |   |   |   |   |   |   |   |   |   |   |
| 225RH$_E$ |   |   |   |   |   |   |   |   |   |   |   |   |   |   |   |   |   |   |   |   |   |   |   |

|  | CDR 3 | | | FRAMEWORK 4 | | | | | | | | | | | |
|---|---|---|---|---|---|---|---|---|---|---|---|---|---|---|---|
|  | 100H | 100I | 100J | 100K | 101 | 102 | 103 | 104 | 105 | 106 | 107 | 108 | 109 | 110 | 111 | 112 | 113 |
| M225/C225V$_H$ | - | - | - | F | A | Y | W | G | Q | G | T | L | V | T | V | S | A |
| 38P1'CL | - | - | - | F | D | I | W | G | Q | G | T | M | V | T | V | S | S |
| 225RH$_A$ | - | - | - | F | A | Y | W | G | Q | G | T | M | V | T | V | S | S |
| 225RH$_B$ |   |   |   |   |   |   |   |   |   |   |   |   |   |   |   |   |   |
| 225RH$_C$ |   |   |   |   |   |   |   |   |   |   |   |   |   |   |   |   |   |
| 225RH$_D$ |   |   |   |   |   |   |   |   |   |   |   |   |   |   |   |   |   |
| 225RH$_E$ |   |   |   |   |   |   |   |   |   |   |   |   |   |   |   |   |   |

HUMANIZED ANTI-EGF RECEPTOR MONOCLONAL ANTIBODY

This application is a continuation-in-part of Ser. No. 08/573,289 filed Dec. 15, 1995, now abandoned, which was a continuation-in-part of Ser. No. 08/482,982 filed June 7, 1995, now abandoned, the disclosures of both of which are incorporated herein by reference.

FIELD OF THE INVENTION

The present invention is directed to antibodies and antibody fragments useful in inhibiting the growth of certain tumor cells.

BACKGROUND OF THE INVENTION

Recent research has uncovered the important role of growth factor receptor tyrosine kinases in the etiology and progression of human malignancies. These biological receptors are anchored by means of a transmembrane domain in the membranes of cells that express them. An extracellular domain binds to a growth factor. The binding of the growth factor to the extracellular domain results in a signal being transmitted to the intracellular kinase domain. The transduction of this signal contributes to the events that are responsible for the proliferation and differentiation of the cells.

Members of the epidermal growth factor (EGF) receptor family are important growth factor receptor tyrosine kinases. The first member of the EGF receptor family to be discovered was the glycoprotein having an apparent molecular weight of approximately 165 kD. This glycoprotein, which was described by Mendelsohn et al. in U.S. Pat. No. 4,943,533, is known as the EGF receptor (EGFR).

The binding of an EGFR ligand to the EGF receptor leads to cell growth. EGF and transforming growth factor alpha (TGF-alpha) are two known ligands of EGFR.

Many receptor tyrosine kinases are found in unusually high numbers on human tumors. For example, many tumors of epithelial origin express increased levels of EGF receptor on their cell membranes. Examples of tumors that express EGF receptors include glioblastomas, as well as cancers of the lung, breast, head and neck, and bladder. The amplification and/or overexpression of the EGF receptors on the membranes of tumor cells is associated with a poor prognosis.

Antibodies, especially monoclonal antibodies, raised against tumor antigens have been investigated as potential anti-tumor agents. Such antibodies may inhibit the growth of tumors through a number of mechanisms. For example, antibodies may inhibit the growth of tumors immunologically through antibody-dependent cellular cytotoxicity (ADCC) or complement-dependent cytotoxicity (CDC).

Alternatively, antibodies may compete with growth factors in binding to their receptors. Such competition inhibits the growth of tumors that express the receptor.

In another approach, toxins are conjugated to antibodies raised against tumor antigens. The antibody portion directs the conjugate to the tumor, which is killed by the toxin portion.

For example, U.S. Pat. No. 4,943,533 describes a murine monoclonal antibody called 225 that binds to the EGF receptor. The patent is assigned to the University of California and licensed exclusively to ImClone Systems Incorporated. The 225 antibody is able to inhibit the growth of cultured EGFR-expressing tumor lines as well as the growth of these tumors in vivo when grown as xenografts in nude mice. See Masui et al., Cancer Res. 44, 5592-5598 (1986). More recently, a treatment regimen combining 225 plus doxorubicin or cis-platin exhibited therapeutic synergy against several well established human xenograft models in mice. Basalga et al., J. Natl. Cancer Inst. 85, 1327-1333 (1993).

A disadvantage of using murine monoclonal antibodies in human therapy is the possibility of a human anti-mouse antibody (HAMA) response due to the presence of mouse Ig sequences. This disadvantage can be minimized by replacing the entire constant region of a murine (or other non-human mammalian) antibody with that of a human constant region. Replacement of the constant regions of a murine antibody with human sequences is usually referred to as chimerization.

The chimerization process can be made more effective by also replacing the variable regions—other than the hypervariable regions or the complementarity-determining regions (CDRs), of a murine antibody with the corresponding human sequences. The variable regions other than the CDRs are also known as the variable framework regions (FRs).

The replacement of the constant regions and non-CDR variable regions with human sequences is usually referred to as humanization. The humanized antibody is less immunogenic (i.e. elicits less of a HAMA response) as more murine sequences are replaced by human sequences. Unfortunately, both the cost and effort increase as more regions of a murine antibodies are replaced by human sequences.

Another approach to reducing the immunogenicity of antibodies is the use of antibody fragments. For example, an article by Aboud-Pirak et al., Journal of the National Cancer Institute 80, 1605-1611 (1988), compares the anti-tumor effect of an anti-EGF receptor antibody called 108.4 with fragments of the antibody. The tumor model was based on KB cells as xenografts in nude mice. KB cells are derived from human oral epidermoid carcinomas, and express elevated levels of EGF receptors.

Aboud-Pirak et al. found that both the antibody and the bivalent $F(ab')_2$ fragment retarded tumor growth in vivo, although the $F(ab')_2$ fragment was less efficient. The monovalent Fab fragment of the antibody, whose ability to bind the cell-associated receptor was conserved, did not, however, retard tumor growth.

There is, therefore, a continuing need for improved anti-tumor agents that can be efficiently and inexpensively produced, have little or no immunogenicity in humans, are capable of binding to receptors that are expressed in high numbers on tumor cells, and are capable of blocking the binding of such growth factors to such receptors. An object of the present invention is the discovery of such new anti-tumor agents that combine the advantageous features of monoclonal antibodies, antibody fragments and single chain antibodies.

SUMMARY OF THE INVENTION

These and other objects, as will be apparent to those having ordinary skill in the art, have been met by providing a polypeptide lacking the constant region and the variable light chain of an antibody, the polypeptide comprising the amino acid sequence N Y G V H(SEQ ID NO: 1), G V I W S G G N T D Y N T P F T S R (SEQ ID NO: 2), or V I W S G G N T D Y N T P F T S (SEQ ID NO: 3). The polypeptide may be conjugated to an effector molecule, such as a molecule that inhibits tumor growth. The invention further is directed to DNA encoding such polypeptides.

The includes also includes polypeptides consisting of the amino acid sequence N Y G V H, (SEQ ID NO: 1), G V I W S G G N T D Y N T P F T S R (SEQ ID NO: 2) OR V I W S G G N T D Y N T P F T S(SEQ ID NO 3). The invention also includes a molecule having the constant region of a human antibody and the variable region of monoclonal antibody 225 conjugated to a cytoxic agent such as doxorubicin, taxol, or cis-diamminedichloroplatinum (cisplatin). The invention further includes a method for significantly inhibiting the growth of tumor cells in a human comprising administering to the human an effective amount of a polypeptide lacking the constant region of the variable light chin of an antibody, the polypeptide comprising the amino acid sequence N Y G V H (SEQ ID NO: 1), G V I W S G G N T D Y N T P F T S R (SEQ ID NO: 2), or V I W S G G N T D Y N T P F T S (SEQ ID NO: 3). Another aspect of the invention is a method for significantly inhibiting the growth of tumor cells in a human comprising administering to the human an effective amount of a polypeptide consisting of the amino acid sequence N Y G V H (SEQ ID NO: 1), G V I W S G G N T D T S R (SEQ ID NO: 2), or V I W S G G N T D Y N T P F T S (SEQ ID NO: 3). The invention further includes a method for significantly inhibiting the growth of tumor cells that express the EGF receptor in a human. The method comprises administering to the human an effective amount of a molecule having the constant region of a human antibody and the variable region of monoclonal antibody 225, both in the prescence of and, in particular, in the absence of, cytotoxic molecules, such as chemotherapeutic agents.

DESCRIPTION OF FIGURES

FIG. 11. Schematic representation of the pKN100 mammalian expression vector used for the expression of the kapp light chains of the chimeric C225 and reshaped human H225 antibody.

FIG. 12. Schematic representation of the pG1D105 mammalian expression vector used for the expression of the heavy chains of the chimeric C225 and reshaped human H225 antibody.

FIG. 13. DNA (SEQ ID NOS: 4 and 103) and peptide (SEQ ID NO: 5) sequences of the kappa light chain variable region of the M225 antibody. The PCR-clones from which this information was obtained were amplified using the degenerate primer MKV4 (SEQ ID NO: 6)(7).

FIG. 14. DNA (SEQ ID NOS: 7 and 104) and peptide (SEQ ID NO: 8) sequences of the heavy chain variable region of the M225 antibody. The PCR-clones from which this information was obtained were amplified using the degenerate primer MHV6 (SEQ ID NO: 9)(7).

FIG. 15. DNA (SEQ ID NOS: 10 and 105) and peptide (SEQ ID NO: 11) sequences of the kappa light chain variable region of the C225 antibody.

FIG. 16. DNA (SEQ ID NOS: 12 and 106) and peptide (SEQ ID NO: 13) sequences of the heavy chain variable region of the C225 antibody.

FIG. 17. DNA (SEQ ID NOS: 14 and 107) and peptide (SEQ ID NO: 15) sequences of the kappa light chain variable region of the C225 antibody with the modified leader sequence from the kappa light chain of L7'CL antibody (28).

FIG. 18. Typical example of the results of a cell ELISA to measure the binding affinty of chimeric C225 and reshaped human H225 (225RK$_A$/225RH$_A$) antibodies to epidermal growth factor receptor expressed on the surface of A431 cells.

FIG. 19. DNA (SEQ ID NOS: 16 and 108) peptide (SEQ ID NO: 17) sequences of the first version (225RK$_A$) of the kappa light chain variable region of the reshaped human H225 antibody.

FIG. 20. DNA (SEQ ID NOS: 18 and 109) and peptide (SEQ ID NO: 19) sequences of the first version (225RH$_A$) of the heavy chain variable region of the reshaped human H225 antibody.

FIG. 21. Amino acid sequences of the two versions (225RK$_A$ and 225RK$_B$) of the kappa light chain variable region of the reshaped human H225 antibody (SEQ ID NO: 20), (SEQ ID NO: 21), (SEQ ID NO: 22), (SEQ ID NO: 23). Residues are numbered according to Kabat et al. (20). Mouse framework residues conserved in the reshaped human frameworks are highlighted in bold.

FIG. 22. Amino acid sequences of the five versions (225RH$_A$, 225RH$_B$, 225RH$_C$, 225RH$_D$, 225RH$_E$) of the heavy chain variable region of the reshaped human H225 antibody (SEQ ID NO: 24), (SEQ ID NO: 25), (SEQ ID NO: 26), (SEQ ID NO: 27), (SEQ ID NO: 28), (SEQ ID NO: 29), (SEQ ID NO: 30). Residues are numbered according to Kabat et al. (20). Mouse framework residues conserved in the reshaped human frameworks are highlighted in bold.

DETAILED DESCRIPTION OF THE INVENTION

Figure 1:
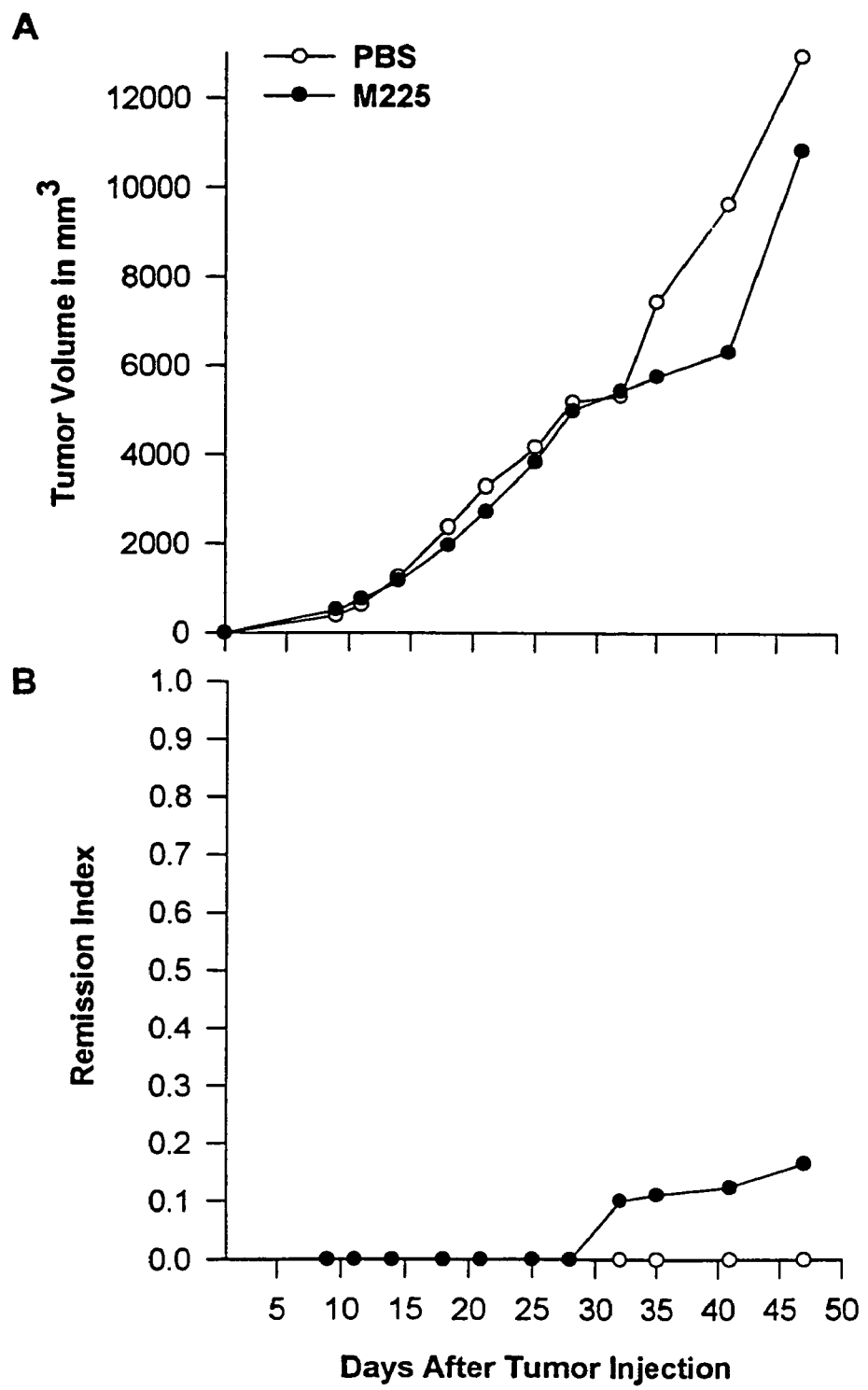
FIG. 1. Effect of 225 on the growth of established A431 tumor xenografts in nude mice. Animals were injected with $10^7$ cells in the flank. Treatments, consisting of PBS or 1 mg/animal of 225 twice weekly for 5 weeks, were begun when tumors reached an average volume of 2-300 mm³. Volumes and Remission Index (RI) were determined as described in the "Examples" section.

In one aspect of the invention, a polypeptide lacking the constant region and the variable light chain of an antibody comprises the first and second heavy chain complementarity determining regions of monoclonal antibody 225. These regions have the following amino acid sequences:

```
CDR-1    NYGVH              (SEQ ID NO:1)

CDR-2    GVIWSGGNTDYNTPFTSR (SEQ ID NO:2)
```

The peptide comprising the first and second complementarity determining regions mentioned above may be obtained by methods well known in the art. For example, the polypeptides may be expressed in a suitable host by DNA that encodes the polypeptides and isolated. The DNA may be synthesized chemically from the four nucleotides in whole or in part by methods known in the art. Such methods include those described by Caruthers in Science 230, 281–285 (1985).

The DNA may also be obtained from murine monoclonal 225, which was described by Mendelsohn, et al. U.S. Pat. No. 4,943,533. The hybridoma cell line which secretes monocloned Antibody 225 was deposited in the American Type Culture Collection, 10801 University Boulevard, Manassas, Va. 20110-2209 on Jun. 7, 1995. (Accession number HB 11935). Methods for obtaining the variable heavy chain region of antibodies are known in the art. Such methods include, for example, those described in U.S. patents by Boss (Celltech) and by Cabilly (Genentech). See U.S. Pat. Nos. 4,816,397 and 4,816,567, respectively.

The DNA encoding the protein of the invention may be replicated and used to express recombinant protein following insertion into a wide variety of host cells in a wide variety of cloning and expression vectors. The host may be prokaryotic or eukaryotic.

The polypeptide may contain either N Y G V H (SEQ ID NO: 1), G V I W S G G N T D Y N T P F T S R (SEQ ID NO: 2), or V I W S G G N T D Y N T P F T S(SEQ ID NO: 3). Alternatively, the polypeptide may contain the sequences G V I W S G G N T D Y N T P F T S R (SEQ ID NO: 2), or V I W S G G N T D Y N T P F T S (SEQ ID NO: 3).

The polypeptide may also be conjugated to an effector molecule. The effector molecule performs various useful functions such as, for example, inhibiting tumor growth, permitting the polypeptide to enter a cell such as a tumor cell, and directing the polypeptide to the appropriate location within a cell.

The effector molecule, for example, may be a cytotoxic molecule. The cytotoxic molecule may be a protein, or a non-protein organic chemotherapeutic agent. Some examples of suitable chemotherapeutic agents include, for example, doxorubicin, taxol, and cisplatin.

Some additional examples of effector molecules suitable for conjugation to the polypeptides of the invention include signal transduction inhibitors, ras inhibitors, and cell cycle inhibitors. Some examples of signal transduction inhibitors include protein tyrosine kinase inhibitors, such as quercetin (Grazieri et al., Biochim. Biophs. Acta 714, 415 (1981)); lavendustin A (Onoda et al., J. Nat. Prod. 0, 1252 (1989)); and herbimycin A (Ushara et al., Biochem. Int., 41, 831 (1988)). Ras inhibitors include inhibitors of ras farnesylation, such as the benzodiazepine peptidomimetics described by James et al. in Science 260 1937 (1993), which have the formula shown below:

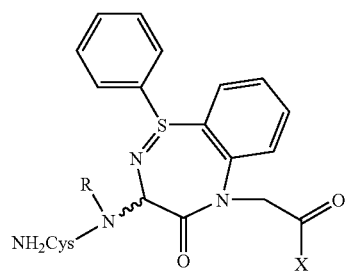

in which R is H or $CH_3$; and X is Methione, Serine, Leucine, or an ester or amide derivative thereof.

Proteins and non-protein chemotherapeutic agents may be conjugated to the polypeptides by methods that are known in the art. Such methods include, for example, that described by Greenfield et al., Cancer Research 50, 6600–6607 (1990) for the conjugation of doxorubicin and those described by Arnon et al., Adv. Exp. Med. Biol. 303, 79–90 (1991) and by Kiseleva et al., Mol. Biol. (USSR) 25, 508–514 (1991) for the conjugation of platinum compounds.

The invention further includes a modified antibody having the constant region of a human antibody, and the hypervariable region of monoclonal antibody 225. These modified antibodies are optionally conjugated to an effector molecule, such as a cytotoxic agent. The variable region other than the hypervariable region may also be derived from the variable region of a human antibody. Such an antibody is said to be humanized. Methods for making humanized antibodies are known in the art. Methods are described, for example, in Winter, U.S. Pat. No. 5,225,539.

The most thorough method for humanization of the 225 antibodies is CDR-grafting. As described in Example IV, the regions of the mouse antibody that are directly involved in binding to antigen, the complementarity determining region or CDRs, are grafted into human variable regions to create "reshaped human" variable regions. These fully humanized variable regions are then joined to human constant regions to create complete "fully humanized" antibodies. In order to create a fully humanized antibody that binds well to antigen, it is essential to carefully design the reshaped human variable regions. The human variable regions into which the 225 antibodies CDRs will be grafted must be carefully selected, and it is usually necessary to make a few amino acid changes at critical positions within the framework regions (FRs) of the human variable regions.

The reshaped human H225 variable regions, as designed, include up to a single amino acid change in the FRs of the selected human kappa light chain variable region and as many as twelve amino acid changes in the FRs of the selected human heavy chain variable region. The DNA sequences coding for these reshaped human H225 heavy and kappa light chain variable region genes are joined to DNA sequences coding for the human γ1 and human κ constant region genes, respectively. The reshaped human H225 antibody is then expressed in mammalian cells and tested, in comparison with mouse M225 antibody, and chimeric C225 antibody for binding to human EGF receptor expressed on the surface of A431 cells.

The variable region of the antibody outside of the hypervariable region may also be derived from monoclonal antibody 225. In such case, the entire variable region is derived from murine monoclonal antibody 225, and the antibody is said to be chimerized, i.e., C225. Methods for making chimerized antibodies are known in the art. Such methods include, for example, those described in U.S. patents by Boss (Celltech) and by Cabilly (Genentech). See U.S. Pat. Nos. 4,816,397 and 4,816,567, respectively.

The constant region of the modified antibodies may be of any human class, i.e., IgG, IgA, IgM IgD, and IgE. Any subclass of the above classes is also suitable, e.g., IgG1, IgG2, IgG3 and IgG4, in which IgG1 is preferred.

Any of the effector molecules mentioned above in connection with conjugation to a polypeptide can also be conjugated to chimeric or humanized antibodies of the invention. Doxorubicin, taxol, and cisplatin are preferred.

The polypeptides and antibodies of the invention significantly inhibit the growth of tumor cells when administered to a human in an effective amount. Examples of tumor cells that can be treated with the polypeptides and antibodies of the invention include glioblastomas, as well as cancers of the lung, breast, head, neck, and bladder. The optimal dose can be determined by physicians based on a number of parameters ingredient being administered, and the route of administration. In general, a serum concentration of polypeptides and antibodies that permits saturation of EGF receptors is desirable. A concentration in excess of approximately 0.1 nM is normally sufficient. For example, a dose of 100 mg/m$^2$ of C225 provides a serum concentration of approximately 20 nM for approximately eight days.

As a rough guideline, doses of antibodies may be given weekly in amounts of 10–300 mg/m$^2$. Equivalent doses of antibody fragments should be used at more frequent intervals in order to maintain a serum level in excess of the concentration that permits saturation of EGF receptors.

Some suitable routes of administration include intravenous, subcutaneous, and intramuscle administration. Intravenous administration is preferred.

The peptides and antibodies of the invention may be administered along with additional pharmaceutically acceptable ingredients. Such ingredients include, for example, immune system stimulators and chemotherapeutic agents, such as those mentioned above.

It has now surprisingly been found that, unlike the murine 225 antibody, the chimeric and humanized antibodies significantly inhibit tumor growth in mammals, even in the absence of other anti-tumor agents, including other chemotherapeutic agents, such as cisplatin, doxorubicin, taxol, and their derivatives. Significant inhibition may mean the shrinkage of tumors by at least 20%, preferably 30%, and more preferably 50%. In optimal cases, 90% and even 100% shrinkage of tumors is achieved. Alternatively, significant inhibition may mean an RI greater than 0.3, preferably greater than 0.4, and more preferably greater than 0.5.

The significant inhibition of tumor growth and/or increase in RI manifests itself in numerous ways. For example, there is an increase in life expectency and/or a stabilization of previously aggressive tumor growth.

In cases where the side effects of chemotherapeutic agents are too severe for a patient to continue such treatments, C225 may be substituted for the chemotherapeutic agents, and achieve comparable results.

For example, the results shown in Example III-1 indicate that, while the in vitro inhibitory properties of 225 and C225 are comparable, the in vivo effects of the antibodies differ considerably. Antibody isotype does not play a significant role in the differences seen between 225 and C225 (e.g., mouse IgG1 vs. human IgG1). A recent report indicates that neither 225 nor C225 induced complement mediated lysis to any degree and the ADCC reactivity of these antibodies appeared to be species specific. Naramura et al., Immunol. Immunother. 37, 343–349 (1993). Therefore, if inhibition of A431 xenografts was mediated through immune responses, 225 should be the more potent antibody because of its ability to activate the murine effector cells involved in ADCC. The opposite is, in fact, the case.

In addition, there were differences in the way individual animals within a group responded to treatment with either 225 or C225. It appeared that C225 alone was very effective in inducing complete tumor remission at the 1 mg dose whereas 225 at this dose level showed marginal effects. In Experiments 2 and 3 of Example III-1, about 40% of the animals were tumor free at the end of each study. The animals responding in those groups usually had smaller tumors at the beginning of the treatment protocols, once again indicating that initial tumor burden plays a role in the biological efficacy of C225. Significantly, animals treated with either 225 or C225 showed greater survival characteristics compared to the PBS control group in all studies.

As demonstrated in Example III-2, prostatic carcinoma is also an appropriate target for anti-EGFR immunotherapeutic intervention with C225. Since the metastatic prostatic carcinoma cells coexpress TGF-α as well as the EGFR, late stage prostatic carcinoma is an especially appropriate target.

Figure 7:
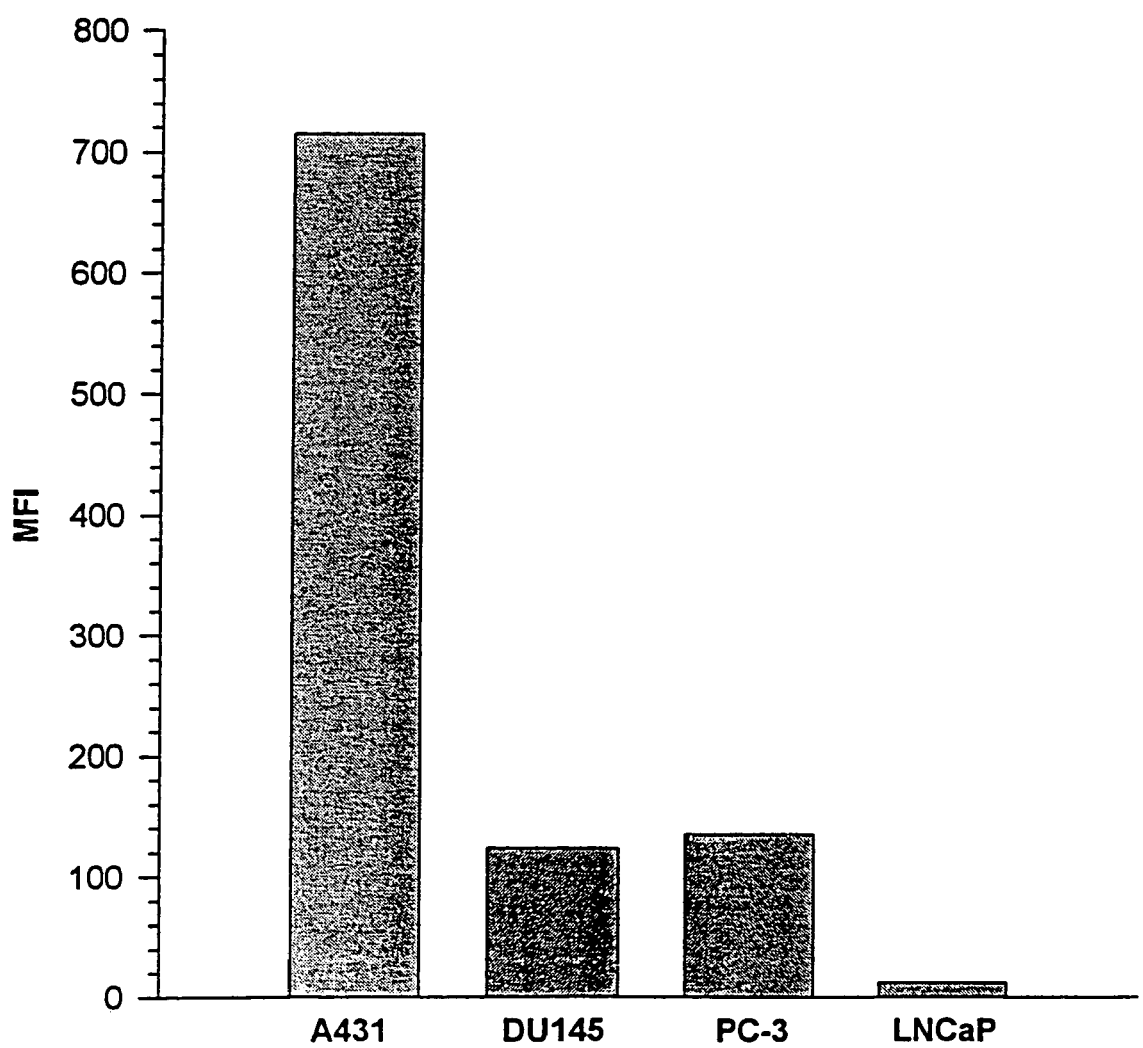
FIG. 7. FACS analysis of EGFR expression on human prostatic carcinoma cell lines. LNCaP (human prostatic carcinoma, androgen-dependent), DU 145 and PC-3 (human prostatic carcinoma, androgen-independent), and A431 (human epidermoid carcinoma) cells were removed with EDTA from the growth flasks and stained with C225. Data are presented as MFI (Mean Fluorescence Intensity), an indirect measure of antigen expression. The results shown in this figure are representative of at least 5 experiments.

Example III-2 describes the biological effects of C225 on the activation of the EGFR in cultured human prostatic carcinoma cells and the growth of prostate xenografts in nude mice. The in vitro experiments were designed to determine the expression levels of the EGFR on three human prostatic carcinoma cell lines and the ability of C225 to block the functional activation of the receptor. FIG. 7 shows the results of a FACS analysis comparing EGFR expression on A431 cells to levels seen on LNCaP (androgen-dependent) and PC-3 and DU 145 (androgen-independent) cells. Both PC-3 (MFI=135) and DU-145 (MFI=124) cells expressed about 7 fold less receptor than A431 cells (MFI=715). Since MFI is an indirect measure of antigen density, both PC-3 and DU 145 cells would appear to express about $10^5$ receptors each. LNCaP cells, on the other hand, expressed very low levels of surface receptor (MFI=12).

As shown above, the EGFR expressed by A431 cells can be stimulated by exogenously added ligand (EGF) and C225 can abrogate activation of the receptor.

Figure 8:
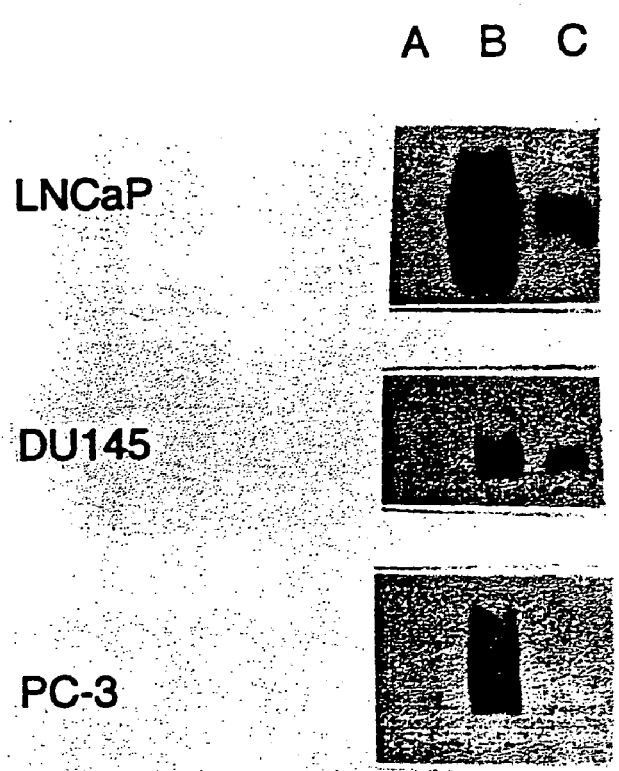
FIG. 8. Inhibition of EGF-induced phosphorylation of the EGFR by C225. LNCaP, DU 145, and PC-3 monolayers were stimulated with EGF in the presence or absence of C225. Cells were lysed, subjected to SDS PAGE, blotted, and screened with a mouse monoclonal antibody to PTyr (UBI, Lake Placid). Lane A: no additions (basal level of EGFR phosphorylation); Lane B: stimulation of EGFR with 10 ng/ml EGF for 15 minutes at room temperature in the absence of C225; Lane C: stimulation of EGFR with EGF in the presence of 10 ug/ml of C225.

FIG. 8 shows the results of similar studies with the prostatic lines. The addition of EGF to LNCaP, PC-3, and DU 145 induced phosphorylation of the EGFR that was blocked by C225 with high efficiency. These data indicate that C225 effectively inhibits ligand-activated EGFR signalling pathways, and has anti-tumor activity when EGFR activation is required for growth in vivo.

The ability of C225 to inhibit tumor growth in vivo was tested against established DU 145 xenografts in athymic nude mice. DU 145 cells were innoculated at $10^6$ cells per animals in combination with matrigel. Tumors developed in 100% of the animals within 20 days. Preliminary experiments had shown that a dose level of 1 mg (10x) induced significant tumor inhibition. For these studies, C225 was injected at a 0.5 mg (10x) dose level.

Figure 9:
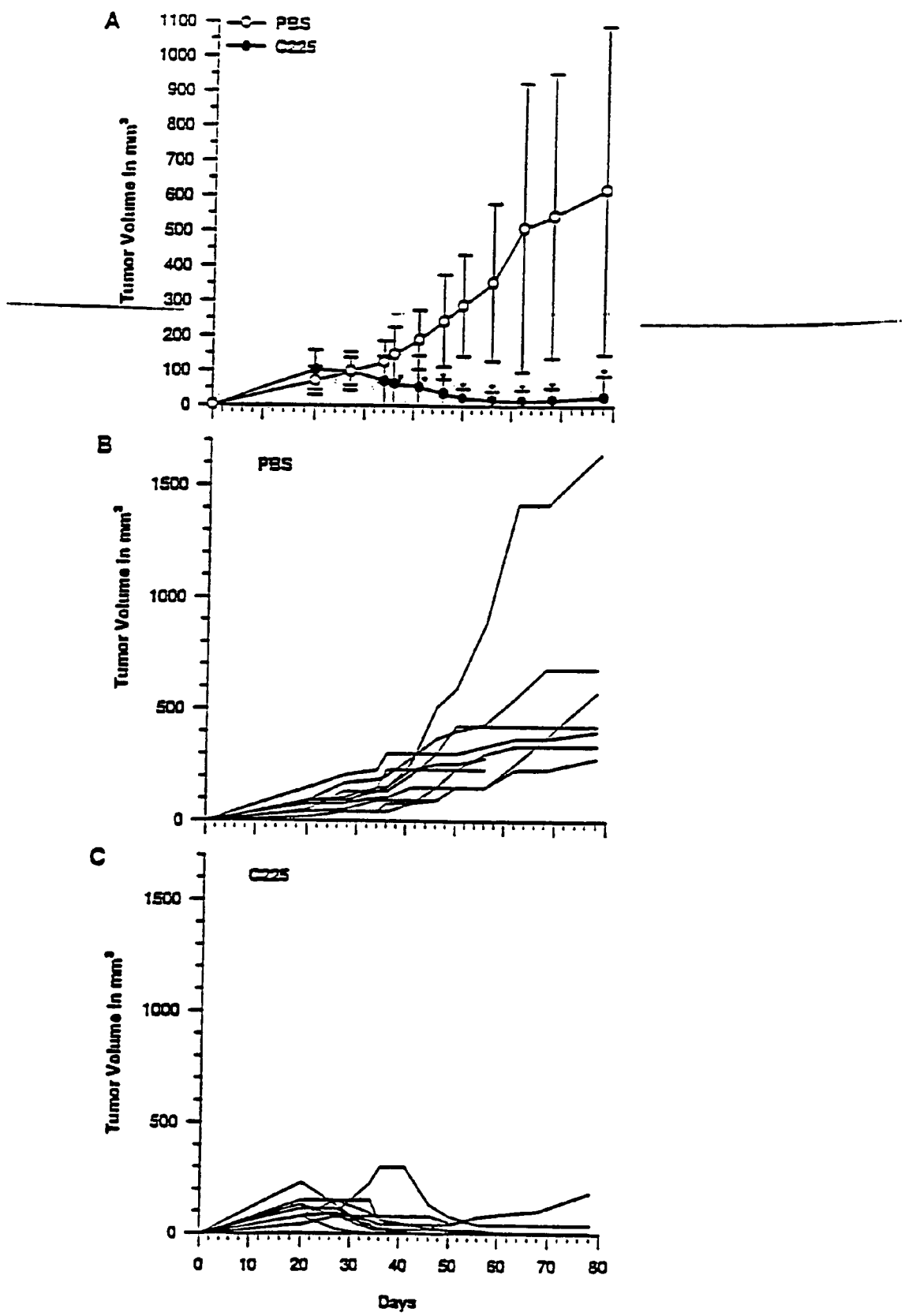
FIG. 9. Growth inhibition of established DU 145 xenografts by C225. One million DU 145 cells in matrigel were innoculated into nude mice (males, nu/nu). After tumors reached an average volume of approximately 100 mm³ (day 20), animals were randomized (10 animals per group) and treated with either PBS (control) or C225 (0.5 mg/dose, 10×). Animal were treated for 35 days and followed for an additional 3 weeks. Mice that were tumor-free or carrying small tumors were maintained for an additional 3 months. Significance (shown by astericks in FIG. 3A) was determined by a Student's T-test and a p value<0.5 was considered significant. A: average tumor volume; B: growth characteristics for tumors in the PBS group; C: growth characteristics for tumors in the $C_{2\text{-}25}$-treated groups.
Figure 10:
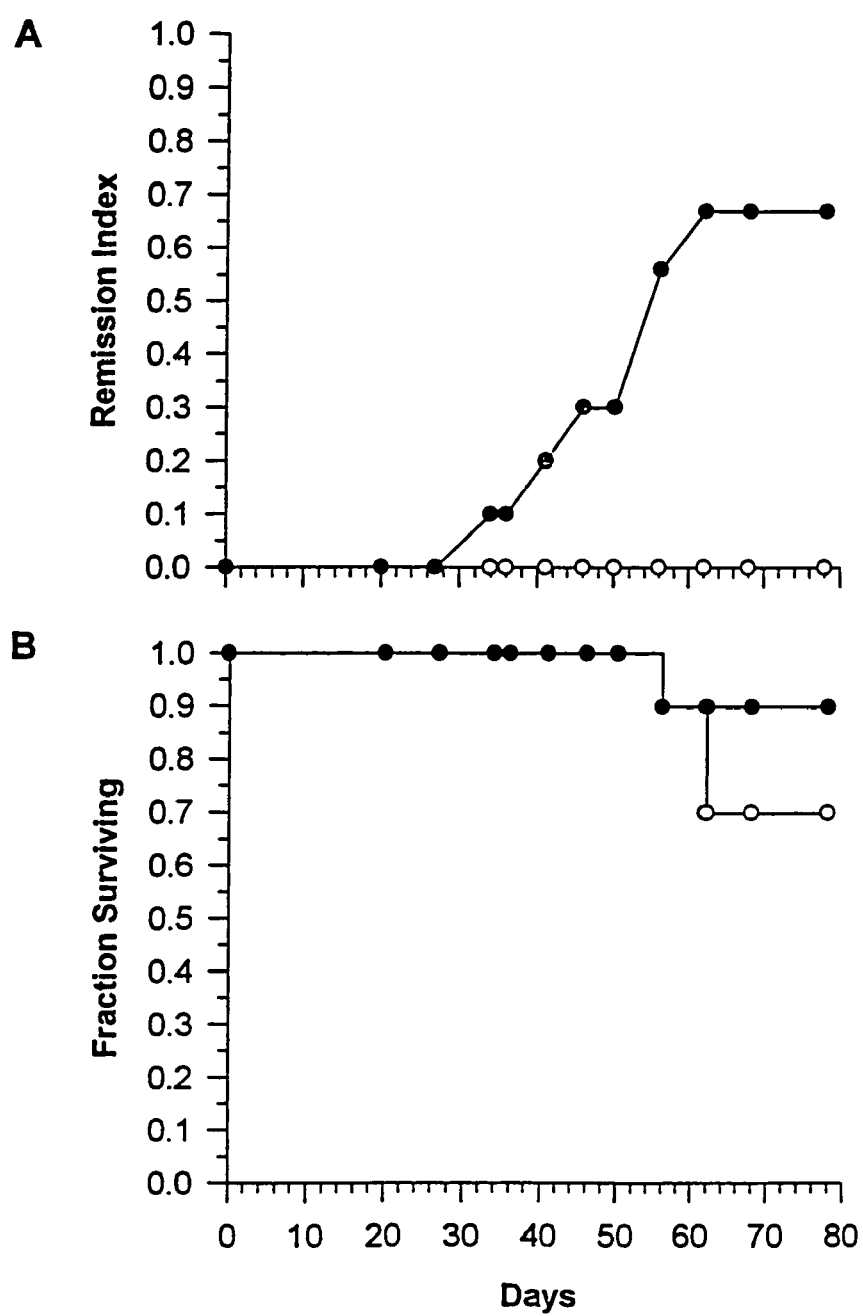
FIG. 10. Effects of C225 on tumor elimination and surviva. The complete elimination of tumors during the course of the study was defined by a Remission Index (RI). Animal mortality during the study was considered a treatment failure and included in the analysis. A: Remission Index; B: Survival curve. The empty and filled circles in FIG. 10 have the same meanings as in FIG. 9.

As shown in FIG. 9, C225 alone was effective in significantly inhibiting the growth of established DU 145 xenografts (p<0.5). The overall therapeutic effect was apparent by day 34 and significant with respect to the control group by day 36 (FIG. 9A). All tumors in the sham-injected group continued to grow throughout the course of the study (FIG. 9B) but the anti-tumor effect of the antibody was seen throughout the study (FIG. 9C). Although spontaneous remissions in PBS-treated animals were never seen in this model, 60% of the C225 treated animals were tumor free by day 60 (FIG. 10A) and remained tumor-free for an additional 90 days after termination of the antibody injections. In addition, tumors that did not disappear in the C225 group grew extremely slowly after treatment was stopped (day 55; FIG. 9C) suggesting a long-lived effect of the antibody. There was no significant difference in the survival curves during the course of treatment (FIG. 10B).

Example III-2 clearly shows that C225 was capable of inhibiting the growth of established, EGFR-positive DU 145 xenografts and could induce long-lived tumor remissions in a high percentage of treated animals. These results could not be predicted from the in vitro data.

Not all cell lines that express EGFR at levels similar to those seen in DU 145 cells respond to C225 in vivo. For example, KB cells (human epidermoid carcinoma) express about $2\times10^5$ EGFR per cell and activation of the receptors by EGF was blocked by C225 in vitro. However, KB xenografts did not respond to a treatment regimen including a 1 mg dose (x10) of C225, a level able to induce complete remissions in 100% of animals carrying established A431 tumors. As surprisingly shown in Example III-2, treatment of mice innoculated with DU 145 tumor cells with C225 alone at a 0.5 mg dose (xl 0) led to significant tumor regressions in all treated animals. Sixty percent of the mice were in complete remission following termination of the treatment. Blockage of receptor activaton by C225 also has clinical implications for the treatment of metastatic prostatic carcinoma in humans, especially during the late stages of the disease.

EXAMPLES

Example I. Materials

Example I-1

Cell Lines and Media

A431 cells were routinely grown in a 1:1 mixture of Dulbecco's modified Eagle's medium and Ham's F-12 supplemented with 10% fetal bovine serum, 2 mM L-glutamine, and antibiotics.

The androgen-independent and dependent human prostatic carcinoma cell lines (DU 145, PC-3 and LNaP) were obtained from the ATCC (Rockville Md.) and routinely maintained in RPMI 1640 medium (Sigma, St. Louis, Mo.) supplemented with 10% fetal bovine serum (Intergen, Purchase N.Y.) and 2 mM L-gluatmine (Sigma). Cells were checked regularly for the presence of mycoplasma.

Example 1–2

Preparation and Purification of M225 and C225

The 225 antibody was grown as ascites in pristane primed Balb/c mice. Ascites fluid was purified by HPLC (ABX and Protein G) and determined to be >95% pure by SDS PAGE.

Human clinical grade C225 was grown in proprietary serum free medium in 300 liter lots. After clarification, the concentrated broth was purified on a series of chromatographic columns and vialed under aseptic conditions. Purity was determined to be >99% by SDS PAGE.

Example I-3

Preparation of Doxorubicin-C225 Conjugates

C225 doxorubicin conjugates (C225-DOX) were prepared using a modification of the method described by Greenfield et al., Cancer Research 50, 6600–6607 (1990). Briefly, Doxorubicin was reacted with the crosslinking agent PDPH (3-[2-pyridyldithio]propionyl hydrazide) (Pierce Chemical Co.) to form the acyl hydrazone derivative doxorubicin 13-[3-(2-pyridyldithiol)propionyl] hydrazone hydrochloride. C225 was thiolated with the reagent N-succinimydyl 3-(pyridyldithio) propionate and reacted with doxorubicin hydrazone to form a conjugate containing a hydrazide as well as a disulfide bond. The complex was purified by gel filtration at neutral pH. The C225-doxorubicin conjugate was stable at neutral to alkaline pH (pH 7–8) and was stored at 4° C. The conjugate was readily hydrolyzed at pH 6, releasing active Doxorubicin.

Example I-4

Chimerization of Antibody 225

Example I-4A

Cloning of H and L Chain cDNAs

The media containing the 225 mouse hybridoma cell line was expanded to one liter in tissue culture flasks. Total cell RNA was prepared by lysing washed cells in guanidine isothiocyanate containing 2-mercaptoethanol, shearing the solution in a dounce homogenizer to degrade cell DNA and layering the preparation on a 10 ml cesium chloride cushion.

After centrifugation at 24,000 rpm for 16 hr. the pellet was resuspended in Tris-EDTA (TE) buffer and precipitated with ethanol. The poly A(+) mRNA fraction was isolated by binding to and elution from oligo dT cellulose. A cDNA library was prepared using the poly A (+) mRNA as template and oligo dT as the primer. The second strand was synthesized by nick translation using RNase H and DNA polymerase I. The double-stranded DNA was passed through a 2 ml Sepharose G75 column to remove oligo dT and small entities. The purified DNA was then ligated into a polylinker with the sequence:

5'-AATTCTCGAGTCTAGA-3' (SEQ ID NO: 98)

which encodes an Eco RI four base sticky end for ligation to the cloning vector, and the restriction sites for Xho I and Xba I for subsequent manipulations of the cDNAs. The ligated cDNA was then size-selected by electrophoresis on a 5% polyacrylamide gel. The appropriate size fractions (~1500 bp for H chain and ~900 bp for L chain cDNA) were electroeluted from gel slices and ligated to Eco RI-digested lambda gt10 phage DNA. Libraries were generated by packaging the ligation products in vitro and plating recombinant phage on lawns of *E. coli* strain C600 HFL. Phage containing H and L cDNAs were identified by phage filter lifts that were hybridized with radiolabeled oligonucleotides of the mouse kappa and gamma constant region. The identified phage were restriction mapped.

Isolates with the longest cDNA inserts were subcloned in a plasmid vector (Eco RI-Bam HI fragments for heavy (H) chain V regions and Eco RI-Hpa I fragments for light (L) chain variable (V) regions) and DNA sequenced. The subcloned fragments contained the complete V region and a small portion of associated mouse constant (C) region. A total of eight L chain cDNAs were sequenced and represent four different mRNAs. Three full-length H chain cDNAs were sequenced encoding the same V region and a portion of the correct gamma 1 C region. Three other isolates containing gamma 2a sequence were also identified but were not studied further. To identify the correct L chain cDNA, a sample of mouse 225 antibody was sequenced by automated Edman degradation after first separating the H and L chains by SDS reducing gel electrophoresis and blotting to membranes.

The sequence obtained for the L chain matched one of the cDNAs. This isolate was rearranged to J5 and was found to be 91% homologous with Vk T2. The H chain V region was found to be 96% homologous with VH 101 subgroup VII-1.

Example I-4B

Adaption of cDNAs and Construction of Expression Vectors

The V regions were adapted for expression by ligating the body of each to a synthetic DNA duplex encoding the sequence between the closest unique restriction site to the V/C junction and the exact boundary of the V region. To this was ligated a second, short intron sequence which, when joined, restores a functional splice donor site to the V region. At the end of the intron for the L chain is a Bam HI site and at the end of the H chain intron is a Hind III site. The adapted L Chain V region was then isolated as a Xba I-Bam HI fragment (the Xba I site was in the original linker used for cDNA cloning) while the adapted H chain V region was isolated as a Xho I-Hind III fragment.

The expression vector pdHL2, containing human kappa and human gamma 1 constant regions, was used for insertion of the adapted L chain V region. The resulting plasmid, pdHL2-Vk(225), was then digested with Xba I and Bam HI and used for the insertion of the adapted L chain V region. The resulting plasmid, pdHL2-Vk(225), was then digested with Xho I and Hind III and used for the insertion of the adapted H chain V region. The final vector was identified by restriction mapping and identified as pdHL2-ch225.

Example I-4C

Expression of Chimeric 225 in Transfected Hybridoma Cells

The pdHL2-ch225 plasmid was introduced into hybridoma Sp2/0 Ag14 cells by protoplast fusion. The bacteria harboring the plasmid were grown to an optical density of 0.5 at 600 nm at which time chloramphenicol was added to arrest growth and amplify the plasmid copy number. The following day the bacteria were treated with lysozyme to remove the cell wall and the resulting protoplasts were fused to the hybridoma cells with polyethylene glycol 1500. After fusion, the cells were grown in antibodies to kill any surviving bacteria and were plated in 96-well plates. The selection medium (containing methotrexate (MTX) at 0.1 µM) was added after 24–48 hours to allow only the transfected cells to grow, by virtue of their expression of the marker gene (dehydrofolate reductase) present on the expression plasmid.

After two weeks, several MTX-resistant clones were obtained that were then tested for antibody expression. Culture supernatants were added to wells coated with an anti-human Ig (Fc-specific) antibody as the capture reagent. The detection system was an HRP-conjugated goat anti-human kappa antibody. The majority of clones were found to be secreting human antibody determinants and the three highest producers were further adapted to grow at 1 µM and then 5 µM methotrexate. Two of the lines, designated SdER6 and SdER14, continued to grow well at the higher levels of MTX and were subcloned by limiting dilution. The productivity of the subclones was tested by seeding cells at $2 \times 10^5$ cells per ml in growth medium and measuring the accumulated antibody on day 7. The two highest producers from the first subcloning were lines SdER6.25 and SdER14.10. These were subcloned a second time and the final three candidate lines were designated SdER6.25.8, SdER6.25.49, and SdER14.10.1. Clone SdER6.25.8 was selected based on expression of antibody.

Example I-5

Analysis of C225 Expressed from SdER6.25.8

Studies with antibody produced from the clone SdER6.25.8 were conducted to characterize the nature of the antibody. Culture supernatants from the transfected cell clones expressing C225 antibody were tested for their ability to bind human tumor cells expressing different levels of EGF receptor. A431 epidermal carcinoma cells (high expressors) were intensely stained while M24 melanoma cells (expressing 10-fold fewer receptors) were moderately stained. A neuroblastoma line, IMR-32, which does not express EGF receptor, was not stained.

Example 1–6

Effects of Chimerizing the C225 Antibody

The apparent Kd was found to be 0.1 and 0.201 nM for C225 and 1.17 and 0.868 nM for 225, using ELISA and SPR methods, respectively (Table 1). These results were similar to published data for C225 (Kd=0.39 nM) and 225 (Kd=0.79 nM, Kd=1 nM) as shown in Table 1. The antibodies were found to inhibit the proliferation of cultured A431 cells to the same extent (Table 2). In addition, 225 and C225 were able to block EGF-induced phosphorylation of the EGFR in A431 cells. These results indicated that chimerization of 225 did not affect the biological properties of the antibody and increased the relative binding affinity of C225 for EGFR.

Example II

Methods and Assays

Example II-1

Relative Affinity Measurements by ELISA

The relative binding affinity of the antibodies was determined using an ELISA protocol previously described by Lokker et al. J. Immunol. 146, 893–898 (1991). Briefly, A431 cells ($10^4$ or $10^5$ per well) were grown in 96 well microtiter plates overnight at 37° C. Cells were fixed with 3.7% neutral buffered formalin for 10 minutes at room temperature. After washing three times with PBS, wells were blocked with 1% bovine serum albumin in Hank's balanced salt solution for two hours at room temperature. C225 or 225 were added to the wells at various concentrations (serial dilutions starting at 50 nM). After a two hour incubation at 37° C., plates were extensively washed with PBS and incubated with goat anti-human antibody (Sigma, St Louis Mo.; 1:1000) for one hour at 37° C. Plates were washed and the chromogen TMB (Kirkegaard and Perry, Gaithersburg Md.) added for 30 minutes in the dark. The color reaction was stopped with 1 N sulfuric acid and the plates read in an ELISA reader at 450 nm. The relative binding affinity is defined as the concentration giving the half maximal OD.

Example 11–2

Affinity Constants of 225 and C225 Using Surface Plasmon Resonance Technology (SPR)

The apparent binding affinities of M225 and C225 were also determined using the InAcore™ (Pharmacia Biosensor, Piscataway N.J.; manufacturer's application note 301 and O'Shannessy et al., Anal. Biochem. 212,457468 (1993). Briefly, soluble recombinant EGFR was immobilized on sensor chips via amino groups as described by the manufacturer. Real time binding parameters of 225 and C225 to EGFR was established at various antibody concentrations and the apparent Kd was calculated from the binding rate constants obtained via non linear fitting using Biaevaluation™ 2.0 Software.

Example II-3

In vitro Inhibition of Cell Growth with 225 and C225

The in vitro inhibitory activity of 225 and C225 was determined by plating A431 cells (300–500 per well) in 96 microtiter plates in complete growth medium. After adding C225 or 225 in various concentrations (4 replicates per concentration), plates were incubated for 48 hours at 37° C. followed by a 24 hour pulse with 3H-thymidine. Cells were harvested, collected on filter mats and counted in a Wallace Microbeta scintillation counter to determine percent inhibition. Percent inhibition compares the decrease in 3H thymidine incorporation of antibody-treated cells with cells grown in the absence of antibody.

Example II-4

Animal Studies

Athymic nude mice (nu/nu; 6–8 weeks old females) were obtained from Charles River Laboratories. Animals (10 mice per treatment group) were innoculated in the right flank with 10' A431 cells in 0.5 ml of Hank's balanced salt solution. Mice were observed until tumors were visible (about 7–12 days) and had reached an average volume of 150–300 mm³. At that time, antibody therapy was begun. The therapy included twice weekly intraperitoneal injections (varying concentrations in 0.5 ml of PBS) over 5 weeks. U 1 animals received injections of PBS. Tumors were measured two times per week and volumes calculated using the following formula: $\pi/6 \times$larger diameter$\times$(smaller diameter)$^2$. Animals were followed at least 3 weeks after the final antibody treatment (8 weeks after the start of therapy) at which time U 1 and test animals with extremely large tumors were euthanized. Tumor free animals and animal with small tumors were followed for an additional 2–3 months. Statistical analysis of tumor growth in each of the studies was done using a two tailed Student's T-test.

In addition to demonstrating growth inhibitory effects of the antibodies, many animals were found to be in complete remission (i.e., tumor free). This biological effect was quantified as a Remission Index (RI), defined as the number of tumor free mice/total animals within a treatment group. Termination occured at the time of euthanasia for animals with large tumors, and 2–3 months later for other animals. Animals that died during treatment were excluded from this analysis. For example, one complete remission among eight surviving animals equals an RI of 0.125.

Example III

Biological Activity of C225

Example III-1

The Capacity of the Antibodies to Inhibit the Growth of A431 Xenografts in Nude Mice Animals were inoculated in the flanks with A431 cells. Tumors of 150–300 mm³ appeared by day 7–10. Refering to Experiments 14 in Table 3, animals were then randomized and injected with PBS or 225 (Exp 1), PBS, 225, or C225 (Exp 2); and PBS or C225 (Exp 3 and 4). In Experiments 1–3, animals received injections of 1 mg of antibody (in 0.5 ml PBS) twice weekly over 5 weeks for a total dose of 10 mg of antibody per animal. In Exp 4, animals received one of three possible doses: 1, 0.5, and 0.25 mg/injection for total doses of 10, 5, and 2.5 mg, respectively. Tumors were measured twice weekly over the course of treatment. Tumor-free animals and animals with small tumors continued to be monitored for 2–3 months following the sacrificing of animals with large tumors.

Figure 2:
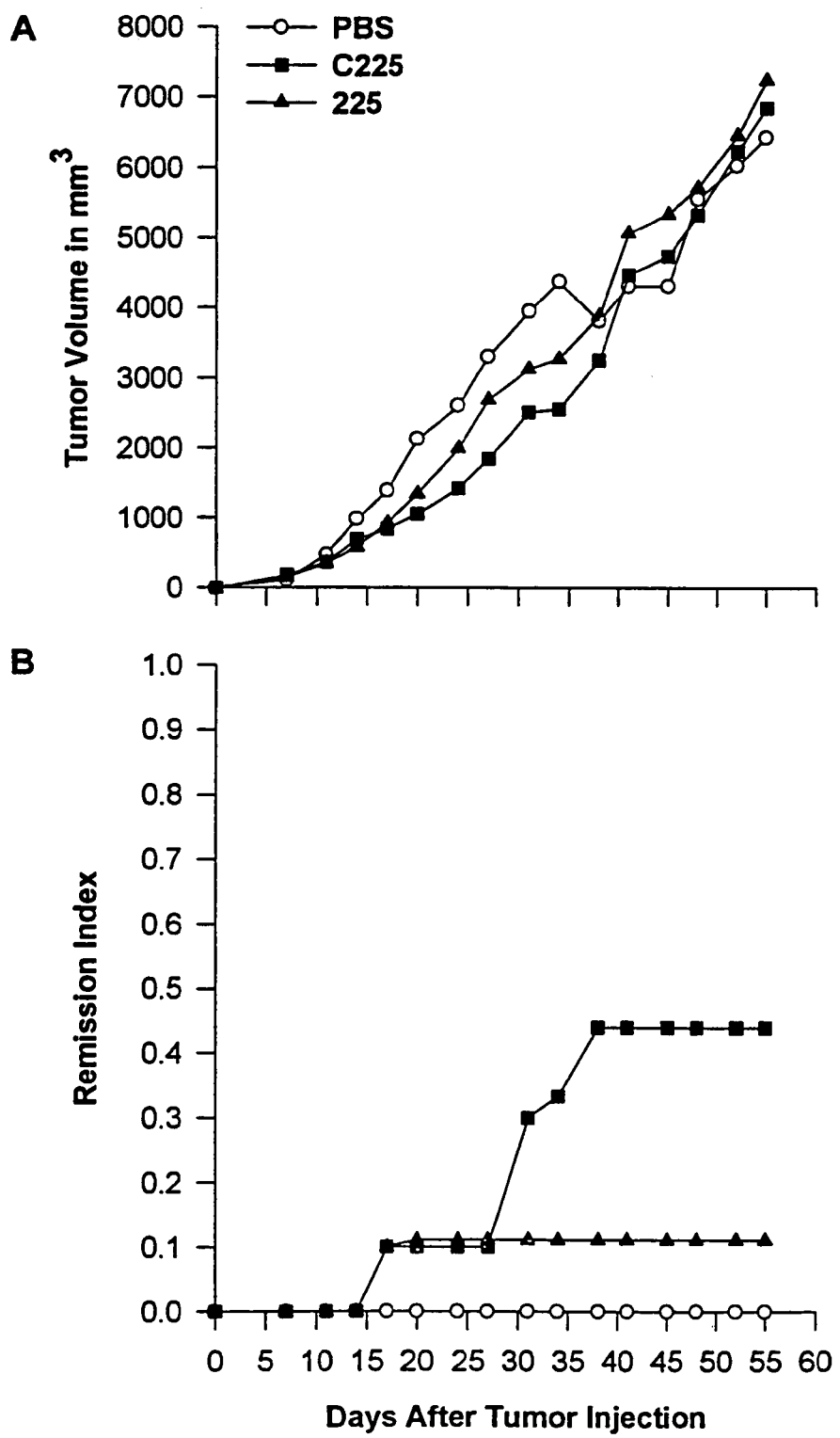
FIG. 2. Effect of 225 and chimerized 225 (C225) on the growth of established A431 tumor xenografts in nude mice. Animals were treated with 1 mg/mouse of PBS twice weekly for 5 weeks. A: Average tumor volumes; B: Remission Index. The apparent tumor regression in the PBS control group at day 37 was due to the death of 3 out of the 10 animals within the group at this time and the concommitant decrease in overall tumor volume.

FIG. 1 shows the effect of 225 on the growth of A431 tumors in nude mice (Exp 1). The average tumor volumes of the experimental and U 1 groups were similar (FIG. 1A) and only one complete tumor remission was observed (Remission Index (RI) of 0.17; FIG. 1B and Table 3). A comparison of 225 and C225 is shown in FIG. 2 (Exp 2 in Table 3). Although there was no significant difference in average tumor size between the groups, animals treated with C225 had an RI of 0.44 (i.e., 4/9 complete remissions) compared to an RI of 0.11 for 225 (FIG. 2B and Table 3). The apparent tumor regression for the PBS U 1 group at day 37 (FIG. 2A) was attributable to the death of 3/10 animals at this time and the concomitant decrease in overall tumor volume. A similar RI for C225 was seen in Exp 3 (FIG. 3B; RI=0.4). In addition, inhibition of tumor growth by C225 was also found to be significant when compared to the growth of xenografts in PBS-treated mice (FIG. 3A; $p<0.02$ following day 32).

Figure 3:
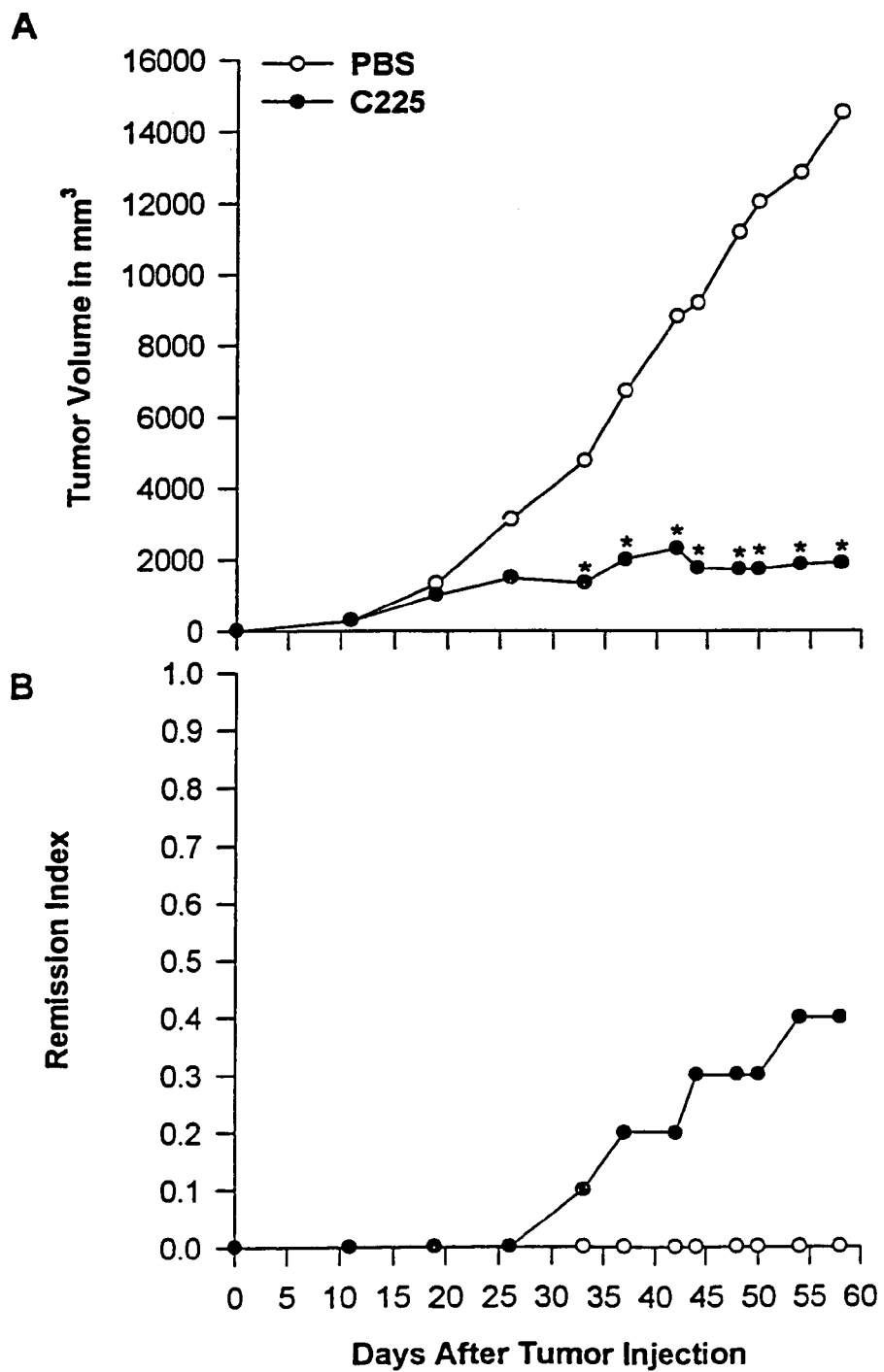
FIG. 3. Effect of C225 on the growth of established A431 xenografts in nude mice. Animals were treated with 1 mg of C225 or PBS twice weekly for 5 weeks. The average tumor volume of the C225 group showed statistically significant biological effects compared to control (see text) A: Average tumor volumes (asterisks show statistical significance with respect to control); B: Remission Index.
Figure 4:
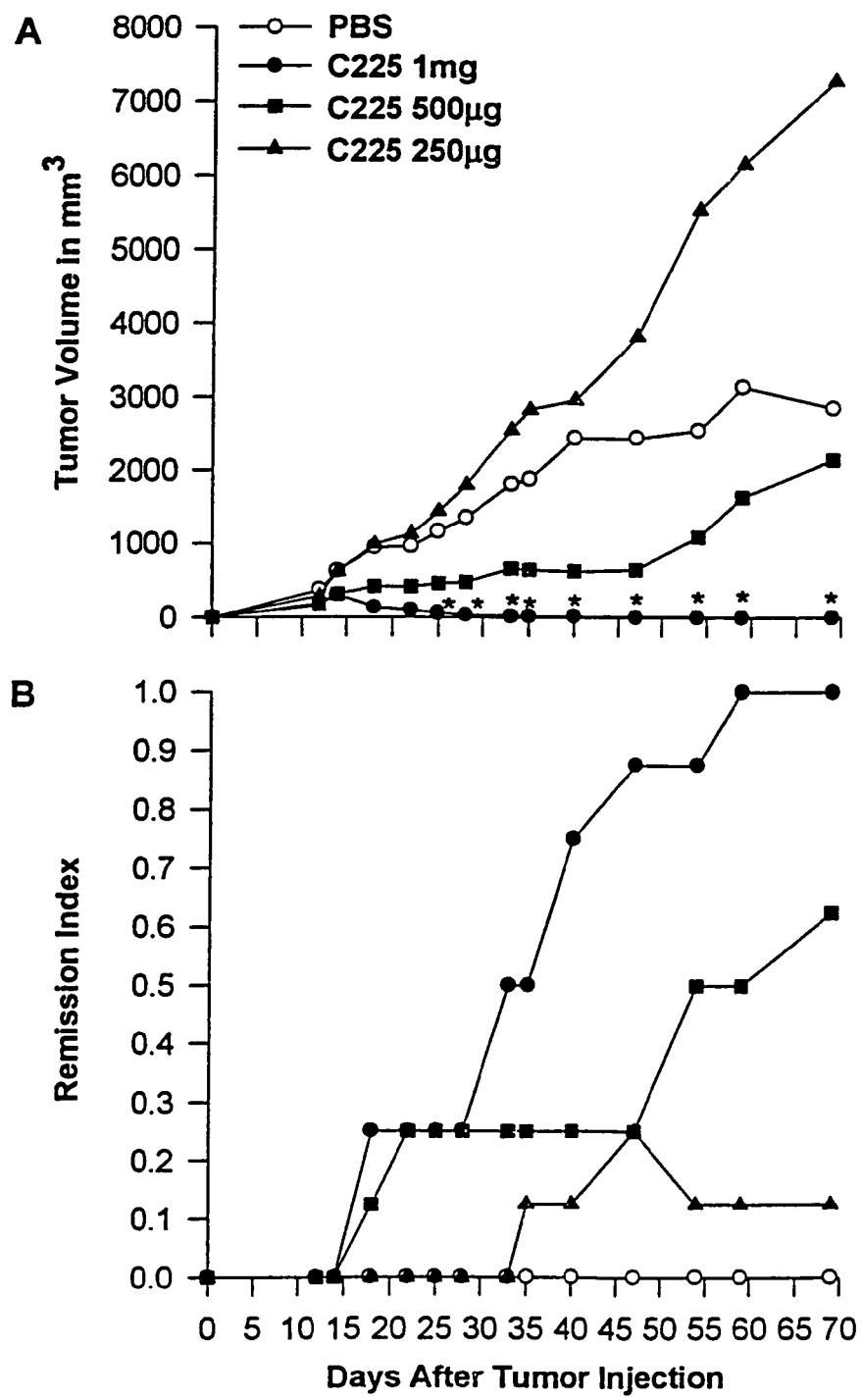
FIG. 4. Dose response of C225 on the growth of established A431 xenografts in nude mice. Animals were treated with PBS, 1, 0.5, or 0.25 mg/animal twice weekly for 5 weeks as described in Materials Methods. Animals treated with 1 mg/dose of C225 showed statistically significant biological effects compared to control (see text). A: Average tumor volumes (asterisks define statistical signifiance with respect to control); B: Remission Index. The drop in RI for the 250 ug dose group on day 47 resulted from the reappearance of a tumor in an apparent tumor-free animal. (In this instance, the effect of C225 was transient.)

Because a number of animals receiving C225 showed tumor regressions at the 1 mg/injection level, the lowest biologically effective dose was defined. FIG. 4 shows the results of the dose reponse experiment (Exp 4). All animals receiving 1 mg/injection underwent complete remission and remained tumor free for over 100 days following termination of the antibody injections (FIGS. 4A and B; Table 3). These results are highly significant with p values varying from $p<0.006$ on day 33 to $p<0.0139$ on day 59. In Experiments 2 and 3, about 40% of the animals receiving the 1 mg dose of C225 underwent complete remission although C225 showed significant tumor regression in Exp 3 (FIG. 3). The increased efficacy of the 1 mg dose in Experiments 3 and 4 in significantly reducing average tumor volume versus U 1 may have occured because mice carrying smaller tumors were used at the start of the treatment protocols in these experiments (152 mm [Exp 4] and 185 mm$^3$ [Exp 3] vs. 267 mm$^3$ [Exp.2]). These data suggest that the clinical effectiveness of C225 may be related to tumor burden.

At the 0.5 mg dose in Exp 4, the overall inhibition of tumor growth was not statistically significant because of the large variations in tumor volume among animals of both the PBS and the 0.5 mg groups. However, the RI was high for the 0.5 mg group (RI=0.63; FIG. 4b and Table 2) indicating that the antibody induced anti-tumor responses in individual animals. Interestingly, the 0.5 mg dose group in Exp 4 had a higher RI than the 1 mg dose group in Exp 3. This result may be attributed to the effects of tumor burden. Although the average starting volume for tumors in the 0,5 mg dose group was 160 mm$^3$, there was great variability in tumor size among individual animals. A number of animals carried smaller tumors (<100 mm$^3$) that are most susceptible to the biological effect of C225. At 0.25 mg dose, average tumor growth appeared to be greater than the PBS U 1. This was due to the inclusion within this group of two animals with large tumors (760 and 1140 mm$^3$) at the start of the treatments which resulted in an increase in average tumor volume during the course of Exp 4. Overall, there is no significant difference between these groups but it is interesting to note that one animal (⅛) at the 0.25 mg dose was tumor free at the end of the study (RI=0.13). At day 47, there appeared to be a drop in the RI. At this time, a tumor reappeared in one mouse that had apparently undergone a complete remission. In this single case, C225 had a transient biological effect. This animal is not included in Table 3. As with the 1 mg dose group, tumor-free animals in the 0.5 and 0.25 mg groups remained tumor free a minimum of 2–3 months after the PBS control mice were sacrificed.

TABLE 1

DISSOCIATION CONSTANTS (Kd) FOR 225 AND C225
AS DETERMINED BY VARIOUS METHODS

| METHOD* | RECEPTOR FORM | Kd(nM) 225 | Kd(nM) C225 | REFERENCE |
|---|---|---|---|---|
| Scatchard | A431 Lysates | 1 | nd | Cancer Res. 53, 4322–4328 (1993) |
| Scatchard | M24met cells | 0.78 | 0.39 | Immunol. Immunother. 37, 343–349 (1993) |
| ELISA | Fixed A431 cells | 1.17 | 0.147 | |
| SPR | Soluble receptor | 0.868 | 0.201 | |

*Scatchard results are expressed as Kd, SPR results as apparent Kd, and ELISA data as the apparent affinity, a relative measure of the Kd. See Materials and Methods for description of the generation of the ELISA and SPR data.

TABLE 2

IN VITRO INHIBITION OF A431 CELLS
BY C225 AND 225

| | % INHIBITION | |
|---|---|---|
| ug/ml of Antibody | C225 | 225 |
| 10 | 50 | 50 |
| 5 | 26 | 24 |
| 2 | 25 | 28 |
| 1 | 22 | 21 |

The results shown in Table 2 represent a typical experiment in which the ability of 1225 and C225 to inhibit the growth of A431 was tested in vitro. Details are described above. Percent inhibition is defined as the decrease in 3-H thymidine incorporation of antibody-treated samples (4 replicates/concentration) versus cells growing in the absence of antibody.

Table 3 represents a comparison of complete tumor remissions in athymic nude mice carrying established A431 tumors following treatment with PBS, 225, or C225 twice weekly for 5 weeks. Animals were treated with 1 mg of antibody in 0.5 ml of PBS by the intraperitoneal route except for study 4, which is a dose response experiment in which mice were given 1, 0.5, or 0.25 mg/injection. Tumor measurements were done as described above. This chart describes the RI at the time when the animals (PBS control and test) carrying large tumors were euthanized. All animals showing complete remissions or small tumors were followed for an additional 2–3 months. The differences in total number of animals results from death of mice within these treatment groups during the course of the experiments.

TABLE 3

REMISSION INDICES FOR ANIMALS INNOCULATED WITH A431 CELLS AND TREATED WITH 225 OR C225

| EXP | TREATMENT | # REMISSIONS/ TOTAL* | REMISSION INDEX** |
|---|---|---|---|
| 1 | 225 | 1/6 | 0.17 |
|   | PBS | 0/4 | 0 |
| 2 | 225 | 1/9 | 0.11 |
|   | C225 | 4/9 | 0.44 |
|   | PBS | 0/4 | 0 |
| 3 | C225 | 4/10 | 0.40 |
|   | PBS | 0/3 | 0 |
| 4 | C225:1 | 8/8 | 1.0 |
|   | C225:0.5 | 5/8 | 0.63 |
|   | C225:0.25 | 1/8 | 0.13 |
|   | PBS | 0/4 | 0 |

*Tumor free animals/total number of surviving animals. Differences in the number of animals presented are the result of mice dying during the five week course of the various treatment regimens, and these were not included in the statistical analysis.
**The Remission Index (RI) is defined as the fraction of mice that were tumor free on the day when the PBS control mice and test animals with large tumors were euthanized. A complete remission at the 0.25 mg dose level showed a subsequent recurrance of tumor (day 47).

Example III-2

Inhibition of Growth of Established Human Prostatic Carcinoma Xenografts in Nude Mice

Example 1H-2 A

FACS Analysis of C225 Binding to DU 145. PC-3 and LNCaP

The relative expression levels of EGF receptor on DU 145, PC-3 and LNCaP cells was determined by FACS analysis. Cells were grown to near confluency in complete medium, removed from the flasks with non-enzymatic dissociation buffer (Sigma), and resuspended at $5-10 \times 10^5$ per tube in 100 ul of cold H-BSA (Hanks balanced salt solution containing 1% BSA). Ten micrograms C225 or an irrelevant myeloma-derived human IgG1 (Tago, Burlingame Calif.) were added to the tubes and incubated on ice for 60 minutes. After washing with cold H-BSA, goat anti-human IgG conjugated to FITC (Tago, Burlingame Calif.) was added for an additional 30 minutes on ice. Cells were washed 2 times with cold H-BSA, resuspended in 1 ml of H-BSA, and analyzed using a Coulter Epics Elite cell sorter (Coulter, Hialeah Fla.). Baseline flurorescence was determined using the FITC-labelled secondary antibody alone and non-specific flurorescence was defined by the irrelevant isotype control. Data is presented as the Mean Fluroescence Intensity (MFI), which is an indirect measure of antigen density. MFI is defined as the mean channel fluorescence multiplied by the percentage of positive cells for each sample.

Example III-2B

Phosphorylation Assays on PC-3, DU 145, and LNCaP Cells

Phosphorylation assays were performed on PC-3, DU 145, and LNCaP cells to determine if the EGF receptors expressed by these cells were functional and inhibited by C225. Assays and Western blot analysis were performed as previously described by Gill et al., Nature 293, 305–307 (1981). Briefly, DU 145, PC-3, and LNCaP cells were grown to 90% confluency in complete medium and then starved in DMEM-0.5% calf serum 24 hours prior to experimentation. Cells were stimulated with EGF in the presence or absence of C225 for 15 minutes at room temperature. Monolayers were then washed with the ice cold PBS containing 1 mM sodium orthovanadate. Cells were lysed and subjected to SDS PAGE followed by Western blot analysis. The phosphorylation patterns were determined by probing the blot with a monoclonal antibody to phosphotyrosine (UBI, Lake Placid N.Y.) followed by detection using the ECL method (Amersham).

Example III-2C

Animal Studies

Athymic nude mice (nu/nu; 6–8 weeks old males; Charles River Labs, Wilmington Mass.) were innoculated subcutaneously in the right flank with $10^6$ DU 145 in 0.2 ml of Hank's balanced salt solution mixed with 0.2 ml of matrigel. Mice were observed until tumors were visible (about 14–20 days post challenge) and had reached an average volume of about 100 mm$^3$. Animals were weighed and randomly divided into treatment groups (10 animals per group). Antibody therapy, which included twice weekly intraperitoneal injections of 0.5 mg of C225 over 5 weeks, was begun. Control animals received injections of PBS. Preliminary studies established that there was no significant difference between the growth of DU 145 xenografts in animals treated with polyclonal, DU 145-absorbed human IgG compared to PBS. Tumors were measured two times per week and volumes calculated using the following formula: $\pi/6 \times$larger diameter$\times$(smaller diameter)$^2$. Animals were followed for at least 3 weeks following the final antibody injection (8 weeks after the start of therapy), at which time control animals were euthanized. Tumor free animals and mice with small tumors were followed for an additional 2–3 months. Statistical analysis of tumor growth in each study was determined with a two tailed Student's T-test using the computer program SigmaStat (Jandel, San Rafael Calif.). A p value of <0.05 was considered significant.

Example III-3

Biological Activity of Peptides Containing CDR Regions of 225

This example demonstrates that peptides constructed using 225-CDR sequences had biological activity against cell lines that express EGF receptors. A series of six peptides were generated with the following sequences:

Heavy Chain
   CDR-1 NYGVH (SEQ ID NO: 1)
   CDR-2 GVIWSGGNTDYNTPFTSR (SEQ ID NO: 2)
   CDR-3 RALTYYDYEFAYW (SEQ ID NO: 99)

Light Chain
   CDR-1 RASQSIGTNIH (SEQ NO: 100)
   CDR-2 YASESIS (SEQ ID NO: 101)
   CDR-3 QQNNWP (SEQ ID NO: 102)

These peptides were dissolved in PBS at a concentration of 1 mg/ml. A431 cells were plated at 1000 cells per well in 96 well plates. Peptides were added at various concentrations. The chimeric C225 antibody and an irrelevant, isotype-matched immunoglobulin were used as a positive and negative U 1 s, respectively. Plates were incubated for 72 hours at 37° C. and pulsed overnight with $^3$H-thymidine. Cells were harvested and counted in a liquid scintillation counter. Percent inhibition is defined as the decrease in 3-H thymidine incorporation of antibody or peptide treated cells compared to cells grown in the absence of antibody or peptide.

Figure 5:
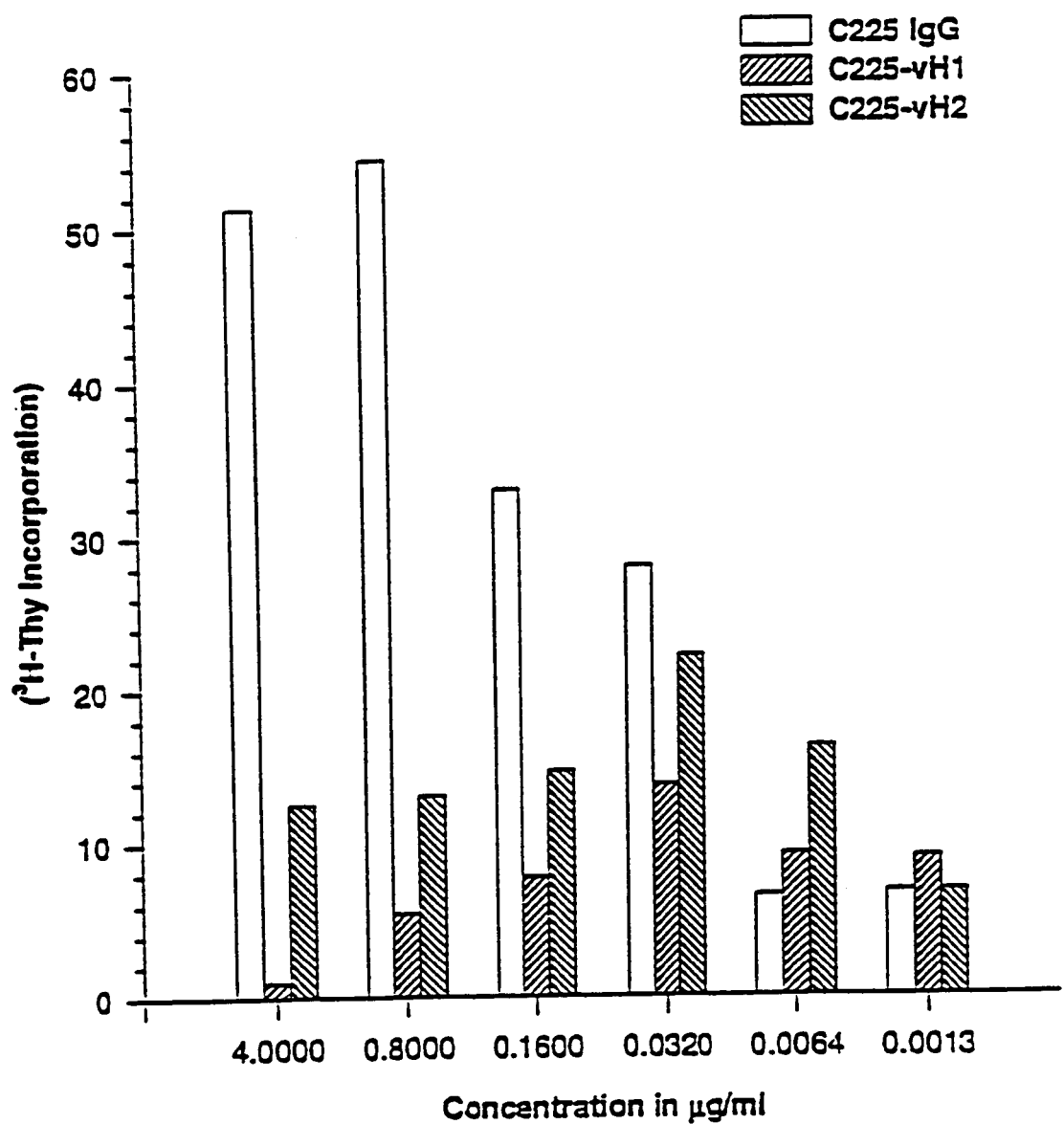
FIG. 5. Inhibition of A431 cells by C225 and by heavy chain CDR-1 and heavy chain CDR-2 of monoclonal antibody 225

As can be seen in FIG. 5, A431 cells are inhibited by C225 and by heavy chain CDR-1 and heavy chain CDR-2 of monoclonal antibody 225. In contrast, isotype-matched irrelevant antibody and U 1 peptide did not inhibit A431 cells. These results indicate that heavy chain CDR-1 and -2 are able to inhibit the growth of A431 cells by interfering with the binding of ligand to the EGFR.

Example III-4

Biological Activity of C225-Doxorubicin Conjugate (C225-DOX)

Figure 6:
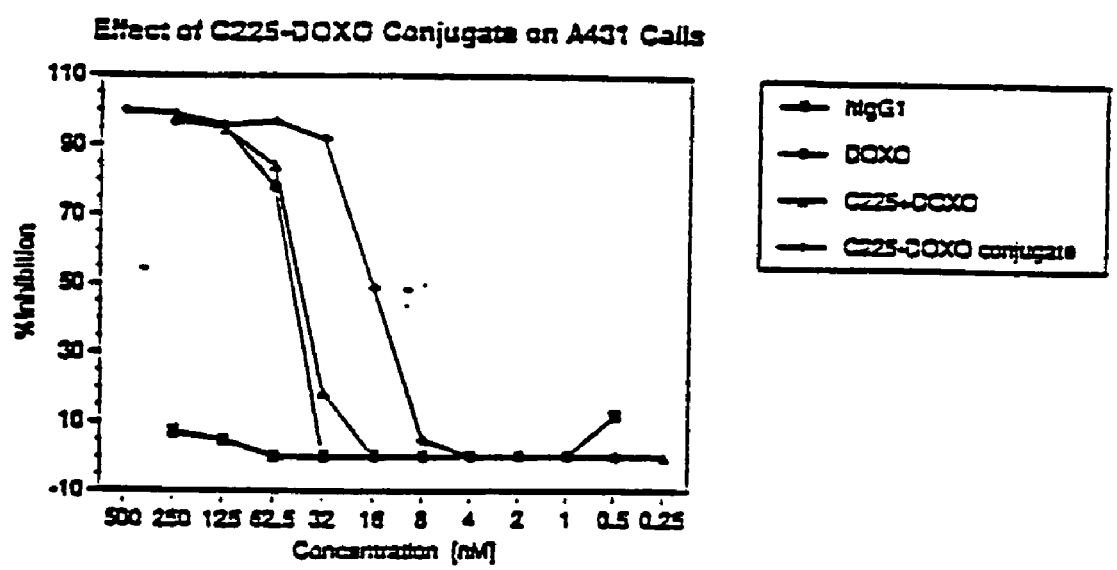
FIG. 6. Inhibition by C225-Doxorubicin conjugate of A431 cells in vivo as a function of concentration.

The biological activity of C225-DOX was evaluated in vitro using EGFR expressing cell lines A431, KB and MDA-468 as well as EGFR non-expressing cell lines Molt-4 and SK-MEL-28. EGF receptor expression was verified by FACS analysis using C225 and C225-DOX conjugate. Assays were conducted over a 72 h incubation period using $^3$[H]-thymidine and WST-1 as a read out. In all assays with EGFRc expressing cell lines, i.e., A431, KB and MDA-468 cells, C225-DOX exhibited high inhibition of cell proliferation when compared to no treatment or hIgG1 U 1s. Comparisons of equimolar concentrations of C225-DOX with doxorubicin alone or mixtures of C225 and doxorubicin showed a 4–5 fold higher inhibition using the C225-DOX conjugate. Inhibition of cell proliferation by C225DOX was also seen in EGFRc nonexpressing cell lines at higher doses. The C225-DOX inhibition in EGFRc-negative cell lines was 5–15 fold lower than EGFRc-positive cell lines and was similar to inhibition seen with equimolar concentrations of doxorubicin alone. Representative results are shown in FIG. 6 for activity of C225-DOX on 431 cells.

Example IV

Humanization of M225

Example IV-1 Abbreviations

Dulbecco's Modified Eagles Medium (DMEM); Foetal Calf Serum (FCS); ribonuceic acid (RNA); messenger RNA (mRNA); deoxyribonucleic acid (DNA); double-stranded DNA (ds-DNA); polymerase chain reaction (PCR); enzyme linked immunoabsorbant assay (ELISA); hour (hr); minute (min); second (sec); human cytomegalovirus (HCMV); polyadenylation (poly(A)$^+$); immunoglobulin (IgG); monoclonal antibody (mAb); complementarity determining region (CDR); framework region (FR); Tris-borate buffer (TBE); bovine serum albumin (BSA); phosphate buffered saline (PBS); room temperature (RT); nanometre (nm); epidermal growth factor receptor (EGFR);

Example IV-2

Materials

Media components and all other tissue culture materials are obtained from Life Technologies (UK), except for FCS which is purchased from JRH Biosciences (USA). The RNA isolation kit is obtained from Stratgene (USA) while the 1$^{st}$ strand cDNA synthesis kit is purchased from Pharmacia (UK). All the constituents and equipment for the PCR-reactions, including AmpliTaq®DNA polymerase, are purchased from Perkin Elmer (USA). The TA Cloning® kit is obtained from Invitrogen (USA) and the Sequenase® DNA sequencing kit is purchased from Amersham International (UK). Agarose (UltraPure™) is obtained from Life Technologies (UK). The Wizard™ PCR Preps DNA Purification Kit, the Magic™ DNA Clean-up System and XL1 Blue competent cells are purchased from Promega Corporation (USA). All other molecular biological products are purchased from New England Biolabs (USA). Nunc-Immuno Plate MaxiSorp™ immunoplates are obtained from Life Technologies (UK). Both the goat anti-human IgG, Fcγ fragment specific, antibody and the goat anti-human IgG (H+ L)/horseradish peroxidase conjugate are purchased from Jackson ImmunoResearch Laboratories Inc. (USA). TMB substrate A and substrate B are obtained from Kirkegaard-Pery (USA). All other products for both ELISAs are obtained from Sigma (UK). Microplate Manager® data analysis software package is purchased from Bio-Rad (UK). The molecular modelling package QUANTA is obtained from the Polygen Corporation (USA) and the IRIS 4D workstation is purchased from Silicon Graphics (USA).

Example IV-3

PCR Cloning and Sequencing of the Mouse Variable Region Genes

The mouse M225 hybridoma cell line is grown, in suspension, using DMEM supplemented with 10% (v/v) FCS, 50 Units/ml penicillin/50 μg/ml streptomycin and 580 μg/l ml L-glutamine. Approximately $10^8$ viable cells are harvested, while the supernatant from the hybridoma cells is assayed by ELISA to confirm that they are producing a mouse antibody. From the $10^8$ cells total RNA is isolated using a RNA Isolation kit according to the manufacturers instructions. The kit uses a guanidinium thiocyanate phenol-chloroform single step extraction procedure as described by Chomczynski and Sacchi (6). Also following the manufacturers instructions, a 1$^{st}$ Strand cDNA Synthesis kit is employed to produce a single-stranded DNA copy of the M225 hybridoma mRNA using the NotI-(dT)$_{18}$— primer supplied in the kit. Approximately 5 μg of total RNA is used in a 33 μl final reaction volume. The completed reaction mix is then heated to 90° C. for 5 min, to denature the RNA-cDNA duplex and inactivate the reverse transcriptase, before being chilled on ice.

To PCR-amplify the mouse variable region genes the method described by Jones and Bendig (7) is followed. Essentially, two series of degenerate primers, one series designed to anneal to the leader sequences of mouse kappa light chain genes (i.e. MKV1–11; Table 4) and one series designed to anneal to the leader sequences of mouse heavy chain genes (i.e. MHV1–12; Table 5), are used in conjunction with primers designed to anneal to the 5'-end of the mouse kappa light chain constant region gene (MKC; Table 4) and the 5'-end of the mouse yl heavy chain constant region gene (MHCG1; Table 5), respectively, to PCR-clone the mouse variable region genes of the M225 antibody. Separate reactions are prepared for each of the MKV and MHV degenerate primers, with their respective constant region primer. The PCR-reaction tubes are loaded into a Perkin Elmer 480 DNA thermal cycler and cycled (after an initial melt at 94° C. for 1.5 min) at 94° C. for 1 min, 50° C. for 1 min and 72° C. for 1 min over 25 cycles. At the completion of the last cycle a final extension step at 72° C. for 10 min is carried out before the reactions are cooled to 4° C. Except for between the annealing (50° C.) and extension (72° C.) steps, when an extended ramp time of 2.5 min is used, a 30 sec ramp time between each step of the cycle is employed.

20 μl aliquots from each PCR-reaction are run on agarose gels to determine which have produced a PCR-product of the correct size. Those PCR-reactions that do appear to amplify full-length variable domain genes are repeated to produce independent PCR-clones and thereby minimise the effect of PCR-errors. 6 μl aliquots of those PCR-products of the correct size are directly cloned into the pCR™II vector, provided by the TA Cloning® kit, and transformed into INVαF' competent cells as described in the manufacturers instructions. Colonies containing the plasmid, with a correctly sized insert, are identified by PCR-screening the colonies using the pCR™II Forward and pCR™II Reverse oligonucleotide primers described in Table 6 according to the method of Güssow and Clackson (8). The putative positive clones identified are finally double-stranded plasmid DNA sequenced using the Sequenase®DNA Sequencing kit according to the method of Redston and Kem (9).

Example IV-4

Construction of Chimeric Genes

The cloned mouse leader-variable region genes are both modified at the 5'- and 3'-ends using PCR-primers to create restriction enzyme sites for convenient insertion into the expression vectors, a Kozak sequence for efficient eukaryotic translation of the mRNA encoding the respective immunoglobulin chains (10) and a splice-donor site for the correct RNA splicing of the variable and constant region genes. A HindIII site is added to the 5'-end of both mouse variable region genes, however, different restriction sites are attached to the 3'-end of the mouse variable region genes i.e. a BamHI site at the 3'-end of the VH gene and a XhaI site at the 3'-end of the VK gene.

PCR-reactions are prepared according to the method for the construction of chimeric genes in Kettleborough et al. (11), using the primers $C225V_H5'$ and $C225V_H3'$ for the heavy chain, and $C225V_K5'$ and $C225V_K3'$ for the kappa light chain (Table 7). Following an initial melting step at 94° C. for 90 sec the mixes are PCR-amplified at 94° C. for 2 min and 72° C. for 4 min over 25 cycles. This two step PCR-cycle, as opposed to the more usual three step cycle, is possible because each of the primers is designed to anneal to the template DNA over 24 bases which allows them to anneal at the relatively high temperature of 72° C. A 30 sec ramp time is used between each step and at the end of the last cycle, the PCR-reactions are completed with a final extension step at 72° C. for 10 min before cooling to 4° C. The PCR-products are column purified using a Wizard™PCR Preps DNA Purification kit according to the manufacturers instructions, digested with the appropriate restriction enzymes, as is plasmid pUC19, and separated on a 1% agarose/TBE buffer (pH8.8) gel. The heavy and kappa light chain variable region genes are excised from the agarose gel and purified using a Wizard PCR Preps DNA Purification kit. The pUC19 is also excised from the agarose gel and purified using the Magic™DNA Clean-up System as per the manufacturers instructions. The heavy and kappa light chain variable region genes are then separately ligated into the purified pUC 19 to produce plasmids $PUC-C225V_H$ and $PUC-C225V_K$, respectively, and transformed into XL1Blue competent cells. Putative positive colonies containing the appropriate plasmid are then identified by PCR-screening, using oligonucleotide primers RSP and UP (Table 6) and finally ds-DNA sequenced both to confirm the introduction of the sequence modifications and also to prove that no unwanted changes to the DNA sequence have occured as a consequence of the PCR-reactions.

To modify the signal peptide sequence at the 5'-end of the kappa light chain variable region PCR-mutagenesis is used, according to the protocol described by Kettleborough et al. (11). PCR-primers $C225V_K5'sp$ and $C225V_K3'SP$ (Table 7) are used on $PUC-C225V_K$ template DNA to create the modified gene ($C225V_Ksp$) using the modified two step PCR amplification protocol. The PCR-product is then column purified before digesting both the purified PCR-product and $PUC-C225V_K$ with HindIII and PstI. The PCR-fragment and the plasmid DNA are then agarose gel-purified, ligated together and cloned to create plasmid $PUC-C225V_Ksp$. As before, putative positive transformants are identified via a PCR-screen (using the RSP and UP primers) and then ds-DNA sequenced to confirm both the presence of the modified signal peptide and the absence of PCR-errors.

The adapted mouse kappa light and heavy chain leader-variable region genes are then directly inserted, as a HindIII-BamHI fragment in the case of the mouse $V_H$ and as a HindIII-XbaI fragment in the case of the mouse VK, into vectors designed to express chimeric light and heavy chains in mammalian cells. These vectors contain the HCMV enhancer and promoter to drive the transcription of the immunoglobulin chain, a MCS for the insertion of the immunoglobulin variable region gene, a cDNA clone of the appropriate human kappa light or heavy chain constant region, a synthetic poly(A)$^+$ sequence to polyadenylate the immunoglobulin chain mRNA, an artificial sequence designed to terminate the transcription of the immunoglobulin chain, a gene such as dhfr or neo for selection of transformed stable cell lines, and an SV40 origin of replication for transient DNA replication in COS cells. The human kappa light chain mammalian expression vector is called pKN 100 (FIG. 11) and the human γ1 heavy chain mammalian expression vector is called pG1D105 (FIG. 12). Putative positive colonies are both PCR-screened, using primers HCMVi and New.HuK for the chimeric kappa light chain vector and primers HCMVi and HuCγ1 for the chimeric heavy chain vector (Table 6), and undergo restriction analysis to confirm the presence of the correct insert in the expression vector constructs. The new constructs containing the mouse variable region genes of the M225 antibody are called $pKN100-C^{225}V_K$ (or $pKN100-C225V_Ksp$) and $pG1D105-C225V_H$, respectively.

Example IV-5

Molecular Modelling of Mouse M225 Antibody Variable Regions

To assist in the design of the CDR-grafted variable regions of the H225 antibody, a molecular model of the variable regions of the mouse M225 antibody is built. Modelling the structures of well-characterized protein families like immunoglobulins is achieved using the established method of modelling by homology. This is done using an IRIS 4D workstation running under the UNIX operating system, the molecular modelling package QUANTA and the Brookhaven crystallographic database of solved protein structures (12).

The FRs of the M225 variable regions are modelled on FRs from similar, structurally-solved immunoglobulin variable regions. While identical amino acid side chains are kept in their original orientation, mismatched side chains are substituted using the maximum overlap procedure to maintain chi angles as in the original mouse M225 antibody. Most of the CDRs of the M225 variable regions are modelled based on the canonical structures for hypervariable loops which correspond to CDRs at the structural level (13–16). However, in cases such as CDR3 of the heavy chain variable region, where there are no known canonical structures, the CDR loop is modelled based on a similar loop structure present in any structurally-solved protein. Finally, in order to relieve unfavourable atomic contacts and to optimize Van der Waals and electrostatic interactions, the model is subjected to energy minimization using the CHARMm potential (17) as implemented in QUANTA.

The FRs from the light chain variable region of M225 antibody are modelled on the FRs from the Fab fragment of mouse monoclonal antibody HyHel-10 (18). The FRs from the heavy chain variable region are modelled on the FRs from the Fab fragment of mouse monoclonal antibody D1.3 (19). Those amino acid side chains which differ between the mouse M225 antibody and the variable regions upon which the model is based are first substituted. The light chain of Fab HyHel-10 antibody is then superimposed onto the light chain of D1.3 by matching residues 35–39, 43–47, 84–88 and 98–102, as defined by Kabat et al., (20). The purpose of this is to place the two heterologous variable regions, i.e. the HyHel-10-based kappa light chain variable region and the D1.3-based heavy variable region, in the correct orientation with respect to each other.

CDR1 (L1) of the light chain variable region of mAb M225 fits into the L1 canonical group 2, as proposed by Chothia et al. (14), except for the presence of an isoleucine, instead of the more usual leucine, at canonical residue position 33. However, this substitution is considered too conservative to merit significant concern in assigning a canonical loop structure to this hypervariable loop. The L1 loop of mouse Fab HyHel-10 is identical in amino acid length and matches the same canonical group—with a leucine at position 33—as the L1 loop of M225 mAb. Consequently this hypervariable loop is used to model the L1 loop of M225 kappa light chain variable region. Similarly, CDR2 (L2) and CDR3 (L3) of the M225 mAb both match their respective canonical group 1 loop structures. In addition, the corresponding hypervariable loop structures of the HyHel-10 Fab fragment are also both group 1. Accordingly, the L2 and L3 loops of the M225 kappa light chain variable region are modelled on L2 and L3 of Fab HyHel-10.

Likewise, CDR1 (H1) and CDR 2 (H2) hypervariable loops of the heavy chain variable region of mAb M225 both fit their respective canonical group 1 loop structures as defined by Chothia et al. (14). Moreover, the corresponding H1 and H2 hypervariable loops of mouse D1.3 Fab fragment also match their respective canonical group 1 loop structures. Consequently, as with the light chain, these hypervariable loops are modelled on the H1 and H2 loops of the heavy variable region upon which the model is based. To identify a matching loop structure to the CDR3 (H3) hypervariable loop of the heavy chain variable region of M225 the Brookhaven database is searched for a loop of identical length and similar amino acid sequence. This analysis found that the H3 loop of the mouse Fab 26/9 (21) exhibited the closest match to the H3 loop of M225 mAb and is consequently used as the basis for this hypervariable loop in the mouse M225 variable region model. After adjusting the whole of the model for obvious steric clashes it is finally subjected to energy minimization, as implemented in QUANTA, both to relieve unfavourable atomic contacts and to optimize van der Waals and electrostatic interactions.

Example IV-6

Design of the Reshaped Human H225 Antibody Variants

The first step in designing the CDR-grafted variable regions of the H225 antibody is the selection of the human light and heavy chain variable regions that will serve as the basis of the humanized variable regions. As an aid to this process the M225 antibody light and heavy chain variable regions are initially compared to the consensus sequences of the four subgroups of human kappa light chain variable regions and the three subgroups of human heavy chain variable regions as defined by Kabat et al. (20). The mouse M225 light chain variable region is most similar to the consensus sequences of both human kappa light chain subgroup I, with a 61.68% identity overall and a 65.00% identity with the FRs only, and subgroup m, with a 61.68% identity overall and a 68.75% identity with the FRs only. The mouse M225 heavy chain variable region is most similar to the consensus sequence for human heavy chain subgroup II with a 52.10% identity overall and a 57.47% identity between the FRs alone. This analysis is used to indicate which subgroups of human variable regions are likely to serve as good sources for human variable regions to serve as templates for CDR-grafting, however, this is not always the case due to the diversity of individual sequences seen within some of these artificially constructed subgroups.

For this reason the mouse M225 variable regions are also compared to all the recorded examples of individual sequences of human variable regions publically available. With respect to human antibody sequences, the mouse M225 light chain variable region is most similar to the sequence for the human kappa light chain variable region from human antibody LS7'CL (22)—which is not related to the mouse L7'CL sequence. The kappa light chain variable region of human LS7'CL is a member of subgroup III of human kappa light chain variable regions. The overall sequence identity between the mouse M225 and human LS7'CL light chain variable regions is calculated to be 64.42% overall and 71.25% with respect to the FRs alone. The mouse M225 heavy chain variable region is most similar to the sequence for the human heavy chain variable region from human antibody 38P1'CL (23). Surprisingly, the heavy chain variable region of human 38P1'CL is a member of subgroup III and not subgroup II of the human heavy chain variable regions. The overall sequence identity between the mouse M225 and human 38P1'CL heavy chain variable regions is calculated to be 48.74% while the identity between the FRs alone is 58.62%. Based on these comparisons, human LS7'CL light chain variable region is selected as the human FR donor template for the design of reshaped human M225 light chain variable region and human 38P1'CL heavy chain variable region is selected as the human FR donor template for the design of reshaped human M225 heavy chain variable region.

As is commonly seen, the human light and heavy chain variable regions that are selected for the humanization of the M225 antibody are derived from two different human antibodies. Such a selection process allows the use of human variable regions which display the highest possible degree of similarity to the M225 variable regions. In addition, there are many successful examples of CDR-grafted antibodies based on variable regions derived from two different human antibodies. One of the best studied examples is reshaped human CAMPATH-1 antibody (24). Nevertheless, such a strategy also requires a careful analysis of the interdomain packing residues between the kapp light chain and heavy chain variable regions. Any mis-packing in this region can have a dramatic affect upon antigen binding, irrespective of the conformation of the CDR loop structures of the reshaped human antibody. Consequently, the amino acids located at the $V_K/V_H$ interface, as defined by Chothia et al. (25), are checked for unusual or rare residues. Any residues so identified are then considered for mutagenesis to an amino acid more commonly seen at the specific residue position under investigation.

The second step in the design process is to insert the M225 CDRs, as defined by Kabat et al. (20), into the selected human light and heavy chain variable region FRs to create a simple CDR-graft. It is usual that a mouse antibody that is humanized by a simple CDR-graft in this way, will show little or no binding to antigen. Consequently, it is important to study the amino acid sequences of the human FRs to determine if any of these amino acid residues are likely to adversely influence binding to antigen, either directly through interactions with antigen, or indirectly by altering the positioning of the CDR loops.

This is the third step of the design process where decisions are made as to which amino acids in the human donor FRs should be changed to their corresponding mouse M225 rsidues in order to achieve good binding to antigen. This is a difficult and critical step in the humanization procedure and it is at this stage that the model of the M225 variable regions becomes most useful to the design process. In conjunction with the model the following points are now addressed.

It is of great importance that the canonical structures for the hypervariable loops (13–16) are conserved. It is therefore crucial to conserve in the humanized H225 variable regions any of the mouse FR residues that are part of these canonical structures. It is also helpful to compare the sequence of the M225 antibody to similar sequences from other mouse antibodies to determine if any of the amino acids are unusual or rare as this may indicate that the mouse residue has an important role in antigen binding. By studying the model of the M225 variable regions, it is then possible to make a prediction as to whether any of these amino acids, or any other residues at particular positions, could or could not influence antigen binding. Comparing the individual human donor sequences for the kappa light and heavy chain variable regions to the consensus sequence of human variable regions subgroups to which the donor sequences belong, and identifying amino acids that are particularly unusual is also important. By following this design process a number of amino acids in the human FRs are identified that should be changed from the amino acid present at that position in the human variable region to the amino acid present at that position in the Mouse M225 variable region.

Table 8 describes how the first version (225RK$_A$) of the reshaped human H225 kappa light chain variable regions is designed. There is only one residue in the reshaped human FRs where it is considered necessary to change the amino acid present in the human FRs to the amino acid present in the original mouse FRs. This change is at position 49 in FR2, as defined by Kabat et al. (20). The tyrosine found in human LS7'CL kappa light chain variable region is changed to a lysine, as found in mouse M225 kappa light chain variable region. From the model it appears that the lysine in M225 is located close to CDR3 (H3) of the heavy chain variable region and may be interacting with it. The residue is also positioned adjacent to CDR2 (L2) of the kappa light chain variable region and is rarely seen at this location amongst the members of mouse kappa light chain subgroup V, as defined by Kabat et al (20), to which the M225 kappa light chain variable region belongs. For these reasons it is felt prudent to conserve the mouse lysine residue in 225RK$_A$.

A second version is also made of the reshaped human kappa light chain (225RK$_B$) which reverses the FR2 modification made in 225RK$_A$, by replacing the lysine at position 49 with the original human tyrosine amino acid. Consequently, this version of the reshaped human kappa light chain will contain no mouse residues in the FRs whatsoever.

With respect to the design of reshaped human H225 heavy chain variable region, Table 9 shows the first version (225RH$_A$). In all there are eight residues in the reshaped human FRs where it is considered necessary to change the amino acid present in the human 38P1'CL FRs to the amino acids present in the original mouse M225 FRs (i.e. A24V, T28S, F29L, S30T, V48L, S49G, F67L and R71K). At positions 24, 28, 29 and 30 in FR1 the amino acid residues as present in the mouse sequence are retained in the reshaped human H225 heavy chain variable region because they represent some of the canonical residues important for the H1 hypervariable loop structure (14). Since canonical residues are so critical for the correct orientation and structure of hypervariable loops that they are generally always conserved in the reshaped variable region. Moreover, residue positions 24–30 are considered part of the H1 hypervariable loop itself and so are even more critical to the correct conformation and orientation of this loop and justifying their conservation even more strongly. Similarly, residue position 71 in FR3 is another position in the heavy chain variable region which has been identified by Chothia et al. (14) as one of the locations important for the correct orientation and structure of the H2 hypervariable loop and, as such, is one of the canonical amino acids of CDR2. Consequently, the lysine in the mouse will replace the arginine in the human at this residue position. At positions 48 and 49 in FR2 and 67 in FR3, the valine, serine and phenylalanine residues (respectively) present in the human 38P1'CL VH sequence are changed to leucine, glycine and leucine (respectively) as present in the mouse M225 VH sequence. This descision is made on the basis of the model which shows that all three residues are buried underneath the H2 loop and so could influence the conformation of the hypervariable loop and hence interfere with antigen binding. These are then the mouse residues conserved in the first version of the reshaped human H225 heavy chain variable region.

Version B of the reshaped human H225 heavy chain variable region (225RH$_B$) incorporates all the substitutions made in 225RH$_A$ and, in addition, contains a further mouse residue. At position 41 in FR2 the human threonine residue is replaced by proline which is invariably seen at this position in the mouse subgroup IB and is also very commonly seen in human subgroup III. In contrast, threonine is not usually seen at this location in the human subgroup III (only 11/87 times) and from the model it is appears that the residue is located on a turn located on the surface of the M225 V$_H$ region. What effect this may have on hypervariable loop structures is unclear, however, this version of the reshaped human H225 heavy chain variable region should clarify this.

Version C of the reshaped human H225 heavy chain variable region (225RH$_C$) incorporates all the substitutions made in 225RH$_A$ and, in addition, contains a further two mouse residues located at position 68 and 70 in FR3. From the model of the mouse M225 variable region, both the serine at position 68 and the asparagine at position 70 appear to be on the surface and at the edge of the antigen binding site. Since there is a possibility that either or both amnio acids could directly interact with EGFR, both the threonine at position 68 and the seine at position 70 in the human FRs are replaced with the corresponding mouse residues in 225RH$_C$.

Version D of the reshaped human H225 heavy chain variable region (225RH$_D$) simply incorporates all the mouse FR substitutions made in 225RH$_A$, 225RH$_B$ and 225RH$_C$ to determine the combined effect of these changes.

Version E of the reshaped human H225 heavy chain variable region (225RH$_E$) incorporates all the substitutions made in 225RH$_A$ and, in addition, incorporates another residue change at position 78 in FR3. From the model there is some evidence to suggest that the mouse amino acid (valine) at position 78 could influence the conformation of the H1 hypervariable loops from its location buried underneath CDR1. Consequently, the human residue (leucine) is replaced by the mouse amino acid in 225RH$_E$.

Example IV-7

Construction of the Humanized Antibody Variable Region Genes

The construction of the first version of the reshaped human H225 V$_K$ region (225RK$_A$) is carried out essentially as described by Sato et al. (26). In essence, this involves annealing PCR-primers encoding FR modifcations (Table 10) onto a DNA template of the chimeric C$^{225}$ V$_K$ gene using the two step PCR-amplification protocol to synthesize the reshaped human variable region gene. As a consequence, the FR DNA sequence of the chimeric C225V$_K$ is modified by the primers to that of the reshaped human kappa light chain variable region gene 225RK$_A$. The newly synthesized reshaped variable region gene, following column purification, is digested with HindIII and XbaI, agarose gel-purified and subcloned into pUC 19 (digested and agarose gel-purified in an identical manner). The new plasmid construct, pUC-225RK$_A$, is then transformed into XL1Blue competent cells. Putative positive clones are identified by PCR-screening (using primers RSP and UP) and then finally ds-DNA sequenced, both to confirm their integrity and discount the presence of PCR-errors. From the confirmed postive clones an individual clone is selected and directly inserted, as a HindIII-XbaI fragment, into the human kappa light chain mammalian expression vector (pKN100) to create the plasmid pKN100-225RK$_A$. The integrity of this vector construct is confirmed via PCR-screening (using primers HCMVi and New.Huκ) and restriction digest analysis.

Version B of the reshaped human H225 V$_K$ (225RK$_B$) is constructed using oligonucleotide primers 225RK$_B$.K49Y and APCR40 (Table 11). A 100 μl PCR-reaction mix comprising 65.5 μl of sterile distilled/deionized water, 5 μl of 2 ng/μl plasmid pUC-225RK$_A$ template DNA, 10 μl of 10×PCR buffer II, 6 μl of 25 mM MgCl$_2$, 2 μl each of the 10 mM stock solutions of dNTPs, 2.5 μl aliquots (each of 10 μM) of primers 225RK$_B$.K49Y and APCR40 and 0.5 ill of AmpliTaq®DNA polymerase is overlayed with 50 μl of mineral oil and loaded into a DNA thermal cycler. The PCR-reaction is PCR-amplified, using the two step protocol over 25 cycles, and the PCR-product column purified before it is cut with MscI. Plasmid pUC-225RKA is also cut with MscI and both the digested PCR product and the plasmid fragment are agarose gel-purified. The PCR-product is then cloned into pUC-225RK$_A$, to create pUC-225RK$_B$, before being transformed into XL1Blue competent cells. Putative positive transformant are first identified, using primers 225RK$_B$.K49Y and UP in a PCR-screening assay, and then confirmed via ds-DNA sequencing. A selected individual clone is finally sublconed into pKN100 to produce the plasmid pKN100–225RK$_B$, whose correct construction is confirmed both by using primers HCMVi and New.Huκ (Table 6) in a PCR-screening assay and restriction analysis.

The construction of the first version of the reshaped human H225 V$_H$ region (225RH$_A$) is also carried out essentially as described by Sato et al. (26). In the case of the reshaped human 225RH$_A$ gene this involves annealing PCR-primers (Table 12) onto both a DNA template of a prevoiusly humanized mAb, to create the 5'-half of the reshaped human kappa light chain variable region gene, and the chimeric C225V$_H$ gene, to synthesize the 3'-half of the reshaped human kappa light chain variable region gene. Again, the two step PCR-amplification protocol is used and the reshaped variable region gene created is cloned into pUC19 vector, as an agarose gel-purified HindIII-BamHI fragment, to create plasmid pUC-225RH$_A$. Putative positive clones identified by PCR-screening (using primers RSP and UP) are finally ds-DNA sequenced both to confirm the DNA sequence and prove the absence of PCR-errors. From the confirmed positive clones an individual clone is selected and directly inserted, as a HindIII-BamHI fragment, into the human γ1 heavy chain mammalian expression vector pG1D105 to create plasmid pG1D105–225RH$_A$. The construction of this plasmid is then confirmed both by using primers HCMVi and γAS (Table 6) in a PCR-screening assay and restriction analysis.

Versions B of the reshaped human H225 V$_H$ (225RH$_B$) is synthesized in a two step PCR-mutagenesis procedure in the following manner. Two separate 100 μl PCR-reaction mixes are first prepared by combining 65.5 μl of sterile distilled/deionized water, 5 μl of 2 ng/μl plasmid pUC-225RH$_A$ template DNA, 10 μl of 10×PCR buffer II, 6 μl of 25 mM MgCl$_2$, 2 μl each of the 10 mM stock solutions of dNTPs, 2.5 #l aliquots (each of 10 μM) of primers APCR10 and 225RH$_B$.T41P-AS in the first PCR-reaction, and primers APCR40 and 225RH$_B$.T41P—S in the second PCR-reaction (Table 13), and finally 0.5 μl of AmpliTaq®DNA polymerase. Each of the two PCR-reaction mixes are overlayed with 50 μl of mineral oil, loaded into a DNA thermal cycler and PCR-amplified using the two step protocol over 25 cycles. The two PCR-products are then agarose gel-purified, to separate them from any template DNA remaining in the PCR-reaction, before being resuspended in 50 μl of distilled/deionized water and their concentration determined.

In a second PCR-reaction 20 pmol aliquots of each of the two PCR-products from the first PCR-reaction (equivalent to 8 μl of the APCR10/225RH$_B$.T41P-AS PCR product and 10 μl of the APCR40/225RH$_B$.T41P—S PCR-product) are added to 57.5 μl of sterile distilled/deionized water, 10 μl of 10×PCR buffer II, 6 μl of 25 mM MgCl$_2$, 2 μl each of the 10 mM stock solutions of dNTPs and 69.5 μl of AmpliTaq®DNA polymerase. This PCR-reaction is overlayed with mineral oil and PCR-amplified using the two step protocol over 7 cycles only. A third PCR-reaction is then prepared comprising 1 μl of the product of the second PCR-reaction 69.5 μl of sterile distilled/deionized water, 10 μl of 10×PCR buffer II, 6 al of 25 mM MgCl$_2$, 2 μl each of the 10 mM stock solutions of dNTPs, 2.5 μl aliquots (each of 10 μM) of the nested primers RSP and UP and 0.5 μl of AmpliTaq®DNA polymerase. The PCR-reaction is overlayed with mineral oil and amplified using the two step protocol for a final 25 cycles. This PCR-product is then column purified, isolated as an agarose gel purified HindIII-BamHI fragment, subcloned into HindIII-BamHI digested and agarose gel-purified plasmid pUC 19, and finally transformed into XL1 Blue competent cells. Putative positive transformants are first identified and then confirmed as described previously. A selected individual clone is then sublconed into pG1D105 to produce the plasmid pG1D10$^5$–225RH$_B$—which is confirmed using primers HCMVi and γAS (Table 6) in a PCR-screening assay and by restriction analysis.

Version C of the reshaped human H225 V$_H$ (225RH$_B$) is synthesized in a similar manner to 225RK$_C$. A 100 μl PCR-reaction mix containing 65.5 μl of sterile distilled/deionized water, 5 μl of 2 ng/μl plasmid pUC-225RH$_A$ template DNA, 10 μl of 10×PCR buffer II, 61 of 25 mM MgCl$_2$, 2 μl each of the 10 mM stock solutions of dNTPs, 2.5 μl aliquots (each of 10 M) of primers APCR40 and 225RH$_C$.T68S/S70N (Table 13) and 0.5 μl of AmpliTaq®DNA polymerase. The PCR-reaction is overlayed with mineral oil PCR-amplified, using the two step protocol over 25 cycles, and column purified prior to digestion with SalI and BamHI. Plasmid pUC-225RH$_A$ is also cut with with SalI and BamHI and both the digested PCR product and the plasmid are agarose gel-purified. The PCR-product is then cloned into pUC-225RH$_A$, to create pUC-225RH$_C$, before being transformed into XL1 Blue competent cells. Putative positive transformant are first identified, using primers RSP and UP in a PCR-screennig assay, and later confirmed via ds-DNA sequencing. A selected individual clone is then sublconed into pG1D105 to produce the plasmid pGD105–225RH$_C$. The correct construction of this vector finally proven both by using primers HCMVi and γAS (Table 6) in a PCR-screening assay and restriction analysis.

Version D of the reshaped human H225 V$_H$ (225RH$_D$) is a product of the changes incorporated into versions B and C of the reshaped human heavy chain of H225 antibody. Fortuitously, it is possible to amalgamate the changes made to these heavy chain variable region genes by digesting both pUC-225RH$_B$ and pUC-225RH$_C$ with SalI and BamHI. The 2.95 kb vector fragment from pUC-225RH$_B$ and the approximately 180 bp insert fragment from pUC-225RH$_C$ are then agarose gel-purified before being ligated together and transformed into XL1Blue competent cells. Positive transformant are identified and ds-DNA sequenced before a selected individual clone is sublconed into pG1D105 to produce the plasmid pG1D105-225RH$_D$. The correct construction of this vector is finally confirmed as described previously.

Version E of the reshaped human H225 V$_H$ (225RH$_E$) is a derivative of 225RH$_A$ and is synthesized in an identical manner to 225RH$_C$ using primers APCR40 and 225RH$_E$.L78V (Table 13). A selected 225RH$_E$ clone from plasmid pUC-225RH$_E$ is then subcloned into pG1D105 to produce the vector pG1D10$^5$–225RH$_E$—the correct construction of which is proven in the usual manner.

Example IV-8

Transfection of DNA into COS Cells

The method of Kettleborough et al. (11) is followed to transfect the mammalian expression vectors into COS cells.

Example IV-9

Protein A Purification of Recombinant 225 Antibodies

Both the chimeric C225 antibody and the various reshaped human H225 antibody constructs are protein A purified according to the protocol described in Kolbinger et al. (27).

Example IV-10

Mouse Antibody ELISA

Each well of a 96-well Nunc-Immuno Plate MaxiSorp™ immunoplate is first coated with 100 μl aliquots of 0.5 ng/μl goat anti-mouse IgG (γ-chain specific) antibody, diluted in coating buffer (0.05 M Carbonate-bicarbonate buffer, pH 9.6), and incubated overnight at 4° C. The wells are blocked with 200 μl/well of mouse blocking buffer (2.5% (w/v) BSA in PBS) for 1 hr at 37° C. before being washed with 200 μl/well aliquots of wash buffer (PBS/0.05% (v/v) tween-20) three times. 100 μl/well aliquots of the experimental samples (i.e. harvested media from the M225 hybridoma cell line—spun to remove cell debris) and 1:2 sample dilutions, diluted in sample-enzyme conjugate buffer (0.1 M Tris-HCl (pH 7.0), 0.1 M NaCl, 0.02% (v/v) tween-20 and 0.2% (w/v) BSA), are now dipensed onto the immunoplate. In addition, a purified mouse IgG standard, serially diluted 1:2 from a starting concentration of 1000 ng/ml, is also loaded onto the immunoplate. The immunoplate is incubated at 37° C. for 1 hr and washed three times with 200 μl/well of wash buffer. 100 μl of goat anti-mouse IgG/horseradish peroxidase conjugate, diluted 1000-fold in sample-enzyme conjugate buffer, is now added to each well, following which the immunoplate is incubated at 37° C. for 1 hr before it is washed as before. 100 μl aliquots of TMB peroxiodase substrate A:peroxidase substrate B (1:1) are now added to each well and incubated for 10 min at RT in the dark. The reaction is halted by dispensing 50 μl of 1 N H$_2$SO$_4$ into each well. The optical density at 450 nm is finally determined using a Bio-Rad 3550 microplate reader in conjunction with Microplate Manager™.

Example IV-11

Quantification of Whole Human γ1/κ. Antibody via ELISA

Each well of a 96-well Nunc-Immuno Plate MaxiSorp™ immunoplate is first coated with 100 μl aliquots of 0.4 ng/μl goat anti-human IgG (Fcγ fragment specific) antibody, diluted in coating buffer (0.05 M Carbonate-bicarbonate buffer, pH 9.6), and incubated overnight at 4° C. The wells are then each blocked with 200 μl of human blocking buffer (2% (w/v) BSA in PBS) for 2 hr at RT before being washed with 200 μl/well aliquots of wash buffer (PBS/0.05% (v/v) tween-20) three times. 100 μl/well aliquots of the experimental samples (i.e. harvested COS cell supernatents-spun to remove cell debris) and 1:2 sample dilutions, diluted in sample-enzyme conjugate buffer (0.1 M Tris-HCl (pH 7.0), 0.1 M NaCl, 0.02% (v/v) tween-20 and 0.2% (w/v) BSA), are now dipensed onto the immunoplate. In addition, a purified human γ1/κ antibody, which is used as a standard and serially diluted 1:2, is also loaded onto the immunoplate. The immunoplate is incubated at 37° C. for 1 hr before being washed with 200 μl/well of wash buffer three times. 100 μl of goat anti-human kappa light chain/horseradish peroxidase conjugate, diluted 5000-fold in sample-enzyme conjugate buffer, is added to each well, following which the immunoplate is incubated at 37° C. for 1 hr before it is washed as before. The remainder of the protocol is identical to the mouse antibody ELISA.

Example IV-12

A431 Cell ELISA for the Detection of EGFR Antigen Binding

The procedure is based upon the one provided by ImClone Systems Inc. to determine the relative binding affinity of the recombinant 225 antibody constructs, to EGFR expressed on the surface of A431 cells. The A431 cells are plated onto a 96-well flat bottomed tissue culture plate and incubated overnight in DMEM media with 10% (v/v) FBS at 37° C. and 5% $CO_2$. The following day the media is removed, the cells are washed once in PBS and then fixed with 100 µl/well of 0.25% (v/v) gluteraldehyde in PBS. This is removed and the plate is washed again in PBS before it is blocked with 200 µl/well of 1% (w/v) BSA in PBS for 2 hr at 37° C. The blocking solution is removed and 100 µl/well aliquots of the experimental samples (i.e. harvested COS cell supematents—spun to remove cell debris) and 1:2 sample dilutions thereof (diluted in 1% (w/v) BSA in PBS) are dispensed onto the tissue culture plate. In addition, 80 µl/well aliquots of purified human γ1/κ antibody, which is used as a standard and serially diluted 1:5 from a starting concentration of 20 µg/ml, is also loaded onto the plate. The plate is incubated at 37° C. for 1 hr and then washed with 200 µl/well of 0.5% (v/v) tween-20 in PBS, three times. 100 µl of goat anti-human IgG (H+ L)/horseradish peroxidase conjugate, diluted 5000-fold in 1% (w/v) BSA in PBS, is now added to each well, following which the plate is incubated at 37° C. for 1 hr before being washed first with 200 µl/well of 0.5% (v/v) tween-20 in PBS (three times) and then distilled deionized water (twice). The remainder of the protocol is identical to the mouse antibody ELISA.

Example IV-13

Cloning and Sequencing of the Variable Regions of the M225 Antibody

The presence of mouse antibody in the media from the M225 hybridoma cells at the point of harvesting the cells for RNA purification was proven using the mouse antibody ELISA. Following $1^{st}$ strand synthesis the single stranded cDNA template was PCR-amplified with two series of degenerate primers, one series specific for the kappa light chain signal peptide/variable region genes (Table 4) and the second series specific for the heavy chain signal peptide/variable region genes (Table 5). Using these primers both the $V_K$ gene and the $V_H$ gene of the M225 antibody were successfully PCR-cloned from the M225 hybridoma cell line.

The M225 kappa light chain variable region gene was PCR-cloned, as an approximately 416 bp fragment, using primers MKV4 (which annealed to the 5' end of the DNA sequence of the kappa light chain signal peptide) and MKC (designed to anneal to the 5' end of the mouse kappa constant region gene). Likewise the M225 heavy chain variable region gene was PCR-cloned, as an approximately 446 bp fragment, using the MHV6 (which annealed to the 5' end of the DNA sequence of the heavy chain signal peptide) and MHCG1 (designed to anneal to the 5' end of the $CH_1$ domain of the mouse γ1 heavy chain gene) primers.

To minimize the possibility of introducing errors into the wild-type sequences of the mouse M225 variable region genes, either caused by AmpliTaq® DNA polymerase itself or changes introduced by reverse transcriptase (which has an error frequency approximately $\frac{1}{10}$ that of AmpliTaq®), a strict protocol was followed. At least two separate PCR-products, each from a different total RNA preparation and subsequent $1^{st}$ strand cDNA synthesis reaction, were PCR-cloned and then completely DNA sequenced on both DNA strands for both the kappa light chain and heavy chain variable region genes of M225 mAb.

From DNA sequence analysis of several individual clones from each of these PCR-reactions the mouse M225 antibody $V_K$ and $V_H$ genes were determined as shown in FIGS. 13 and 14, respectively. The amino acid sequences of the M225 $V_K$ and $V_H$ regions were compared with other mouse variable regions and also the consensus sequences of the subgroups that the variable regions were subdivided into in the Kabat database (20). From this analysis the M225 $V_K$ region was found to most closely match the consensus sequence of mouse kappa subgroup V, with an identity of 62.62% and a similarity of 76.64% to the subgroup. However, the kappa light chain variable region also displayed a close match to mouse kappa subgroup III with a 61.68% identity and a 76.64% similarity to its consensus sequence. When only the FRs of the M225 kappa light chain variable region (i.e. without the amino acids in the CDRs) were compared to mouse subgroups III and V the identity increased to 66.25% for both subgroups while the similarity rose to 78.75% for subgroup III and to exactly 80.00% for subgroup V. Similar analysis of the M225 VH region found that it exhibited the closest match to the consensus sequence of mouse heavy chain subgroup IB in the Kabat database (20). Identity between the mouse heavy chain variable region amino acid sequence of M225 and the consensus sequence of subgroup IB was measured at 78.15% while the similarity was calculated to be 84.87%, with no other consensus sequence coming even remotely near these values. These results confirm that the mouse M225 variable regions appear to be typical of mouse variable regions.

Example IV-14

Construction and Expression of Chimeric C225 Antibody

The PCR-products from the two PCR-reactions prepared to construct the C225 $V_K$ and $V_H$ genes were separately subcloned into pUC 19 as HindIII-BamHI fragments and then PCR-screened to identify putative positive transformants. Those transformants so identified were then ds-DNA sequenced, to confirm their synthesis, and then subcloned into their respective mammalian expression vectors. The DNA and amino acid sequences of the chimeric C225 kappa light chain and heavy chain variable regions are shown in FIGS. 15 and 16, respectively. Once the integrity of the expression vectors had also been confirmed, by PCR-screening and restriction analysis to confirm the presence of the correct insert, the vectors were co-transfected into COS cells. After 72 hr incubation, the medium was collected, spun to remove cell debri and analysed by ELISA for antibody production and binding to EGFR. Unfortunately, no chimeric antibody could be detected in the supernatant of the COS cell co-transfections.

An analysis of the leader sequence of C225V$_K$ established that it was unusual, compared to the leader sequences of other kappa light chain variable regions in mouse kappa light chain subgroups III and V (20). To try and find a more suitable leader squence, the Kabat database was analysed to identify an individual kappa light chain which both matched C225V$_K$ amino acid sequence and whose signal peptide sequence was known. This search identified the kappa light chain of mouse antibody L7'CL (28) which exhibited a 94.79% identity and a 94.79% similarity to the C225V$_K$ region and a perfect match with resepct to FR1, which play an important role in the excision of the signal peptide during secretion. The amino acid sequence of the L7'CL kappa light chain signal peptide (i.e. MVSTPQFLVFLLFWIPASRG (SEQ ID NO: 110)) displays all the characteristics thought important in a such a signal sequence—such as a hydrophobic core—and so it was decided to replace the signal peptide of the PCR-cloned 225V$_K$ with this new sequence. Another point of interest was that the differences between the M225V$_K$ and the L7'CL signal peptides nearly all occured at its 5'-end where the MKV4 primer annealed (i.e. the first 33 bases which is eqivualent to the first 11 amino acids of the signal peptide) when the M225V$_K$ gene was originally PCR-cloned. Thus, these differences could well be primer induced errors in the DNA sequence of the signal peptide. PCR-mtuagenesis of the C225V$_K$ template produced an approximately 390 bp product. The HindIII-PstI digested and purified fragment was then subcloned into identically digested and agarose gel-purified plasmid PUC-C225V$_K$ and transformed into XL1 Blue competent cells. Putative positive transformants were identified and then ds-DNA sequenced. The C225V$_K$sp gene (FIG. 17y was subcloned into pKN100 and the resulting expression vector (pKN100-C225V$_K$sp) PCR-screened and restriction digested to confirm the presence of the correct insert This vector was finally co-transfected into COS cells with pG1D105-C225V$_H$ and after 72 hr incubation, the medium was collected, spun to remove cell debri and analysed by ELISA for antibody production and binding to EGFR This time chimeric C225 antibody was detected in the supernatent of the COS cell co-transfections at an approximate concentration of 150 ng/ml and this antibody bound to EGFR in the cell ELISA. FIG. 18 shows a typical example of one such experiment.

Example IV-15

Construction and Expression of the Reshaped H225 Antibody (225RK$_A$/225RH$_A$)

The construction of the first version of the reshaped human H225 kappa light chain variable region (225RK$_A$) produced an approximately 416 bp product that was then subcloned into pUC 19 as a HindIII-BamHI fragment. Putative positive transformants were identified using the PCR-screening assay and then ds-DNA sequenced. The 225RK$_A$ gene (FIG. 19) was subcloned into pKN 100 and the resulting expression vector (pKN100-225RK$_A$) PCR-screened and restriction digested to confirm the presence of the correct insert. Likewise, the construction of the first version of the reshaped human H225 heavy chain variable region (225RH$_A$) produced an approximately 446 bp product which was then subcloned into pUC 19 as a HindII-BamHI fragment. Putative positive transformants were again identified in the PCR-screen and then ds-DNA sequenced. The 225RH$_A$ gene (FIG. 20) was subcloned into pG1D105 and the resulting expression vector (pG1D105-225RH$_A$) PCR-screened and restriction digested to confirm the presence of the correct insert.

These vectors were then co-transfected together into COS cells and after 72 hr incubation, the medium was collected, spun to remove cell debri and analysed by ELISA for antibody production and binding to EGFR. The concentration of reshaped human antibody in the COS cell supernatents was slightly higher than those following transient expression of the C225 chimeric antibody (approximately 200 ng/ml). In addition, a significant level of binding to EGFR was shown in the cell ELISA. FIG. 8 shows a typical example of one such experiment which appears to show that the reshaped human H225 antibody (225RK$_A$/225RH$_A$) bound to EGFR expressed on the surface of A431 cells with about 65% of the relative affinity of the chimeric C225 antibody.

The amino acid sequences of the two versions of the kappa light chain reshaped human H225 variable regions constructed are shown in FIG. 21, while the amino acid sequences of the five versions of the heavy chain reshaped human H225 variable regions constructed are shown in FIG. 22.

Example IV-16

REFERENCES

1. Mendelsohn, J. (1988). In: Waldmann, H. (ed). *Monoclonal antibody therapy*. Prog. Allergy Karger, Basel, p147.
2. Aboud-Pirak, E., Hurwitz, E., Pirak, M. E., Bellot, F., Schlessinger, J., and Sela, M. (1988). *J. Natl. Cancer Inst.* 80:1605.
3. Masui, H., Kawamoto, T., Sato, J. D., Wolf, B., Sato, G., and Mendelsohn, J. (1984). *Cancer Research* 44:1002.
4. Mueller, B. M., Romerdahl, C. A., Trent, J. M., and Reisfeld, R. A. (1991). *Cancer Research* 51:2193.
5. Rodeck, U., Herlyn, M., Herlyn, D., Molthoff, C., Atkinson, B., Varello, M., Steplewski, Z., and Koprowski, H. (1987). *Cancer Research* 47:3692.
6. Chomczynski, P., and Sacchi, N. (1987). *Anal. Biochem.* 162:156.
7. Jones, S. T., and Bendig, M. M. (1991). *Bio/Technology* 9:88.
8. Güssow, D., and Clackson, T. (1989). *Nucleic Acids Res.* 17:4000.
9. Redston, M. S., and Kern, S. E. (1994). *Biotechniques* 17:286.
10. Kozak, M. (1987). *J. Mol. Biol.* 196:947.
11. Kettleborough, C. A., Saldanha, J., Heath, V. J., Morrison, C. J., and Bendig, M. M. (1991). *Protein Eng.* 4:773.
12. Bernstein, F. C., Koetzle, T. F., Willliams, G. J., Meyer, E. F., Brice, M. D., Todgers, J. R., Kennard, O., Shimanouchi, T. and Tasumi, M. (1977). *J Mol. Biol.* 112:535.
13. Chothia, C., and Lesk, A. M. (1987). *J. Mol. Biol.* 196:901.
14. Chothia, C., Lesk, A. M., Tramontano, A., Levitt, M., Smith-Gill, S. J., Air, G., Sheriff, S., Padlan, E. A., Davies, A., Tulip, W. R., Colman, P. M., Spinelli, S., Alzari, P. M., and Poljak, R. J. (1989). *Nature* 34:877.
15. Tramontano, A., Chothia, C., and Lesk, A. M. (1990). *J. Mol. Biol.* 215:175.
16. Chothia, C., Lesk, A. M., Gherardi, E., Tomlinson, I. M., Walter, G., Marks, J. D., Llewelyn, M. B., and Winter, G. (1992). *J. Mol. Biol.* 227:799.

17. Brooks, B. R., Bruccoleri, R. E., Olafson, B. D., States, D. J., Swaminathan, S., and Karplus, M. (1983). *J. Comp. Chem.* 4:187.
18. Padlan, E. A., Silverton, E. W., Sheriff, S., Cohen, G. H., Smith-Gill, S. J., and Davies, D. R. (1989). *Proc. Nat. Acad. Sci. USA* 86:5938.
19. Fischmann, T. O., Bentley, G. A., Bhat, T. N., Boulot, G., Mariuzza, R. A., Phillips, S. E. V., Tello, D. and Poljak, R. J. (1991) *J. Biol. Chem.* 266:12915.
20. Kabat, E. A., Wu, T. T., Perry, H. M., Gottesman, K. S., and Foeller, C. (1991). *Sequences of proteins of immunological interest*, Fifth Edition, U.S. Department of Health and Human Services, U.S. Government Printing Office.
21. Schulze-Gahmen, U., Rini, J. M., and Wilson, I. A. (1993). *J. Mol. Biol.* 234:1098.
22. Silberstein, L. E., Litwin, S., and Carmack, C. E. (1989). *J. Exp. Med* 169: 1631.
23. Schroeder Jr., H. W., Hillson, J. L., and Perlmutter, R. M. (1987). *Science* 238:791.
24. Riechmann, L., Clark, M., Waldmann, H., and Winter, G. (1988). *Nature* 322:21.
25. Chothia, C., Novotny, J., Bruccoleri, R., and Karplus, M. (1985). *J. Mol. Biol.* 186:651.
26. Sato, K., Tsuchiya, M., Saldanha, J., Koishihara, Y., Ohsugi, Y., Kishimoto, T., and Bendig, M. M. (1993). *Cancer Research* 53:851.
27. Kolbinger, F., Saldanha, J., Hardman, N., and Bendig, M. M. (1993). *Protein Eng.* 6:971.
28. Pech, M., Hochtl, J., Schnell, H., and Zachau, H. G. (1981). *Nature* 291:668.

Example IV-17

TABLES

Table 4. Degenerate and specific PCR-primers used in the cloning of the M225 kappa light chain variable region genes (SEQ ID NOS: 31–42).

Table 5. Degenerate and specific PCR-primers used in the cloning of the M225 heavy chain variable region genes (SEQ ID NOS: 43–55).

Table 6. Primers for PCR screening transformed colonies (SEQ ID NOS: 56–64).

Table 7. Primers for constructing chimeric C225 antibody kappa light chain and heavy chain variable region genes and also for modifying the signal peptide sequence of the C225 antibody kappa light chain (SEQ ID NOS: 65–70).

Table 8. Alignment of amino acid sequences leading to the design of the first version of the reshaped human H225 antibody kappa light chain variable region (225RK$_A$).

Table 9. Alignment of amino acid sequences leading to the design of the first version of the reshaped human H225 antibody heavy chain variable region (225RH$_A$).

Table 10. Primers for constructing reshaped human antibody H1225 kappa light chain variable region gene 225RK$_A$ (SEQ ID NOS: 71–80).

Table 11. Primers for constructing reshaped human antibody H225 kappa light chain variable region gene 225RK$_B$ (SEQ ID NOS: 81–82).

Table 12. Primers for constructing reshaped human antibody H225 heavy chain variable region gene 225RH (SEQ ID NO: 83–89).

Table 13. Primers for constructing reshaped human antibody H225 heavy chain variable region genes 225RH$_B$, 225RH$_C$, 225RH$_D$ and 225RH$_E$. (SEQ ID NOS: 90–97)

TABLE 4

Degenerate and specific PCR-primers used in the cloning of the M225 kappa light chain variable region genes.

| Name | Sequence (5'→ 3') |
|---|---|
| MKV1[a](30 mer) | ATGAAGTTGCCTGTTAGGCTGTTGGTGCTG |
| MKV2(30 mer) | ATGGAGACAGACACACTCCTGCTATGGGTG<br>       T             T |
| MKV3(30 mer) | ATGAGTGTGCTCACTCAGGTCCTGGCGTTG<br>                            G |
| MKV4(33 mer) | ATGAGGGCCCCTGCTCAGTTTTTTGGCTTCTTG<br>      A          A C     AA |
| MKV5(30 mer) | ATGGATTTTCAGGTGCAGATTATCAGCTTC<br>        A            T |
| MKV6(27 mer) | ATGAGGTGCCCTGTTCAGTTCCTGGGG<br>     T TT  C G C T   A |
| MKV7(31 mer) | ATGGGCATCAAGATGGAGTCACAGACCCAGG<br>            T                   TTTT T |
| MKV8(31 mer) | ATGTGGGGACCTTTTTTCCCTTTTTCAATTG<br>       T  G    C AA |
| MKV9(25 mer) | ATGGTATCCACACCTCAGTTCCTTG<br>      G   T G |
| MKV10(27 mer) | ATGTATATATGTTTGTTGTCTATTTCT |
| MKV11(28 mer) | ATGGAAGCCCCAGCTCAGCTTCTCTTCC |
| MKC[b](20 mer) | ACTGGATGGTGGGAAGATGG |

[a]MKV indicates primers that hybridize to leader sequences of mouse kappa light chain variable region genes.
[b]MKC indicates the primer that hybridizes to the mouse kappa constant region gene.

TABLE 5

Degenerate and specific PCR-primers used in the cloning of the M225 heavy chain variable region genes.

| Name | Sequence (5' → 3') |
|---|---|
| MHV1[a](27 mer) | ATGAAATGCAGCTGGGGCATCTTCTTC<br>                         G |
| MHV2(26 mer) | ATGGGATGGAGCTGTATCATGTTCTT<br>                A       CC |
| MHV3(27 mer) | ATGAAGTTGTGGTTAAACTGGGTTTTT<br>           A |
| MHV4(25 mer) | ATGAACTTTGGGCTCAGCTTGATTT<br>       G      T     G |
| MHV5(30 mer) | ATGGACTCCAGGCTCAATTTAGTTTTCCTT |
| MHV6(27 mer) | ATGGCTGTCCTAGGGCTACTCTTCTGC<br>       T G C    G |
| MHV7(26 mer) | ATGGGATGGAGCGGGATCTTTCTCTT<br>      A     T G    A |
| MHV8(23 mer) | ATGAGAGTGCTGATTCTTTTGTG |
| MHV9(30 mer) | ATGGATTGGGTGTGGACCTTGCTATTCCTG<br>     C            A |
| MHV10(27 mer) | ATGGGCAGACTTACATTCTCATTCCTG |

TABLE 5-continued

Degenerate and specific PCR-primers used in the cloning of the M225 heavy chain variable region genes.

| Name | Sequence (5' → 3') |
|---|---|
| MHV11(28 mer) | ATGGATTTTGGGCTGATTTTTTTTATTG |
| MHV12(27 mer) | ATGATGGTGTTAAGTCTTCTGTACCTG |
| MHCG1[b](21 mer) | CAGTGGATAGACAGATGGGGG |

[a]MHV indicates primers that hybridize to leader sequences of mouse heavy chain variable region genes.
[b]MHCG indicates primers that hybridize to mouse constant region genes.

TABLE 6

Primers for PCR screening transformed colonies

| Name | Sequence (5' → 3') |
|---|---|
| pCR™I Forward Primer(18 mer) | CTAGATGCATGCTCGAGC |
| pCR™II Reverse Primer(21 mer) | TACCGAGCTCGGATCCACTAG |
| RSP(Reverse Sequencing Primer) (24mer) | AGCGGATAACAATTTCACACAGGA |
| UP(Universal Primer)(24 mer) | CGCCAGGGTTTTCCCAGTCACGAC |
| γAS(20 mer) | ACGACACCGTCACCGGTTCG |
| HCMVi(28 mer) | GTCACCGTCCTTGACACGCGTCTCGGGA |
| New.Huκ(25 mer) | GTTGTTTGCGCATAATCACAGGGCA |
| Huκ1(17 mer) | TTGGAGGAGGGTGCCAG |
| 225RK$_B$.K49Y(60 mer) | CAGCAAAGACCTGGCCAGGCTCCAAGGCTTCTCATATATTATGCTTCTGAGTCTATCTCT |

TABLE 7

Primers for constructing chimeric C225 antibody kappa light chain and heavy chain variable region genes and also for modifying the signal peptide sequence of the C225 antibody kappa light chain.

| Name | Sequence (5' → 3') |
|---|---|
| C225V$_H$5'(36 mer) | AAGCTTGCCGCCACCATGGCTGTCTTGGGGCTGCTC |
| C225V$_H$3'(34 mer) | GGATCCACTCACCTGCAGAGACAGTGACCAGAGT |
| C225V$_K$5'(36 mer) | AAGCTTGCCGCCACCATGGTATCCACACCTCAGAAC |
| C225V$_K$3'(40 mer) | TCTAGAAGGATCCACTCACGTTTCAGCTCCAGCTTGGTCC |
| C225V$_K$5'sp(99 mer) | AAGCTTGCCGCCACCATGGTATCCACACCTCAGTTCCTTGTATTTTTGCTTTTCTGGATTCCAGCCTCCAGAGGTGACATCTTGCTGACTCAGTCTCCA |
| C225V$_K$3'sp(21 mer) | AGAGATAGACTCAGAAGCATA |

TABLE 8

Alignment of amino acid sequences leading to the design of the first version of the reshaped human H225 antibody kappa light chain variable region (225RK$_A$).

| Kabat # | FR or CDR | Mouse C225 | Mouse -V | Human -III | Human donor LS7'CL | 225 RK$_A$ | Surface or Buried | Comment |
|---|---|---|---|---|---|---|---|---|
| 1 | 1 | FR1 | D | D | E | E | E | Surface | |
| 2 | 2 | | I | I | I* | I | I | | Canonical AA for L1 loop |
| 3 | 3 | | L | Q | V* | V | V | Surface | [1676] L = 6/270 (& Linked to 10I + 39R + 40T + 41N) in mouse κ-V. L = 1/116 in human -III. |
| | | | [83] | | [1075] | | | | |
| 4 | 4 | | L | M | L | L | L | | L = 18/276 in mouse κ-V. |
| 5 | 5 | | T | T* | T* | T | T | | |
| 6 | 6 | | Q | Q* | Q | Q | Q | | |
| 7 | 7 | | S | S | S* | S | S | | |
| 8 | 8 | | P | P | P* | P | P | | |
| 9 | 9 | | V | S | G | A | A | Surface | [1621] Val not seen in mouse κ-V. V = 1/107 in human -III. |
| | | | [5] | | [466] | | | | |

TABLE 8-continued

Alignment of amino acid sequences leading to the design of the first version of the reshaped human H225 antibody kappa light chain variable region (225RK$_A$).

| | | | | | | | | | |
|---|---|---|---|---|---|---|---|---|---|
| 10 | 10 | | I [185] | S | T* | T [177] | T | Surface | [1396] I = 4/286 (& linked to 3L + 39R + 40T + 41N) in mouse κ-V. Ile not seen in human -III. |
| 11 | 11 | | L | L | L* | L | L | | |
| 12 | 12 | | S | S | S* | S | S | | |
| 13 | 13 | | V [677] | A | L | L [87] | L | Surface | [1616] V = 47/276 in mouse κ-V. V = 17/106 in human -III. |
| 14 | 14 | | S | S | S* | S | S | | |
| 15 | 15 | | P | L | P* | P | P | | P = 26/286 in mouse κ-V. |
| 16 | 16 | | G | G* | G* | G | G | | |
| 17 | 17 | | E | D | E | E | E | | E = 95/276 in mouse κ-V. |
| 18 | 18 | | R | R | R | R | R | | |
| 19 | 19 | | V | V | A | A | A | Buried | V = 10/98 in human -III. |
| 20 | 20 | | S | T | T | T | T | Half-buried | S = 77/299 in mouse κ-V. S = 1/97 in human -III. |
| 21 | 21 | | F [15] | I | L* | L [234] | L | Buried | [1595] F = 5/301 in mouse κ-V. Phe not seen in human -III. |
| 22 | 22 | | S | T | S* | S | S | | S = 116/296 in mouse κ-V. |
| 23 | 23 | FRI | C | C* | C* | C | C | | |
| 24 | 24 | CDR1 | R | R | R | R | R | | |
| 25 | 25 | | A | A* | A* | A | A | | Canonical AA for L1 loop. |
| 26 | 26 | | S | S* | S* | S | S | | |
| 27 | 27 | | Q | Q | Q | Q | Q | | |
| 27A | | | — | D | — | — | — | | |
| 27B | | | — | — | — | — | — | | |
| 27C | | | — | — | — | — | — | | |
| 27D | | | — | — | — | — | — | | |
| 27E | | | — | — | — | — | — | | |
| 27F | | | — | — | — | — | — | | |
| 28 | 28 | | S | D | S | S | S | | |
| 29 | 29 | | I | I | V | V | I | | |
| 30 | 30 | | G | S | S | S | G | | |
| 31 | 31 | | T | N | S | S | T | | |
| 32 | 32 | | N | Y | Y | Y | N | | |
| 33 | 33 | | I | L | L | L | I | | |
| 34 | 34 | CDR1 | H | N | A | A | H | | Packing AA. |
| 35 | 35 | FR2 | W | W* | W* | W | W | | |
| 36 | 36 | | Y | Y | Y* | Y | Y | | Packing AA. |
| 37 | 37 | | Q | Q* | Q | Q | Q | | |
| 38 | 38 | | Q | Q | Q | Q | Q | | Packing AA. |
| 39 | 39 | | R | K | K | R | R | | R = 10/252 (& linked to 3L + 10I + 40T + 41N) in mouse κ-V. |
| 40 | 40 | | T [10] | P | P* | P [1080] | P | Surface | [1301] T = 5/255 (& linked to 3L + 10I + 39R + 41N) in mouse κ-V. Thr not seen in human -III. |
| 41 | 41 | | N [5] | G | G* | G [1009] | G | Surface | [1267] N = 5/246 & linked to 3L + 10I + 39R + 40T) in mouse κ-V. Asn not seen in human -III. |
| 42 | 42 | | G | G | Q | Q | Q | Surface | G = 1/67 in human -III. |
| 43 | 43 | | S | S | A | A | A | Surface | S = 2/66 in human -III. |
| 44 | 44 | | P | P | P* | P | P | | Core packing AA. |
| 45 | 45 | | R | K | R* | R | R | | R = 34/250 in mouse κ-V. (Possible link to AA3, 10, 39–41). |
| 46 | 46 | | L | L | L* | L | L | | Packing AA. |
| 47 | 47 | | L | L* | L* | L | L | | |
| 48 | 48 | | I | I | I* | I | I | | Canonical AA for L2 Loop. |
| 49 | 49 | FR2 | K [19] | Y | Y | Y [1042] | K | Buried | Close to H3 loop & may be interacting with it. (Δ1) [1234] K = 13/249 (& linked to 581) in mouse κ-V. (Possible link to AA3, 10, 39–41.). Lys not seen in human -III. |
| 50 | 50 | CDR2 | Y | Y | G | D | Y | | |
| 51 | 51 | | A | A | A | A | A | | Canonical AA for L2 loop. |
| 52 | 52 | | S | S | S* | S | S | | Canonical AA for L2 loop. |
| 53 | 53 | | E | R | S | N | E | | |
| 54 | 54 | | S | L | R* | R | S | | |
| 55 | 55 | | I | H | A* | A | I | | |

TABLE 8-continued

Alignment of amino acid sequences leading to the design of the first version of the reshaped human H225 antibody kappa light chain variable region (225RK$_A$).

| | | | | | | | | | |
|---|---|---|---|---|---|---|---|---|---|
| 56 | 56 | CDR2 | S | S | T* | T | S | | |
| 57 | 57 | FR3 | G | G* | G* | G | G | | |
| 58 | 58 | | I | V | I* | I | I | | I = 34/232 (& linked to 49K) in mouse κ-V. (Possible link to AA 3, 10, 39–41.) |
| 59 | 59 | | P | P* | P* | P | P | | |
| 60 | 60 | | S | S | D | A | A | Surface | Ser not seen in human -III. |
| 61 | 61 | | R | R* | R* | R | R | | |
| 62 | 62 | | F | F* | F* | F | F | | |
| 63 | 63 | | S | S | S* | S | S | | |
| 64 | 64 | | S | G* | G* | G | S | | Canonical AA for L2 loop. |
| 65 | 65 | | S | S* | S* | S | S | | |
| 66 | 66 | | G | G | G | G | G | | |
| 67 | 67 | | S | S* | S* | S | S | | |
| 68 | 68 | | G | G* | G* | G | G | | |
| 69 | 69 | | T | T | T* | T | T | | |
| 70 | 70 | | D | D | D | D | D | | |
| 71 | 71 | | F | Y | F* | F | F | | Canonical AA for l1 loop. F = 82/243 (& linked to 72T) in mouse κ-V. |
| 72 | 72 | | T | S | T* | T | T | | T = 73/246 (& linked to 71F) in mouse κ-V. |
| 73 | 73 | | L | L | L* | L | L | | |
| 74 | 74 | | S [38] | T | T* | T [837] | T | Half-buried | [1220] S = 29/247 in mouse κ-V. Ser not seen in human -III. |
| 75 | 75 | | I | I* | I* | I | I | | |
| 76 | 76 | | N [68] | S | S* | S [880] | S | Surface | [1211] N = 34/242 in mouse κ-V. N = 2/64 in human -III. S = 113/236 in mouse κ-V. |
| 77 | 77 | | S | N | R | S | S | | |
| 78 | 78 | | V | L | L* | L | L | Buried | V = 67/245 in mouse κ-V. V = 1/165 in human -III. |
| 79 | 79 | | E | E | E | E | E | | |
| 80 | 80 | | S [94] | Q | P | P [166] | P | Surface | [1181] S = 56/243 in mouse κ-V. S = 8/65 in human -III. |
| 81 | 81 | | E | E | E | E | E | | |
| 82 | 82 | | D | D* | D* | D | D | | |
| 83 | 83 | | I [98] | I | F* | F [150] | E | Surface | [1176] Ile not seen in human -III. |
| 84 | 84 | | A | A | A* | A | A | | |
| 85 | 85 | | D | T | V* | V | V | Half-buried | D = 36/243 in mouse κ-V. Asp not seen in human -III. |
| 86 | 86 | | Y | Y* | Y* | Y | Y | | |
| 87 | 87 | | Y | F | Y* | Y | Y | | Packing AA. Y = 109/237 in mouse κ-V. |
| 88 | 88 | FR3 | C | C* | C* | C | C | | Packing AA. |
| 89 | 89 | CDR3 | Q | Q | Q* | Q | Q | | Canonical AA for L3 loop. |
| 90 | 90 | | Q | Q | Q* | Q | Q | | Packing AA. (Unusual AA) |
| 91 | 91 | | N | G | Y | R | N | | |
| 92 | 92 | | N | N | G | S | N | | |
| 93 | 93 | | N | T | S | N | N | | |
| 94 | 94 | | W | L | S | W | W | | |
| 95 | 95 | | P | P | P | P | P | | Canonical AA for L3 loop. |
| 95A | | | — | P | P | — | — | | |
| 95B | | | — | — | L | — | — | | |
| 95C | | | — | — | T | — | — | | |
| 95D | | | — | — | F | — | — | | |
| 95E | | | — | — | G | — | — | | |
| 95F | | | — | — | Q | — | — | | |
| 96 | 96 | | T | R | G | L | T | | Core packing AA. |
| 97 | 97 | CDR3 | T | T* | T | T | T | | Canonical AA for L3 loop. |
| 98 | 98 | FR4 | F | F* | F* | F | F | | Core packing AA. |
| 99 | 99 | | G | G* | G* | G | G | | |
| 100 | 100 | | A | G | Q | G | G | surface | A = 26/215 in mouse κ-V. Ala not seen in human -III. |
| 101 | 101 | | G | G* | G* | G | G | | |
| 102 | 102 | | T | T* | T* | T | T | | |
| 103 | 103 | | K | K* | K | K | K | | |
| 104 | 104 | | L | L* | V | V | V | buried | L = 15/56 in human -III. |
| 105 | 105 | | E | E* | E* | E | E | | |
| 106 | 106 | | L | I | I* | I | I | buried | L = 23/176 in mouse κ-V. L = 1/56 in human -III. |
| 106A | | | — | — | — | — | — | | |
| 107 | 107 | FR4 | K | K* | K* | K | K | | |

TABLE 8-continued

Alignment of amino acid sequences leading to the design of the first version of the reshaped human H225 antibody kappa light chain variable region (225RK$_A$).

| Comparison of AA Variable Region AA Sequences to M225 | Mouse C225 | Mouse κ-V | Human κ-III | Human Donor LS7"CL | 225 RH$_A$ | Comment |
|---|---|---|---|---|---|---|
| PERCENT IDENTITY | 100.0 | 62.62 | 61.68 | 65.42 | 79.44 | Comment: There are 22 amino acid mismatches in the frameworks between |
| FRAMEWORKS ONLY | 100.0 | 66.25 | 68.75 | 71.25 | 72.50 | the variable regions of the reshaped kappa light chain H225RKa and the mouse M225 kappa light chain. |
| PERCENT SIMILARITY | 100.0 | 76.64 | 72.90 | 77.57 | 87.85 | Candidate AA for further mutation include residues aat positions 39–45 |
| FRAMEWORKS ONLY | 100.0 | 80.0 | 80.0 | 82.50 | 83.75 | (which are unusual) and a back mutation at position 49 i.e. K49Y. |

Legend:
(*) invariant residues as defined either by the Kabat consensus sequences i.e. 95% or greater occurrence within Kabat subgroup (Kabat et al., 1991) (in the case of columns 5 and 6) or as part of the canonical structure for the CDR loops (in the case of column 8) as defined by Chothia et al., (1989); (BOLD) positions in Frs and CDRs where the human amino acid residue was replaced by the corresponding mouse residue (UNDERLINE) positions inFrs where human residue differs from the analogous mouse residue number; (δ) numbering of changes in human Frs; (mouse C225) amino acid sequence of the $V_L$ region from chimeric C225 antibody; (mouse -V) consensus sequence of mouse kappa $V_L$ regions from subgroup V (Kabat et al., 1991); (human -III) consensus sequence of human $V_L$ regions from subgroup III (Kabat et al., 1991); (Human Donor LS7'CL) amino acid sequencefrom human LS7'CL antibody (Silberstein, L.E. et al., 1989); (Surface or Buried) position of amino acid in relation to the rest of the residues in both chains of the antibody variable regions; (225RK$_A$) amino acid sequence of the first version of the reshaped human mAB H225 $V_K$ region; (Core packing AA/Packing AA) amino acids located at the $V_L/V_H$ interface as defined by Chothia et al. (1985); (Canonical AA) aminoacids defined by Chothia and Lesk (1987), Chothia et al. (1989), Tramontano et al. (1990) and Chothia et al. (1992) as being important for CDR loop conformation.

TABLE 9

Alignment of amino acid sequences leading to the design of the first version of the reshaped human H225 antibody kappa light chain variable region (225RK$_A$).

| Kabat # | | FR or CDR | Mouse C225 | Mouse IB | Human III | Human donor 38P1 | 225 RH | Surface or Buried | Comment |
|---|---|---|---|---|---|---|---|---|---|
| 1 | 1 | FR1 | Q | Q* | E | E | E | Surface | Q = 13/172 in human III. |
| 2 | 2 | \| | V | V* | V | V | V | | |
| 3 | 3 | \| | Q | Q | Q | Q | Q | | |
| 4 | 4 | \| | L | L* | L* | L | L | | |
| 5 | 5 | \| | K [99] | K* | V | V [499] | <u>V</u> | Surface | [1446] Lys not seen in human III. |
| 6 | 6 | \| | Q | E | E | E | E | Buried | Q = 15/84 (& linked to 13Q + 40S + 80F + 84S + 85N + 89I) in mouse IB. Q = 0/164 in human III. |
| 7 | 7 | \| | S | S* | S* | S | S | | |
| 8 | 8 | \| | G | G* | G* | G | G | | |
| 9 | 9 | \| | P | P* | G* | G | <u>G</u> | Surface | Pro not seen in human III. |
| 10 | 10 | \| | G | G | G | G | G | | |
| 11 | 11 | \| | L | L* | L | L | L | | |
| 12 | 12 | \| | V | V* | V | V | V | | |
| 13 | 13 | \| | Q | A | Q | Q | Q | | |
| 14 | 14 | \| | P | P* | P* | P | P | | |
| 15 | 15 | \| | S | S* | G* | G | <u>G</u> | Surface | Ser not seen in human III. |
| 16 | 16 | \| | Q | Q* | G | G | <u>G</u> | Surface | Gln not seen in human III. |
| 17 | 17 | \| | S | S* | S* | S | S | | |
| 18 | 18 | \| | L | L* | L* | L | <u>L</u> | | |
| 19 | 19 | \| | S | S* | R | R | <u>R</u> | Surface | Ser not seen in human III. |
| 20 | 20 | \| | I | I* | L | L | <u>L</u> | Buried | I = 1/143 in human III. |
| 21 | 21 | \| | T | T* | S* | S | <u>S</u> | Surface | Thr not seen in human III. |
| 22 | 22 | \| | C | C* | C* | C | C | | |
| 23 | 23 | \| | T | T* | A | A | <u>A</u> | Surface | T = 1/128 in human III. |
| 24 | 24 | \| | V | V* | A | A | V | Buried | Canonical AA for H1 loop. V = 9/132 in human III. (δ) |
| 25 | 25 | \| | S | S* | S* | S | S | | |
| 26 | 26 | \| | G | G* | G | G | G | | Canonical AA for H1 loop. |
| 27 | 27 | \| | F | F* | F* | F | F | | Canonical AA for H1 loop. |
| 28 | 28 | \| | S | S* | T | T | S | | Canonical AA for H1 loop. S = 6/104 in human III. (δ2) |
| 29 | 29 | \| | L | L* | F | F | L | | Canonical AA for H1 loop. L = 1/108 in human III. (δ3) |

TABLE 9-continued

Alignment of amino acid sequences leading to the design of the first version of the reshaped human H225 antibody kappa light chain variable region (225RK$_A$).

| | | | | | | | | | |
|---|---|---|---|---|---|---|---|---|---|
| 30 | 30 | FRI | T | T | S | S | T | | Canonical AA for H1 loop. T = 1/103 in human III. (δ4) |
| 31 | 31 | CDR | N | S | S | S | N | | |
| 32 | 32 | \| | Y | Y | Y | Y | Y | | |
| 33 | 33 | \| | G | G | A | D | G | | |
| 34 | 34 | \| | V | V | M | M | V | | Canonical AA for H1 loop. |
| 35 | 35 | \| | H | H | S | H | H | | Packing AA. |
| 35a | | \| | — | x | — | — | | | |
| 35b | | CDR1 | — | S | — | — | | | |
| 36 | 36 | FR2 | W | W* | W* | W | W | | |
| 37 | 37 | \| | V | V | V* | V | V | | Packing AA. |
| 38 | 38 | \| | R | R* | R* | R | R | | |
| 39 | 39 | \| | Q | Q* | Q* | Q | Q | | Packing AA. |
| 40 | 40 | \| | S | P | A | A | A | Half-buried | S = 12/97 (& linked to 6Q + 13Q + 80F + 84S + 85N + 89I) in mouse IB. S = 1/91 in human III. |
| 41 | 41 | \| | P [1223] | P* | P | T [11] | T | Surface | [1382] P = 75/87 in human III. |
| 42 | 42 | \| | G | G* | G* | G | G | | |
| 43 | 43 | \| | K | K* | K* | K | K | | |
| 44 | 44 | \| | G | G* | G* | G | G | | |
| 45 | 45 | \| | L | L* | L* | L | L | | Core packing AA. |
| 46 | 46 | \| | E | E* | E | E | E | | |
| 47 | 47 | \| | W | W* | W* | W | W | | Packing AA. |
| 48 | 48 | \| | L | L* | V | V | L | Buried | L = 2/86 in human III. Underneath H2 loop (δ5) |
| 49 | 49 | FR2 | G [985] | G | S | S [58] | G | Buried | [1390] G = 21/86 in human III. Underneath H2. (δ6) |
| 50 | 50 | CDR2 | V | V | V | A | V | | |
| 51 | 51 | \| | I | I* | I | I | I | | |
| 52 | 52 | \| | W | W* | S | G | W | | |
| 52a | | \| | — | — | G | — | — | | |
| 52b | | \| | — | — | K | — | — | | |
| 52c | | \| | — | — | T | — | — | | |
| 53 | 53 | \| | S | A | D | T | S | | |
| 54 | 54 | \| | G | G | G | A | G | | |
| 55 | 55 | \| | G | G* | G | G | G | | Canonical AA for H2 loop. |
| 56 | 56 | \| | N | S | S | D | N | | |
| 57 | 57 | \| | T | T* | T | T | T | | |
| 58 | 58 | \| | D | N | Y | Y | D | | |
| 59 | 59 | \| | Y | Y* | Y | Y | Y | | |
| 60 | 60 | \| | N | N* | A | P | N | | |
| 61 | 61 | \| | T | S | D | G | T | | |
| 62 | 62 | \| | P | A | S | S | P | | |
| 63 | 63 | \| | F | L | V* | V | F | | |
| 64 | 64 | \| | T | M | K | K | T | | |
| 65 | 65 | CDR2 | S | S* | G* | G | S | | |
| 66 | 66 | FR3 | R | R* | R* | R | R | | |
| 67 | 67 | \| | L | L* | F* | F | L | Buried | Leu not seen in human III. (δ7) |
| 68 | 68 | \| | S | S | T | T | T | Surface | Edge of binding site. Ser not seen in human III. |
| 69 | 69 | \| | I | I* | I* | I | I | | |
| 70 | 70 | \| | N [18] | S | S* | S [662] | S | Surface | [1478] Very edge of binding site. N = 1/107 in mouse IB. N = 1/86 in human III. |
| 71 | 71 | \| | K | K* | R* | R | K | Buried | Canonical AA for H2 loop. Lys is not seen in human III. (δ8) |
| 72 | 72 | \| | D [1344] | D* | D | E [31] | E | Half-buried | [1457] D = 71/85 in human III. |
| 73 | 73 | \| | N | N | N | N | N | | |
| 74 | 74 | \| | S | S* | S | A | A | Surface | S = 75/84 in human III. |
| 75 | 75 | \| | K | K | K | K | K | | |
| 76 | 76 | \| | S[800] | S | N | N | N | Half-buried | S = 8/85 (& possibly linked to 49G) in human III. Conserve if binding poor? |
| 77 | 77 | \| | Q [199] | Q* | T | S [51] | S | Surface | [1419] Gln not seen in human III. |
| 78 | 78 | \| | V | V* | L | L | L | Buried | V = 3/84 in human III. |
| 79 | 79 | \| | F | F* | Y | Y | Y | Half-buried | Phe not seen in human III. |

TABLE 9-continued

*Alignment of amino acid sequences leading to the design of the first version of the reshaped human H225 antibody kappa light chain variable region (225RK$_A$).*

| | | | Mouse C225 | Mouse IB | Human III | Human Donor 38PI | 225 RK$_A$ | Location | Comment |
|---|---|---|---|---|---|---|---|---|---|
| 80 | 80 | | F [24] | L | L* | L [857] | L | Buried | [1490] F = 22/112 (& linked to 6Q + 13Q + 40S + 84S + 85N + 89I) in mouse IB. Phe not seen in human III. |
| 81 | 81 | | K | K* | Q | Q | Q | Surface | K = 22/52 in human III. |
| 82 | 82 | | M | M | M* | M | M | | |
| 82a | 83 | | N | N | N | N | N | | |
| 82b | 84 | | S | S* | S | S | S | | |
| 82c | 85 | | L | L | L | L* | L | | |
| 83 | 86 | | Q [118] | Q | R | R [415] | R | Surface | [1482] Q = 4/93 in human III. |
| 84 | 87 | | S | T | A | A | A | Surface | S = 4/116 (& possibly linked to 6Q + 13Q + 40S + 80F + 85N + 89I) in mouse IB. Ser not seen in human III. |
| 85 | 88 | | N [12] | D | E [1244] | G [9] | G | Surface | [1503] N = 11/116 (& linked to 6Q + 13Q + 40S + 80F + 84S + 89I) in mouse IB. Asn not seen in human III. |
| 86 | 89 | | D | D* | D | D | D | | |
| 87 | 90 | | T | T* | T | T | T | | |
| 88 | 91 | | A | A* | A* | A | A | | |
| 89 | 92 | | I | M | V | V | V | Half-buried | I = 24/113 (& possibly linked to 6Q + 13Q + 40S + 80F + 84S + 85N) in mouse IB. I = 1/94 in human III. |
| 90 | 93 | | Y | Y* | Y* | Y | Y | | |
| 91 | 94 | | Y | Y* | Y* | Y | Y | | Packing AA. |
| 92 | 95 | | C | C* | C* | C | C | | |
| 93 | 96 | | A | A* | A | A | A | | Packing AA. |
| 94 | 97 | | FR3 | R | R | R | R | | Canonical AA for H1 loop. |
| 95 | 98 | CDR3 | A | D | G | S | A | | Packing AA. (Unusual AA) |
| 96 | 99 | | L | R | R | F | L | | |
| 97 | 100 | | T | G | X | S | T | | |
| 98 | 101 | | Y | V | G | E | Y | | |
| 99 | 102 | | Y | x | X | T | Y | | |
| 100 | 103 | | D | R | S | E | D | | |
| 100a | 104 | | Y | Y | L | D | Y | | |
| 100b | 105 | | E | D | S | A | E | | |
| 100c | | | — | P | G | — | — | | |
| 100d | | | — | D | x | — | — | | |
| 100e | | | — | K | Y | — | — | | |
| 100f | | | — | Y | Y | — | — | | |
| 100g | | | — | F | Y | — | — | | |
| 100h | | | — | T | Y | — | — | | |
| 100i | | | — | L | H | — | — | | |
| 100j | | | — | W | Y | — | — | | |
| 100k | 106 | | F | F | F | F | F | | Core packing AA. |
| 101 | 107 | | A | D | D | D | A | | |
| 102 | 108 | CDR3 | Y | Y | Y | I | Y | | |
| 103 | 109 | FR4 | W | W* | W* | W | W | | Core packing AA. |
| 104 | 110 | | G | G* | G* | G | G | | |
| 105 | 111 | | Q | Q* | Q | Q | Q | | |
| 106 | 112 | | G | G* | G* | G | G | | |
| 107 | 113 | | T | T* | T* | T | T | | |
| 108 | 114 | | L [349] | L | L | M [28] | M | | [1020] L = 59/76 in human III. |
| 109 | 115 | | V | V | V* | V | V | | |
| 110 | 116 | | T | T* | T* | T | T | | |
| 111 | 117 | | V | V* | V* | V | V | | |
| 112 | 118 | | S | S* | S* | S | S | | |
| 113 | 119 | FR4 | A | S | S* | S | S | | A = 28/76 in mouse IB. Ala not seen in human III. |

| Comparison of AA Variable Region AA Sequences to M225 | Mouse C225 | Mouse IB | Human III | Human Donor 38PI | 225 RH$_A$ | Comment |
|---|---|---|---|---|---|---|
| PERCENT IDENTITY | 100.0 | 78.15 | 55.46 | 48.74 | 76.47 | There are 26 amino acid mismatches in the FR between the variable regions of the reshaped heavy chain H225RH$_A$ and the mouse M225 heavy chain |
| FRAMEWORKS ONLY | 100.0 | 88.51 | 63.22 | 58.62 | 67.82 | |
| PERCENT SIMILARITY | 100.0 | 84.87 | 71.43 | 67.23 | 84.87 | 225RH$_B$ = 225RH$_A$ + T41P<br>225RH$_C$ = 225RH$_A$ + T68S + S70N |

TABLE 9-continued

Alignment of amino acid sequences leading to the design of the first version of
the reshaped human H225 antibody kappa light chain variable region (225RK$_A$).

| FRAMEWORKS ONLY | 100.0 | 93.10 | 79.31 | 75.86 | 79.31 | 225RH$_D$ = 225RH$_B$ + 225RH$_C$<br>225RH$_E$ = 225RH$_A$ + L78V |
|---|---|---|---|---|---|---|

Legend:
(*) invariant residues as defined either by the Kabat consensus sequences i.e. 95% or greater occurrence within Kabat subgroup (Kabat et al., 1991) (in the case of columns 5 and 6) or as part of the canonical structure for the CDR loops (in the case of column 8) as defined by Chothia et al., (1989); (BOLD) positions in Frs and CDRs where the human amino acid residue was replaced by the corresponding mouse residue (UNDERLINE) positions inFrs where human residue differs from the analogous mouse residue number; (δ) numbering of changes in human Frs; (mouse C225) amino acid sequence of the V$_H$ region from chimeric C225 antibody; (mouse IB) consensus sequence of mouse V$_H$ regions from subgroup IB (Kabat et al., 1991); (human III) consensus sequence of human V$_H$ regions from subgroup III (Kabat et al., 1991); (Human Donors: 38P1) amino acid sequence from human antibody38P1'CL (Schroeder Jr et al. 1987); (Surface or Buried) position of amino acid in relation to the rest of the residues in both chains of the antibody variable regions; (225RH$_A$) amino acid sequence of the first version of the reshaped human mAb H225 V$_H$ region. (Core packing of the first version of the reshaped human mAb H225 V$_H$ region (Core packing AA/Packing AA) amino acids located at the V$_L$/V$_H$ interface asdefined by Chothia et al. (1985); (Canonical AA) amino acids defined by Choithia and Lesk (1987), Chothia et al. (1989), Tramontano et al. (1990) and Chothia et al. (1992) as being important for CDR loop conformation.

TABLE 10

Primers for constructing reshaped human antibody H225 kappa light chain variable region gene 225RK$_A$.

| Name | Sequence (5' → 3') |
|---|---|
| 225RK$_A$.LEAD(88 mer) | CTGGAGACTGAGTCAGTACG ATTTCACTTCTGGAGGCTCG AATCCAGAAAAGCAAAAATA CTTGGTTCTGAGGTGTGGAT ACCATGGT |
| 225RK$_A$.FR1(80 mer) | TCGTACTGACTCAGTCTCCA GCCACCCTGTCTTTGAGTCC AGGAGAAAGAGCCACCCTCT CCTGCAGGGCCAGTCAGAGT |
| 225RK$_A$.FR2a(74 mer) | GAGATAGACTCAGAAGCATA CTTTATGAGAAGCCTTGGAG CCTGGCCAGGTCTTTGCTGA TACCAGTGTATGTT |
| 225RK$_A$.FR3(71 mer) | GGCTTCTCATAAAGTATGCT TCTGAGTCTATCTCTGGAAT CCCTGCCAGGTTTAGTGGCA GTGGATCAGGG |
| 225RK$_A$.FR3a(77 mer) | TTTTGTTGACAGTAATAAAC TGCAAAATCTTCAGGCTCCA CACTGCTGATGGTAAGAGTA AAATCTGTCCCTGATCC |
| 225RK$_A$.CDR3(33 mer) | GATTTTGCAGTTTATTACTG TCAACAAAATAAT |
| 225RK$_A$.FR4a(68 mer) | TCTAGAAGGATCCACTCACG TTTCAGCTCCACCTTGGTCC CTCCACCGAACGTGGTTGGC CAGTTATT |
| 225RK$_A$.V78L(42 mer) | ACTCTTACCATCAGCAGTCT GGAGCCTGAAGATTTTGCAG TT |
| 225RK$_A$.L108I(57 mer) | TCTAGAAGGATCCACTCACG TTTGATCTCCACCTTGGTCC CTCCACCGAACGTGGTT |

TABLE 10-continued

Primers for constructing reshaped human antibody H225 kappa light chain variable region gene 225RK$_A$.

| Name | Sequence (5' → 3') |
|---|---|
| 225RK$_A$.LS7 leader (99 mer) | AAGCTTGCCGCCACCATGGA AGCCCCAGCTCAGCTTCTCT TCCTCTTGCTTCTCTGGCTC CCAGATACCACCGGAGAAAT CGTACTGACTCAGTCTCCA |

TABLE 11

Primers for constructing reshaped human antibody H225 kappa light chain variable region gene 225RK$_B$.

| Name | Sequence (5' → 3') |
|---|---|
| 225RK$_B$.K49Y(60 mer) | CAGCAAAGACCTGGCCAGGC TCCAAGGCTTCTCATATATT ATGCTTCTGAGTCTATCTCT |
| APCR40(25 mer) | CTGAGAGTGCACCATATGCG GTGTG |

TABLE 12

Primers for constructing reshaped human antibody H225 heavy chain variable region gene 225RH$_A$.

| Name | Sequence (5' → 3') |
|---|---|
| 225RH$_A$.FR1(37 mer) | GGTGCAGCTGGTCGAGTCTG GGGGAGGCTTGGTACAG |
| 225RH$_A$.FR1a(50 mer) | GGCTGTACCAAGCCTCCCCC AGACTCGACCAGCTGCACCT CACACTGGAC |
| 225RH$_A$.CDR1a(64 mer) | CCCAGTGTACACCATAGTTA GTTAATGAGAATCCGGGAGAC TGCACAGGAGAGTCTCAGGG ACCC |

TABLE 12-continued

Primers for constructing reshaped human antibody H225 heavy chain variable region gene 225RH$_A$.

| Name | Sequence (5' → 3') |
| --- | --- |
| 225RH$_A$.FR2(63 mer) | TTAACTAACTATGGTGTACACTGGGTTCGCCAGGCTACAGGAAAGGGTCTGGAGTGGCTGGGA |
| 225RH$_A$.FR3a(74 mer) | CTGTTCATTTGCAGATACAGGGAGTTCTTGGCATTTTCCTTGGAGATGGTCAGTCGACTTGTGAAAGGTGTATT |
| 225RH$_A$.FR3(73 mer) | CTCCCTGTATCTGCAAATGAACAGTCTCAGAGCCGGGGACACAGCCGTGTATTACTGTGCCAGAGCCCTCACC |
| 225RH$_A$.FR4a(55 mer) | GGATCCACTCACCTGAAGAGACAGTGACCATAGTCCCTTGGCCCCAGTAAGCAAA |

TABLE 13

Primers for constructing reshaped human antibody H225 heavy chain variable region genes 225RH$_B$, 225RH$_C$, 225RH$_D$ and 225RH$_E$.

| Name | Sequence (5' → 3') |
| --- | --- |
| 225RHB.T41P-S(35 mer) | GGGTTCGCCAGGCTCCAGGAAAGGGTCTGGAGTGG |

TABLE 13-continued

Primers for constructing reshaped human antibody H225 heavy chain variable region genes 225RH$_B$, 225RH$_C$, 225RH$_D$ and 225RH$_E$.

| Name | Sequence (5' → 3') |
| --- | --- |
| 225RHB.T41P-AS(30 mer) | TCCTGGAGCCTGGCGAACCCAGTGTACACC |
| 225RHC.T68S/S70N(46mer) | CACAAGTCGACTGAGCATCAACAAGGAAAATGCCAAGAACTCCCTG |
| 225RHE.L78V(72 mer) | CACAAGTCGACTGACCATCTTCAAGGAAAATGCCAAGAACTCCGTTTATCTGCAAATGAACAGTCTCAGAGC |
| APCR10(25 mer) | TACGCAAACCGCCTCTCCCCGCGCG |
| APCR40(25 mer) | CTGAGAGTGCACCATATGCGGTGTG |
| RSP(Reverse Sequencing Primer)(24mer) | AGCGGATAACAATTTCACACAGGA |
| UP(Universal Primer)(24 mer) | CGCCAGGGTTTTCCCAGTCACGAC |

---

We claim:

1. A first nucleic acid molecule encoding a humanized antibody heavy chain or a fragment thereof wherein the humanized antibody heavy chain comprises a human heavy chain constant region and a human heavy chain variable region, wherein CDR1, CDR2 and CDR3 of the heavy chain are substituted with the corresponding CDRs of monoclonal antibody 225 deposited under ATCC Accession No: HB 11935, and amino acid substitutions consisting at positions 24, 28, 29, 30, 48, 49, 67 and 71 according to the Kabat numbering system; or a second nucleic acid molecule encoding a humanized antibody kappa light chain or a fragment thereof wherein the humanized antibody kappa light chain comprises a human kappa light chain constant region and a human kappa light chain variable region, wherein CDR1, CDR2 and CDR3 of the light chain are substituted with the corresponding CDRs of monoclonal antibody 225, and an amino acid substitution consisting at position 49 according to the Kabat numbering system;

wherein a protein encoded by the first nucleic acid molecule and the second nucleic acid molecule binds to human EGF-receptor.

2. A vector comprising one or both of the first and second nucleic acid molecules of claim 1.

3. A first recombinant DNA comprising the first nucleic acid molecule of claim 1 operably linked to regulatory control sequences which effect expression in a host cell; or a second recombinant DNA comprising the second nucleic acid molecule of claim 1, operably linked to regulatory control sequences which effect expression in a host cell; or a third recombinant DNA comprising the first nucleic acid molecule and the second nucleic acid molecule of claim 1, operably linked to regulatory control sequences which effect expression in a host cell.

4. An expression vector comprising the recombinant DNA of claim 3.

5. An expression vector according to claim 4, wherein the vector is expressible in a prokaryotic cell.

6. An expression vector according to claim 4, wherein the vector is expressible in a eukaryotic cell.

7. A prokaryotic cell comprising the expressible vector of claim 5.

8. A eukaryotic cell comprising the expressible vector of claim 6.

9. The eukaryotic cell of claim 8 which is a COS cell.

10. The eukaryotic cell of claim 8 which comprises the first recombinant DNA and the second recombinant DNA on different vectors.

11. A first nucleic acid molecule encoding a humanized antibody heavy chain or a fragment thereof wherein the humanized antibody heavy chain comprises a human heavy chain constant region and a human heavy chain variable region, wherein CDR1, CDR2 and CDR3 of the heavy chain are substituted with the corresponding CDRs of monoclonal antibody 225 deposited under ATCC Accession No: HB 11935, and amino acid substitutions consisting at positions 24, 28, 29, 30, 48, 49, 67 and 71 according to the Kabat numbering system; and a second nucleic acid molecule encoding a humanized antibody kappa light chain or a fragment thereof wherein the humanized antibody kappa light chain comprises a human kappa light chain constant region and a human kappa light chain variable region, wherein CDR1, CDR2 and CDR3 of the light chain are substituted with the corresponding CDRs of monoclonal antibody 225, and an amino acid substitution consisting at position 49 according to the Kabat numbering system;

wherein a protein encoded by the first nucleic acid molecule and the second nucleic acid molecule binds to human EGF-receptor.

12. The nucleic acid molecule of claim 1 or 11 which encodes the amino acid sequence selected from the group consisting of SEQ ID NO: 116, SEQ ID NO:117, SEQ ID NO:118, SEQ ID NO:119 and SEQ ID NO:120.

13. The nucleic acid molecule of claim 1 or 11 which encodes the amino acid sequence selected from the group consisting of SEQ ID NO: 113 and SEQ ID NO:114.

14. The nucleic acid of claim 1 or 11 wherein the substituted amino acid at position 49 of the light chain is lysine.

15. The nucleic acid molecule of claim 1 or 11 wherein the human heavy chain variable region further comprises one or more amino acid substitutions at positions 41, 68, 70, and 78 according to the Kabat numbering system.

16. The nucleic acid molecule of claim 15 wherein the amino acid substitutions are selected from the group consisting of proline at position 41, serine at position 68, asparagine at position 70, and valine at position 78.

17. The nucleic acid molecule of claim 1 or 11 wherein the human heavy chain variable region amino acid substitutions are valine at position 24, serine at position 28, leucine at position 29, threonine at position 30, leucine at position 48, glycine at position 49, leucine at position 67, and lysine at position 71.

18. The nucleic acid molecule of claim 15 wherein the amino acid substitutions are valine at position 24, serine at position 28, leucine at position 29, threonine at position 30, proline at position 41, leucine at position 48, glycine at position 49, leucine at position 67, and lysine at position 71.

19. The nucleic acid molecule of claim 15 wherein the amino acid substitutions are valine at position 24, serine at position 28, leucine at position 29, threonine at position 30, leucine at position 48, glycine at position 49, leucine at position 67, serine at position 68, asparagine at position 70, and lysine at position 71.

20. The nucleic acid molecule of claim 15 wherein the amino acid substitutions are valine at position 24, serine at position 28, leucine at position 29, threonine at position 30, proline at position 41, leucine at position 48, glycine at position 49, leucine at position 67, serine at position 68, asparagine at position 70, and lysine at position 71.

21. The nucleic acid molecule of claim 15 wherein the amino acid substitutions are valine at position 24, serine at position 28, leucine at position 29, threonine at position 30, leucine at position 48, glycine at position 49, leucine at position 67, lysine at position 71, and valine at position 78.

22. The nucleic acid molecule of claim 1 wherein the isotype of the human constant region is selected from IgG, IgA, IgM, IgD and IgE.

23. The nucleic acid molecule of claim 1 wherein the isotype of the human constant region is selected from IgG1, IgG2, IgG3, and IgG4.

24. The nucleic acid molecule of claim 1 wherein the isotype of the human constant region is IgG1.

* * * * *

SEQUENCE LISTING (1) GENERAL INFORMATION:

(iii) NUMBER OF SEQUENCES: 120

(2) INFORMATION FOR SEQ ID NO: 1:

(i) SEQUENCE CHARACTERISTICS:
       (A) LENGTH: 5 amino acids
       (B) TYPE: amino acid
       (C) STRANDEDNESS: not relevant
       (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 1:

Asn Tyr Gly Val His
1               5

(2) INFORMATION FOR SEQ ID NO: 2:

(i) SEQUENCE CHARACTERISTICS:
       (A) LENGTH: 18 amino acids
       (B) TYPE: amino acid
       (C) STRANDEDNESS: not relevant
       (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 2:

Gly Val Ile Trp Ser Gly Gly Asn Thr Asp Tyr Asn Thr Pro Phe Thr
1               5                  10                  15

Ser Arg (2) INFORMATION FOR SEQ ID NO: 3:

(i) SEQUENCE CHARACTERISTICS:
            (A) LENGTH: 16 amino acids
            (B) TYPE: amino acid
            (C) STRANDEDNESS: not relevant
            (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 3:

Val Ile Trp Ser Gly Gly Asn Thr Asp Tyr Asn Thr Pro Phe Thr Ser
1               5                  10                  15

(2) INFORMATION FOR SEQ ID NO: 4:

(i) SEQUENCE CHARACTERISTICS:
            (A) LENGTH: 381 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 4:

ATGAGGGCCC CTGCTCAGTT TCTTGGCTTC TTGCTTTTCT GGATTCCAGC CTCCAGAAGT      60

GACATCTTGC TGACTCAGTC TCCAGTCATC CTGTCTGTGA GTCCAGGAGA AAGAGTCAGT     120

TTCTCCTGCA GGGCCAGTCA GAGTATTGGC ACAAACATAC ACTGGTATCA GCAAAGAACA     180

AATGGTTCTC CAAGGCTTCT CATAAAGTAT GCTTCTGAGT CTATCTCTGG GATCCCTTCC     240

AGGTTTAGTG GCAGTGGATC AGGGACAGAT TTTACTCTTA GCATCAACAG TGTGGAGTCT     300

GAAGATATTG CAGATTATTA CTGTCAACAA AATAATAACT GGCCAACCAC GTTCGGTGCT     360

GGGACCAAGC TGGAGCTGAA A                                               381

(2) INFORMATION FOR SEQ ID NO: 5:

(i) SEQUENCE CHARACTERISTICS:
            (A) LENGTH: 127 amino acids
            (B) TYPE: amino acid
            (C) STRANDEDNESS: not relevant
            (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 5:

```
Met Arg Ala Pro Ala Gln Phe Leu Gly Phe Leu Leu Phe Trp Ile Pro
1               5                   10                  15

Ala Ser Arg Ser Asp Ile Leu Leu Thr Gln Ser Pro Val Ile Leu Ser
            20                  25                  30

Val Ser Pro Gly Glu Arg Val Ser Phe Ser Cys Arg Ala Ser Gln Ser
        35                  40                  45

Ile Gly Thr Asn Ile His Trp Tyr Gln Gln Arg Thr Asn Gly Ser Pro
    50                  55                  60

Arg Leu Leu Ile Lys Tyr Ala Ser Glu Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Ser Glu Asp Ile Ala Asp Tyr Tyr Cys Gln Gln Asn Asn
            100                 105                 110

Asn Trp Pro Thr Thr Phe Gly Ala Gly Thr Lys Leu Glu Leu Lys
        115                 120                 125
```

(2) INFORMATION FOR SEQ ID NO: 6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 6:

```
ATGAGGGCCC CTGCTCAGTT TCTTGGCTTC TTG                              33
```

(2) INFORMATION FOR SEQ ID NO: 7:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 7:

```
ATGGCTGTCT TGGCGCTGCT CTTCTGCCTG GTGACATTCC CAAGCTGTGT CCTATCCCAG    60
GTGCAGCTGA AGCAGTCAGG ACCTGGCCTA GTGCAGCCCT CACAGAGCCT GTCCATCACC   120
TGCACAGTCT CTGGTTTCTC ATTAACTAAC TATGGTGTAC ACTGGGTTCG CCAGTCTCCA   180
GGAAAGGGTC TGGAGTGGCT GGGAGTGATA TGGAGTGGTG GAAACACAGA CTATAATACA   240
CCTTTCACAT CCAGACTGAG CATCAACAAG GACAATTCCA AGAGCCAAGT TTTCTTTAAA   300
ATGAACAGTC TGCAATCTAA TGACACAGCC ATATATTACT GTGCCAGAGC CCTCACCTAC   360
TATGATTACG AGTTTGCTTA CTGGGGCCAA GGGACTCTGG TCACTGTCTC TGCA         414
```

(2) INFORMATION FOR SEQ ID NO: 8:

(i) SEQUENCE CHARACTERISTICS:
    (A) LENGTH: 138 amino acids
    (B) TYPE: amino acid
    (C) STRANDEDNESS: not relevant
    (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 8:

```
Met Ala Val Leu Ala Leu Leu Phe Cys Leu Val Thr Phe Pro Ser Cys
1               5                   10                  15
Val Leu Ser Gln Val Gln Leu Lys Gln Ser Gly Pro Gly Leu Val Gln
            20                  25                  30
Pro Ser Gln Ser Leu Ser Ile Thr Cys Thr Val Ser Gly Phe Ser Leu
        35                  40                  45
Thr Asn Tyr Gly Val His Trp Val Arg Gln Ser Pro Gly Lys Gly Leu
    50                  55                  60
Glu Trp Leu Gly Val Ile Trp Ser Gly Gly Asn Thr Asp Tyr Asn Thr
65                  70                  75                  80
Pro Phe Thr Ser Arg Leu Ser Ile Asn Lys Asp Asn Ser Lys Ser Gln
                85                  90                  95
Val Phe Phe Lys Met Asn Ser Leu Gln Ser Asn Asp Thr Ala Ile Tyr
            100                 105                 110
Tyr Cys Ala Arg Ala Leu Thr Tyr Tyr Asp Tyr Glu Phe Ala Tyr Trp
        115                 120                 125
Gly Gln Gly Thr Leu Val Thr Val Ser Ala
    130                 135
```

(2) INFORMATION FOR SEQ ID NO: 9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 9:

ATGGCTGTCT TGGCGCTGCT CTTCTGC                                              27

(2) INFORMATION FOR SEQ ID NO: 10:

(i) SEQUENCE CHARACTERISTICS:
        (A) LENGTH: 416 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 10:

AAGCTTGCCG CCACCATGAG GGCCCCTGCT CAGTTTCTTG GCTTCTTGCT TTTCTGGATT         60

```
CCAGCCTCCA GAAGTGACAT CTTGCTGACT CAGTCTCCAG TCATCCTGTC TGTGAGTCCA      120

GGAGAAAGAG TCAGTTTCTC CTGCAGGGCC AGTCAGAGTA TTGGCACAAA CATACACTGG      180

TATCAGCAAA GAACAAATGG TTCTCCAAGG CTTCTCATAA AGTATGCTTC TGAGTCTATC      240

TCTGGGATCC CTTCCAGGTT TAGTGGCAGT GGATCAGGGA CAGATTTTAC TCTTAGCATC      300

AACAGTGTGG AGTCTGAAGA TATTGCAGAT TATTACTGTC AACAAAATAA TAACTGGCCA      360

ACCACGTTCG GTGCTGGGAC CAAGCTGGAG CTGAAACGTG AGTGGATCCT TCTAGA         416
```

(2) INFORMATION FOR SEQ ID NO: 11:

(i) SEQUENCE CHARACTERISTICS:
        (A) LENGTH: 127 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 11:

```
Met Arg Ala Pro Ala Gln Phe Leu Gly Phe Leu Leu Phe Trp Ile Pro
1               5                   10                  15

Ala Ser Arg Ser Asp Ile Leu Leu Thr Gln Ser Pro Val Ile Leu Ser
            20                  25                  30

Val Ser Pro Gly Glu Arg Val Ser Phe Ser Cys Arg Ala Ser Gln Ser
        35                  40                  45

Ile Gly Thr Asn Ile His Trp Tyr Gln Gln Arg Thr Asn Gly Ser Pro
50                  55                  60

Arg Leu Leu Ile Lys Tyr Ala Ser Glu Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Ser Glu Asp Ile Ala Asp Tyr Tyr Cys Gln Gln Asn Asn
            100                 105                 110

Asn Trp Pro Thr Thr Phe Gly Ala Gly Thr Lys Leu Glu Leu Lys
        115                 120                 125
```

(2) INFORMATION FOR SEQ ID NO: 12:

(i) SEQUENCE CHARACTERISTICS:
        (A) LENGTH: 442 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 12:

```
AAGCTTGCCG CCACCATGGC TGTCTTGGGG CTGCTCTTCT GCCTGGTGAC ATTCCCAAGC       60

TGTGTCCTAT CCCAGGTGCA GCTGAAGCAG TCAGGACCTG GCCTAGTGCA GCCCTCACAG      120

AGCCTGTCCA TCACCTGCAC AGTCTCTGGT TTCTCATTAA CTAACTATGG TGTACACTGG      180

GTTCGCCAGT CTCCAGGAAA GGGTCTGGAG TGGCTGGGAG TGATATGGAG TGGTGGAAAC      240
```

```
ACAGACTATA ATACACCTTT CACATCCAGA CTGAGCATCA ACAAGGACAA TTCCAAGAGC      300

CAAGTTTTCT TTAAAATGAA CAGTCTGCAA TCTAATGACA CAGCCATATA TTACTGTGCC      360

AGAGCCCTCA CCTACTATGA TTACGAGTTT GCTTACTGGG CCAAGGGAC TCTGGTCACT       420

GTCTCTGCAG GTGAGTGGAT CC                                               442

(2) INFORMATION FOR SEQ ID NO: 13:

(i) SEQUENCE CHARACTERISTICS:
        (A) LENGTH: 138 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 13:

Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Val His Trp Val Arg Gln Ser Pro Gly Lys Gly Leu
50                  55                  60

Glu Trp Leu Gly Val Ile Trp Ser Gly Gly Asn Thr Asp Tyr Asn Thr
65                  70                  75                  80

Pro Phe Thr Ser Arg Leu Ser Ile Asn Lys Asp Asn Ser Lys Ser Gln
                85                  90                  95

Val Phe Phe Lys Met Asn Ser Leu Gln Ser Asn Asp Thr Ala Ile Tyr
            100                 105                 110

Tyr Cys Ala Arg Ala Leu Thr Tyr Tyr Asp Tyr Glu Phe Ala Tyr Trp
        115                 120                 125

Gly Gln Gly Thr Leu Val Thr Val Ser Ala
        130                 135

(2) INFORMATION FOR SEQ ID NO: 14:

(i) SEQUENCE CHARACTERISTICS:
        (A) LENGTH: 416 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 14:

AAGCTTGCCG CCACCATGGT ATCCACACCT GAGTTCCTTG TATTTTTGCT TTTCTGGATT       60

CCAGCCTCCA GAGGTGACAT CTTGCTGACT CAGTCTCCAG TCATCCTGTC TGTGAGTCCA      120

GGAGAAAGAG TCAGTTTCTC CTGCAGGGCC AGTCAGAGTA TTGGCACAAA CATACACTGG      180

TATCAGCAAA GAACAAATGG TTCTCCAAGG CTTCTCATAA AGTATGCTTC TGAGTCTATC      240

TCTGGGATCC CTTCCAGGTT TAGTGGCAGT GGATCAGGGA CAGATTTTAC TCTTAGCATC      300
```

```
AACAGTGTGG AGTCTGAAGA TATTGCAGAT TATTACTGTC AACAAAATAA TAACTGGCCA      360

ACCACGTTCG GTGCTGGGAC CAAGCTGGAG CTGAAACGTG AGTGGATCCT TCTAGA          416
```

(2) INFORMATION FOR SEQ ID NO: 15:

(i) SEQUENCE CHARACTERISTICS:
        (A) LENGTH: 127 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 15:

```
Met Val Ser Thr Pro Glu Phe Leu Val Phe Leu Leu Phe Trp Ile Pro
1               5                   10                  15

Ala Ser Arg Gly Asp Ile Leu Leu Thr Gln Ser Pro Val Ile Leu Ser
            20                  25                  30

Val Ser Pro Gly Glu Arg Val Ser Phe Ser Cys Arg Ala Ser Gln Ser
        35                  40                  45

Ile Gly Thr Asn Ile His Trp Tyr Gln Gln Arg Thr Asn Gly Ser Pro
    50                  55                  60

Arg Leu Leu Ile Lys Tyr Ala Ser Glu Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Ser Glu Asp Ile Ala Asp Tyr Tyr Cys Gln Gln Asn Asn
                100                 105                 110

Asn Trp Pro Thr Thr Phe Gly Ala Gly Thr Lys Leu Glu Leu Lys
            115                 120                 125
```

(2) INFORMATION FOR SEQ ID NO: 16:

(i) SEQUENCE CHARACTERISTICS:
        (A) LENGTH: 416 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 16:

```
AAGCTTGCCG CCACCATGGA AGCCCCAGCT CAGCTTCTCT TCCTCTTGCT TCTCTGGCTC      60

CCAGATACCA CCGGAGAAAT CGTACTGACT CAGTCTCCAG CCACCCTGTC TTTGAGTCCA     120

GGAGAAAGAG CCACCCTCTC CTGCAGGGCC AGTCAGAGTA TTGGCACAAA CATACACTGG     180

TATCAGCAAA GACCTGGCCA GGCTCCAAGG CTTCTCATAA AGTATGCTTC TGAGTCTATC     240

TCTGGAATCC CTGCCAGGTT TAGTGGCAGT GGATCAGGGA CAGATTTTAC TCTTACCATC     300

AGCAGTCTGG AGCCTGAAGA TTTTGCAGTT TATTACTGTC AACAAAATAA TAACTGGCCA     360

ACCACGTTCG GTGGAGGGAC CAAGGTGGAG ATCAAACGTG AGTGGATCCT TCTAGA         416
```

(2) INFORMATION FOR SEQ ID NO: 17:

(i) SEQUENCE CHARACTERISTICS:
    (A) LENGTH: 127 amino acids
    (B) TYPE: amino acid
    (C) STRANDEDNESS: not relevant
    (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 17:

```
Met Glu Ala Pro Ala Gln Leu Leu Phe Leu Leu Leu Leu Trp Leu Pro
1               5                   10                  15
Asp Thr Thr Gly Glu Ile Val Leu Thr Gln Ser Pro Ala Thr Leu Ser
            20                  25                  30
Leu Ser Pro Gly Glu Arg Ala Thr Leu Ser Cys Arg Ala Ser Gln Ser
        35                  40                  45
Ile Gly Thr Asn Ile His Trp Tyr Gln Gln Arg Pro Gly Gln Ala Pro
    50                  55                  60
Arg Leu Leu Ile Lys Tyr Ala Ser Glu Ser Ile Ser Gly Ile Pro Ala
65                  70                  75                  80
Arg Phe Ser Gly Ser Gly Ser Gly Thr Asp Phe Thr Leu Thr Ile Ser
                85                  90                  95
Ser Leu Glu Pro Glu Asp Phe Ala Val Tyr Tyr Cys Gln Gln Asn Asn
            100                 105                 110
Asn Trp Pro Thr Thr Phe Gly Gly Gly Thr Lys Val Glu Ile Lys
        115                 120                 125
```

(2) INFORMATION FOR SEQ ID NO: 18:

(i) SEQUENCE CHARACTERISTICS:
        (A) LENGTH: 442 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 18:

```
AAGCTTGCCG CCACCATGGA GTTTGGGCTG AGCTGGCTTT TCTTGTGGC TATTTTAAAA       60
GGTGTCCAGT GTGAGGTGCA GCTGGTCGAG TCTGGGGGAG GCTTGGTACA GCCTGGGGGG     120
TCCCTGAGAC TCTCCTGTGC AGTCTCCGGA TTCTCATTAA CTAACTATGG TGTACACTGG     180
GTTCGCCAGG CTACAGGAAA GGGTCTGGAG TGGCTGGAG TGATATGGAG TGGTGGAAAC      240
ACAGACTATA ATACCCTTT CACAAGTCGA CTGACCATCT CCAAGGAAAA TGCCAAGAAC      300
TCCCTGTATC TGCAAATGAA CAGTCTCAGA GCCGGGACA CAGCCGTGTA TTACTGTGCC      360
AGAGCCCTCA CCTACTATGA TTACGAGTTT GCTTACTGGG GCCAAGGGAC TATGGTCACT     420
GTCTCTTCAG GTGAGTGGAT CC                                              442
```

(2) INFORMATION FOR SEQ ID NO: 19:

(i) SEQUENCE CHARACTERISTICS:
        (A) LENGTH: 138 amino acids
        (B) TYPE: amino acid
        (C) STRANDEDNESS: not relevant
        (D) TOPOLOGY: not relevant

```
    (ii) MOLECULE TYPE: peptide (iii) HYPOTHETICAL: NO (v) FRAGMENT TYPE: internal (xi) SEQUENCE DESCRIPTION: SEQ ID NO: 19:

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Val Ser Gly Phe Ser Leu
        35                  40                  45

Thr Asn Tyr Gly Val His Trp Val Arg Gln Ala Thr Gly Lys Gly Leu
50                  55                  60

Glu Trp Leu Gly Val Ile Trp Ser Gly Gly Asn Thr Asp Tyr Asn Thr
65                  70                  75                  80

Pro Phe Thr Ser Arg Leu Thr Ile Ser Lys Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Ala Arg Ala Leu Thr Tyr Tyr Asp Tyr Glu Phe Ala Tyr Trp
        115                 120                 125

Gly Gln Gly Thr Met Val Thr Val Ser Ser
        130                 135

(2) INFORMATION FOR SEQ ID NO: 20:

(i) SEQUENCE CHARACTERISTICS:
         (A) LENGTH: 113 amino acids
         (B) TYPE: amino acid
         (C) STRANDEDNESS: not relevant
         (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 20:

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Xaa Xaa Xaa Xaa Xaa
            20                  25                  30

Xaa Ser Ile Gly Thr Asn Ile His Trp Tyr Gln Gln Arg Thr Asn Gly
        35                  40                  45

Ser Pro Arg Leu Leu Ile Lys Tyr Ala Ser Glu Ser Ile Ser Gly Ile
50                  55                  60

Pro Ser Arg Phe Ser Ser Ser Gly Ser Gly Thr Asp Phe Thr Leu Ser
65                  70                  75                  80

Ile Asn Ser Val Glu Ser Glu Asp Ile Ala Asp Tyr Tyr Cys Gln Gln
                85                  90                  95

Asn Asn Asn Trp Pro Thr Thr Phe Gly Ala Gly Thr Lys Leu Glu Leu
            100                 105                 110

Lys (2) INFORMATION FOR SEQ ID NO: 21:
```

(i) SEQUENCE CHARACTERISTICS:
            (A) LENGTH: 113 amino acids
            (B) TYPE: amino acid
            (C) STRANDEDNESS: not relevant
            (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 21:

Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Xaa Xaa Xaa Xaa Xaa
            20                  25                  30

Xaa Ser Val Ser Ser Tyr Leu Ala Trp Tyr Gln Gln Arg Pro Gly Gln
        35                  40                  45

Ala Pro Arg Leu Leu Ile Tyr Asp Ala Ser Asn Arg Ala Thr Gly Ile
50                  55                  60

Pro Ala Arg Phe Ser Gly Ser Gly Ser Gly Thr Asp Phe Thr Leu Thr
65                  70                  75                  80

Ile Ser Ser Leu Glu Pro Glu Asp Phe Ala Val Tyr Tyr Cys Gln Gln
                85                  90                  95

Arg Ser Asn Trp Pro Leu Thr Phe Gly Gly Thr Lys Val Glu Ile
            100                 105                 110

Lys (2) INFORMATION FOR SEQ ID NO: 22:

(i) SEQUENCE CHARACTERISTICS:
            (A) LENGTH: 113 amino acids
            (B) TYPE: amino acid
            (C) STRANDEDNESS: not relevant
            (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 22:

Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Xaa Xaa Xaa Xaa Xaa
            20                  25                  30

Xaa Ser Ile Gly Thr Asn Ile His Trp Tyr Gln Gln Arg Pro Gly Gln
        35                  40                  45

Ala Pro Arg Leu Leu Ile Lys Tyr Ala Ser Glu Ser Ile Ser Gly Ile
50                  55                  60

Pro Ala Arg Phe Ser Ser Gly Ser Gly Thr Asp Phe Thr Leu Thr
65                  70                  75                  80

Ile Ser Ser Leu Glu Pro Glu Asp Phe Ala Val Tyr Tyr Cys Gln Gln
                85                  90                  95

Asn Asn Asn Trp Pro Thr Thr Phe Gly Gly Thr Lys Val Glu Ile
            100                 105                 110

Lys (2) INFORMATION FOR SEQ ID NO: 23:

```
    (i) SEQUENCE CHARACTERISTICS:
        (A) LENGTH: 113 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 23:
```

Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Xaa Xaa Xaa Xaa
            20                  25                  30

Xaa Ser Ile Gly Thr Asn Ile His Trp Tyr Gln Gln Arg Pro Gly Gln
        35                  40                  45

Ala Pro Arg Leu Leu Ile Tyr Tyr Ala Ser Glu Ser Ile Ser Gly Ile
    50                  55                  60

Pro Ala Arg Phe Ser Ser Ser Gly Ser Gly Thr Asp Phe Thr Leu Thr
65                  70                  75                  80

Ile Ser Ser Leu Glu Pro Glu Asp Phe Ala Val Tyr Tyr Cys Gln Gln
                85                  90                  95

Asn Asn Asn Trp Pro Thr Thr Phe Gly Gly Gly Thr Lys Val Glu Ile
            100                 105                 110

Lys

```
(2) INFORMATION FOR SEQ ID NO: 24:

(i) SEQUENCE CHARACTERISTICS:
        (A) LENGTH: 132 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 24:
```

Gln Val Gln Leu Lys Gln Ser Gly Pro Gly Leu Val Gln Pro Ser Gln
1               5                  10                  15

Ser Leu Ser Ile Thr Cys Thr Val Ser Gly Phe Ser Leu Thr Asn Tyr
            20                  25                  30

Gly Val His Xaa Xaa Trp Val Arg Gln Ser Pro Gly Lys Gly Leu Glu
        35                  40                  45

Trp Leu Gly Val Ile Trp Xaa Xaa Xaa Ser Gly Gly Asn Thr Asp Tyr
    50                  55                  60

Asn Thr Pro Phe Thr Ser Arg Leu Ser Ile Asn Lys Asp Asn Ser Lys
65                  70                  75                  80

Ser Gln Val Phe Phe Lys Met Asn Ser Leu Gln Ser Asn Asp Thr Ala
                85                  90                  95

Ile Tyr Tyr Cys Ala Arg Ala Leu Thr Tyr Tyr Asp Tyr Glu Xaa Xaa
            100                 105                 110

Xaa Xaa Xaa Xaa Xaa Xaa Phe Ala Tyr Trp Gly Gln Gly Thr Leu Val
        115                 120                 125

```
Thr Val Ser Ala
    130

(2) INFORMATION FOR SEQ ID NO: 25:

(i) SEQUENCE CHARACTERISTICS:
        (A) LENGTH: 131 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 25:

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Xaa Xaa Trp Val Arg Gln Ala Thr Gly Lys Gly Leu Glu
        35                  40                  45

Trp Val Ser Ala Ile Gly Xaa Xaa Xaa Thr Ala Gly Asp Thr Tyr Tyr
    50                  55                  60

Pro Gly Ser Val Lys Gly Arg Phe Thr Ile Ser Arg Glu Asn Ala Lys
65                  70                  75                  80

Asn Ser Leu Tyr Leu Gln Met Asn Ser Leu Arg Ala Gly Asp Thr Ala
                85                  90                  95

Val Tyr Tyr Cys Ala Arg Ser Phe Ser Glu Thr Glu Asp Ala Xaa Xaa
                100                 105                 110

Xaa Xaa Xaa Xaa Xaa Phe Asp Ile Trp Gly Gln Gly Thr Met Val Thr
            115                 120                 125

Val Ser Ser
    130

(2) INFORMATION FOR SEQ ID NO: 26:

(i) SEQUENCE CHARACTERISTICS:
        (A) LENGTH: 132 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 26:

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Asn Tyr
            20                  25                  30

Gly Val His Xaa Xaa Trp Val Arg Gln Ala Thr Gly Lys Gly Leu Glu
        35                  40                  45

Trp Leu Gly Val Ile Trp Xaa Xaa Xaa Ser Gly Gly Asn Thr Asp Tyr
    50                  55                  60

Asn Thr Pro Phe Thr Ser Arg Leu Thr Ile Ser Lys Glu Asn Ala Lys
65                  70                  75                  80
```

-continued

```
Asn Ser Leu Tyr Leu Gln Met Asn Ser Leu Arg Ala Gly Asp Thr Ala
                85                  90                  95

Val Tyr Tyr Cys Ala Arg Ala Leu Thr Tyr Tyr Asp Tyr Glu Xaa Xaa
               100                 105                 110

Xaa Xaa Xaa Xaa Xaa Xaa Phe Ala Tyr Trp Gly Gln Gly Thr Met Val
       115                 120                 125

Thr Val Ser Ser
       130
```

(2) INFORMATION FOR SEQ ID NO: 27:

(i) SEQUENCE CHARACTERISTICS:
        (A) LENGTH: 132 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 27:

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Asn Tyr
                20                  25                  30

Gly Val His Xaa Xaa Trp Val Arg Gln Ala Pro Gly Lys Gly Leu Glu
            35                  40                  45

Trp Leu Gly Val Ile Trp Xaa Xaa Xaa Ser Gly Gly Asn Thr Asp Tyr
 50                 55                  60

Asn Thr Pro Phe Thr Ser Arg Leu Thr Ile Ser Lys Glu Asn Ala Lys
 65                 70                  75                  80

Asn Ser Leu Tyr Leu Gln Met Asn Ser Leu Arg Ala Gly Asp Thr Ala
                85                  90                  95

Val Tyr Tyr Cys Ala Arg Ala Leu Thr Tyr Tyr Asp Tyr Glu Xaa Xaa
               100                 105                 110

Xaa Xaa Xaa Xaa Xaa Xaa Phe Ala Tyr Trp Gly Gln Gly Thr Met Val
       115                 120                 125

Thr Val Ser Ser
       130
```

(2) INFORMATION FOR SEQ ID NO: 28:

(i) SEQUENCE CHARACTERISTICS:
        (A) LENGTH: 132 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 28:

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Asn Tyr
                20                  25                  30
```

```
Gly Val His Xaa Xaa Trp Val Arg Gln Ala Pro Gly Lys Gly Leu Glu
            35              40                  45

Trp Leu Gly Val Ile Trp Xaa Xaa Xaa Ser Gly Gly Asn Thr Asp Tyr
     50              55                  60

Asn Thr Pro Phe Thr Ser Arg Leu Ser Ile Asn Lys Glu Asn Ala Lys
 65              70                  75                      80

Asn Ser Leu Tyr Leu Gln Met Asn Ser Leu Arg Ala Gly Asp Thr Ala
                 85                  90                  95

Val Tyr Tyr Cys Ala Arg Ala Leu Thr Tyr Tyr Asp Tyr Glu Xaa Xaa
                100                 105                 110

Xaa Xaa Xaa Xaa Xaa Xaa Phe Ala Tyr Trp Gly Gln Gly Thr Met Val
            115                 120                 125

Thr Val Ser Ser
    130
```

(2) INFORMATION FOR SEQ ID NO: 29:

(i) SEQUENCE CHARACTERISTICS:
        (A) LENGTH: 132 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 29:

```
Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Ser Leu Thr Asn Tyr
            20                  25                  30

Gly Val His Xaa Xaa Trp Val Arg Gln Ala Pro Gly Lys Gly Leu Glu
            35              40                  45

Trp Leu Gly Val Ile Trp Xaa Xaa Xaa Ser Gly Gly Asn Thr Asp Tyr
     50              55                  60

Asn Thr Pro Phe Thr Ser Arg Leu Ser Ile Asn Lys Glu Asn Ala Lys
 65              70                  75                      80

Asn Ser Leu Tyr Leu Gln Met Asn Ser Leu Arg Ala Gly Asp Thr Ala
                 85                  90                  95

Val Tyr Tyr Cys Ala Arg Ala Leu Thr Tyr Tyr Asp Tyr Glu Xaa Xaa
                100                 105                 110

Xaa Xaa Xaa Xaa Xaa Xaa Phe Ala Tyr Trp Gly Gln Gly Thr Met Val
            115                 120                 125

Thr Val Ser Ser
    130
```

(2) INFORMATION FOR SEQ ID NO: 30:

(i) SEQUENCE CHARACTERISTICS:
        (A) LENGTH: 132 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 30:

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Asn Tyr
            20                  25                  30

Gly Val His Xaa Xaa Trp Val Arg Gln Ala Pro Gly Lys Gly Leu Glu
        35                  40                  45

Trp Leu Gly Val Ile Trp Xaa Xaa Xaa Ser Gly Gly Asn Thr Asp Tyr
50                  55                  60

Asn Thr Pro Phe Thr Ser Arg Leu Ser Ile Asn Lys Glu Asn Ala Lys
65                  70                  75                  80

Asn Ser Val Tyr Leu Gln Met Asn Ser Leu Arg Ala Gly Asp Thr Ala
                85                  90                  95

Val Tyr Tyr Cys Ala Arg Ala Leu Thr Tyr Tyr Asp Tyr Glu Xaa Xaa
            100                 105                 110

Xaa Xaa Xaa Xaa Xaa Xaa Phe Ala Tyr Trp Gly Gln Gly Thr Met Val
        115                 120                 125

Thr Val Ser Ser
    130

(2) INFORMATION FOR SEQ ID NO: 31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 31:

ATGAAGTTGC CTGTTAGGCT GTTGGTGCTG                                        30

(2) INFORMATION FOR SEQ ID NO: 32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 32:

ATGGAGACAG ACACACTCCT GCTATGGGTG                                        30

(2) INFORMATION FOR SEQ ID NO: 33:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 33:

ATGAGTGTGC TCACTCAGGT CCTGGCGTTG                                    30

(2) INFORMATION FOR SEQ ID NO: 34:

(i) SEQUENCE CHARACTERISTICS:
           (A) LENGTH: 33 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 34:

ATGAGGGCCC CTGCTCAGTT TTTTGGCTTC TTG                                 33

(2) INFORMATION FOR SEQ ID NO: 35:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 35:

ATGGATTTTC AGGTGCAGAT TATCAGCTTC                                    30

(2) INFORMATION FOR SEQ ID NO: 36:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 36:

ATGAGGTGCC CTGTTCAGTT CCTGGGG                                       27

(2) INFORMATION FOR SEQ ID NO: 37:

(i) SEQUENCE CHARACTERISTICS:
           (A) LENGTH: 31 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 37:

ATGGGCATCA AGATGGAGTC ACAGACCCAG G                                31

(2) INFORMATION FOR SEQ ID NO: 38:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 38:

ATGTGGGGAC CTTTTTTCCC TTTTTCAATT G                                31

(2) INFORMATION FOR SEQ ID NO: 39:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 39:

ATGGTATCCA CACCTCAGTT CCTTG                                      25

(2) INFORMATION FOR SEQ ID NO: 40:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 40:

ATGTATATAT GTTTGTTGTC TATTTCT                                    27

(2) INFORMATION FOR SEQ ID NO: 41:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 41:

```
ATGGAAGCCC CAGCTCAGCT TCTCTTCC                                    28
```

(2) INFORMATION FOR SEQ ID NO: 42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 42:

```
ACTGGATGGT GGGAAGATGG                                              20
```

(2) INFORMATION FOR SEQ ID NO: 43:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 43:

```
ATGAAATGCA GCTGGGGCAT CTTCTTC                                      27
```

(2) INFORMATION FOR SEQ ID NO: 44:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 44:

```
ATGGGATGGA GCTGTATCAT GTTCTT                                       26
```

(2) INFORMATION FOR SEQ ID NO: 45:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 45:

```
ATGAAGTTGT GGTTAAACTG GGTTTTT                                      27
```

(2) INFORMATION FOR SEQ ID NO: 46:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 46:

ATGAACTTTG GGCTCAGCTT GATTT     25

(2) INFORMATION FOR SEQ ID NO: 47:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 47:

ATGGACTCCA GGCTCAATTT AGTTTTCCTT     30

(2) INFORMATION FOR SEQ ID NO: 48:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 48:

ATGGCTGTCC TAGGGCTACT CTTCTGC     27

(2) INFORMATION FOR SEQ ID NO: 49:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 49:

ATGGGATGGA GCGGGATCTT TCTCTT     26

(2) INFORMATION FOR SEQ ID NO: 50:

(i) SEQUENCE CHARACTERISTICS:

```
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 50:

ATGAGAGTGC TGATTCTTTT GTG                                              23

(2) INFORMATION FOR SEQ ID NO: 51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 51:

ATGGATTGGG TGTGGACCTT GCTATTCCTG                                       30

(2) INFORMATION FOR SEQ ID NO: 52:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 52:

ATGGGCAGAC TTACATTCTC ATTCCTG                                          27

(2) INFORMATION FOR SEQ ID NO: 53:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 53:

ATGGATTTTG GGCTGATTTT TTTTATTG                                         28

(2) INFORMATION FOR SEQ ID NO: 54:

(i) SEQUENCE CHARACTERISTICS:
        (A) LENGTH: 27 base pairs
        (B) TYPE: nucleic acid
        (C) STRANDEDNESS: single
```

(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 54:

ATGATGGTGT TAAGTCTTCT GTACCTG                                         27

(2) INFORMATION FOR SEQ ID NO: 55:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 55:

CAGTGGATAG ACAGATGGGG G                                               21

(2) INFORMATION FOR SEQ ID NO: 56:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 56:

CTAGATGCAT GCTCGAGC                                                   18

(2) INFORMATION FOR SEQ ID NO: 57:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 57:

TACCGAGCTC GGATCCACTA G                                               21

(2) INFORMATION FOR SEQ ID NO: 58:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 58:

AGCGGATAAC AATTTCACAC AGGA                                                      24

(2) INFORMATION FOR SEQ ID NO: 59:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 59:

CGCCAGGGTT TTCCCAGTCA CGAC                                                      24

(2) INFORMATION FOR SEQ ID NO: 60:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 60:

ACGACACCGT CACCGGTTCG                                                           20

(2) INFORMATION FOR SEQ ID NO: 61:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 61:

GTCACCGTCC TTGACACGCG TCTCGGGA                                                  28

(2) INFORMATION FOR SEQ ID NO: 62:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 62:

GTTGTTTGCG CATAATCACA GGGCA                                           25

(2) INFORMATION FOR SEQ ID NO: 63:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 63:

TTGGAGGAGG GTGCCAG                                                    17

(2) INFORMATION FOR SEQ ID NO: 64:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 64:

CAGCAAAGAC CTGGCCAGGC TCCAAGGCTT CTCATATATT ATGCTTCTGA GTCTATCTCT     60

(2) INFORMATION FOR SEQ ID NO: 65:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 65:

AAGCTTGCCG CCACCATGGC TGTCTTGGGG CTGCTC                               36

(2) INFORMATION FOR SEQ ID NO: 66:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 66:

```
GGATCCACTC ACCTGCAGAG ACAGTGACCA GAGT                          34
```

(2) INFORMATION FOR SEQ ID NO: 67:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 67:

```
AAGCTTGCCG CCACCATGGT ATCCACACCT CAGAAC                        36
```

(2) INFORMATION FOR SEQ ID NO: 68:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 68:

```
TCTAGAAGGA TCCACTCACG TTTCAGCTCC AGCTTGGTCC                    40
```

(2) INFORMATION FOR SEQ ID NO: 69:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 69:

```
AAGCTTGCCG CCACCATGGT ATCCACACCT CAGTTCCTTG TATTTTTGCT TTTCTGGATT    60

CCAGCCTCCA GAGGTGACAT CTTGCTGACT CAGTCTCCA                           99
```

(2) INFORMATION FOR SEQ ID NO: 70:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 70:

AGAGATAGAC TCAGAAGCAT A                                            21

(2) INFORMATION FOR SEQ ID NO: 71:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 71:

CTGGAGACTG AGTCAGTACG ATTTCACTTC TGGAGGCTCG AATCCAGAAA AGCAAAAATA    60

CTTGGTTCTG AGGTGTGGAT ACCATGGT                                      88

(2) INFORMATION FOR SEQ ID NO: 72:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 72:

TCGTACTGAC TCAGTCTCCA GCCACCCTGT CTTTGAGTCC AGGAGAAAGA GCCACCCTCT    60

CCTGCAGGGC CAGTCAGAGT                                               80

(2) INFORMATION FOR SEQ ID NO: 73:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 73:

GAGATAGACT CAGAAGCATA CTTTATGAGA AGCCTTGGAG CCTGGCCAGG TCTTTGCTGA    60

TACCAGTGTA TGTT                                                     74

(2) INFORMATION FOR SEQ ID NO: 74:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 74:

GGCTTCTCAT AAAGTATGCT TCTGAGTCTA TCTCTGGAAT CCCTGCCAGG TTTAGTGGCA          60

GTGGATCAGG G                                                              71

(2) INFORMATION FOR SEQ ID NO: 75:

(i) SEQUENCE CHARACTERISTICS:
          (A) LENGTH: 77 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 75:

TTTTGTTGAC AGTAATAAAC TGCAAAATCT TCAGGCTCCA CACTGCTGAT GGTAAGAGTA          60

AAATCTGTCC CTGATCC                                                        77

(2) INFORMATION FOR SEQ ID NO: 76:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 76:

GATTTTGCAG TTTATTACTG TCAACAAAAT AAT                                      33

(2) INFORMATION FOR SEQ ID NO: 77:

(i) SEQUENCE CHARACTERISTICS:
          (A) LENGTH: 68 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 77:

TCTAGAAGGA TCCACTCACG TTTCAGCTCC ACCTTGGTCC CTCCACCGAA CGTGGTTGGC          60

CAGTTATT                                                                  68

(2) INFORMATION FOR SEQ ID NO: 78:

(i) SEQUENCE CHARACTERISTICS:
          (A) LENGTH: 42 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 78:

ACTCTTACCA TCAGCAGTCT GGAGCCTGAA GATTTTGCAG TT                          42

(2) INFORMATION FOR SEQ ID NO: 79:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 79:

TCTAGAAGGA TCCACTCACG TTTGATCTCC ACCTTGGTCC CTCCACCGAA CGTGGTT          57

(2) INFORMATION FOR SEQ ID NO: 80:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 80:

AAGCTTGCCG CCACCATGGA AGCCCCAGCT CAGCTTCTCT TCCTCTTGCT TCTCTGGCTC       60

CCAGATACCA CCGGAGAAAT CGTACTGACT CAGTCTCCA                             99

(2) INFORMATION FOR SEQ ID NO: 81:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 81:

CAGCAAAGAC CTGGCCAGGC TCCAAGGCTT CTCATATATT ATGCTTCTGA GTCTATCTCT       60

(2) INFORMATION FOR SEQ ID NO: 82:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 82:

CTGAGAGTGC ACCATATGCG GTGTG                                               25

(2) INFORMATION FOR SEQ ID NO: 83:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 83:

GGTGCAGCTG GTCGAGTCTG GGGGAGGCTT GGTACAG                                  37

(2) INFORMATION FOR SEQ ID NO: 84:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 84:

GGCTGTACCA AGCCTCCCCC AGACTCGACC AGCTGCACCT CACACTGGAC                    50

(2) INFORMATION FOR SEQ ID NO: 85:

(i) SEQUENCE CHARACTERISTICS:
            (A) LENGTH: 64 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 85:

CCCAGTGTAC ACCATAGTTA GTTAATGAGA ATCCGGAGAC TGCACAGGAG AGTCTCAGGG         60

ACCC                                                                      64

(2) INFORMATION FOR SEQ ID NO: 86:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 86:

TTAACTAACT ATGGTGTACA CTGGGTTCGC CAGGCTACAG GAAAGGGTCT GGAGTGGCTG          60

GGA                                                                      63

(2) INFORMATION FOR SEQ ID NO: 87:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 87:

CTGTTCATTT GCAGATACAG GGAGTTCTTG GCATTTTCCT TGGAGATGGT CAGTCGACTT          60

GTGAAAGGTG TATT                                                           74

(2) INFORMATION FOR SEQ ID NO: 88:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 88:

CTCCCTGTAT CTGCAAATGA ACAGTCTCAG AGCCGGGGAC ACAGCCGTGT ATTACTGTGC          60

CAGAGCCCTC ACC                                                            73

(2) INFORMATION FOR SEQ ID NO: 89:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 89:

GGATCCACTC ACCTGAAGAG ACAGTGACCA TAGTCCCTTG GCCCCAGTAA GCAAA              55

(2) INFORMATION FOR SEQ ID NO: 90:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 90:

GGGTTCGCCA GGCTCCAGGA AAGGGTCTGG AGTGG                                      35

(2) INFORMATION FOR SEQ ID NO: 91:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 91:

TCCTGGAGCC TGGCGAACCC AGTGTACACC                                            30

(2) INFORMATION FOR SEQ ID NO: 92:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 92:

CACAAGTCGA CTGAGCATCA ACAAGGAAAA TGCCAAGAAC TCCCTG                          46

(2) INFORMATION FOR SEQ ID NO: 93:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 93:

CACAAGTCGA CTGACCATCT TCAAGGAAAA TGCCAAGAAC TCCGTTTATC TGCAAATGAA           60

CAGTCTCAGA GC                                                              72

(2) INFORMATION FOR SEQ ID NO: 94:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

-continued (iii) HYPOTHETICAL: NO (iv) ANTI-SENSE: NO (xi) SEQUENCE DESCRIPTION: SEQ ID NO: 94:

TACGCAAACC GCCTCTCCCC GCGCG                                           25

(2) INFORMATION FOR SEQ ID NO: 95:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 95:

CTGAGAGTGC ACCATATGCG GTGTG                                           25

(2) INFORMATION FOR SEQ ID NO: 96:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 96:

AGCGGATAAC AATTTCACAC AGGA                                            24

(2) INFORMATION FOR SEQ ID NO: 97:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 97:

CGCCAGGGTT TTCCCAGTCA CGAC                                            24

(2) INFORMATION FOR SEQ ID NO: 98:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 98:

AATTCTCGAG TCTAGA                                                                         16

(2) INFORMATION FOR SEQ ID NO: 99:

(i) SEQUENCE CHARACTERISTICS:
            (A) LENGTH: 13 amino acids
            (B) TYPE: amino acid
            (C) STRANDEDNESS: not relevant
            (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 99:

Arg Ala Leu Thr Tyr Tyr Asp Tyr Glu Phe Ala Tyr Trp
                  5                   10

(2) INFORMATION FOR SEQ ID NO: 100:

(i) SEQUENCE CHARACTERISTICS:
            (A) LENGTH: 11 amino acids
            (B) TYPE: amino acid
            (C) STRANDEDNESS: not relevant
            (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 100:

Arg Ala Ser Gln Ser Ile Gly Thr Asn Ile His
                  5                   10

(2) INFORMATION FOR SEQ ID NO: 101:

(i) SEQUENCE CHARACTERISTICS:
            (A) LENGTH: 7 amino acids
            (B) TYPE: amino acid
            (C) STRANDEDNESS: not relevant
            (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 101:

Tyr Ala Ser Glu Ser Ile Ser
                  5

(2) INFORMATION FOR SEQ ID NO: 102:

(i) SEQUENCE CHARACTERISTICS:
            (A) LENGTH: 6 amino acids
            (B) TYPE: amino acid
            (C) STRANDEDNESS: not relevant
            (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 102:

Gln Gln Asn Asn Trp Pro
              5

(2) INFORMATION FOR SEQ ID NO: 103:

(i) SEQUENCE CHARACTERISTICS:
        (A) LENGTH: 381 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 103:

| | | | | | |
|---|---|---|---|---|---|
| TACTCCCGGG | GACGAGTCAA | AGAACCGAAG | AACGAAAAGA | CCTAAGGTCG | GAGGTCTTCA | 60 |
| CTGTAGAACG | ACTGAGTCAG | AGGTCAGTAG | GACAGACACTC | AGGTCCTCT | TTCTCAGTCA | 120 |
| AAGAGGACGT | CCCGGTCAGT | CTCATAACCG | TGTTTGTATGT | GACCATAGT | CGTTTCTTGT | 180 |
| TTACCAAGAG | GTTCCGAAGA | GTATTTCATA | CGAAGACTCAG | ATAGAGACC | CTAGGGAAGG | 240 |
| TCCAAATCAC | CGTCACCTAG | TCCCTGTCTA | AAATGAGAATC | GTAGTTGTC | ACACCTCAGA | 300 |
| CTTCTATAAC | GTCTAATAAT | GACAGTTGTT | TTATTATTGAC | CGGTTGGTG | CAAGCCACGA | 360 |
| CCCTGGTTCG | ACCTCGACTT | T | | | | 381 |

(2) INFORMATION FOR SEQ ID NO: 104:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 104:

TACCGACAGA ACCGCGACGA GAAGACGGAC CACTGTAAGG GTTCGACACA GGATAGGGTC         60
GACGTCGACT TCGTCAGTCC TGGACCGGAT CACGTCGGGA GTGTCTCGGA CAGGTAGTGG        120
ACGTGTCAGA GACCAAAGAG TAATTGATTG ATACCACATG TGACCCAAGC GGTCAGAGGT        180
CCTTTCCCAG ACCTCACCGA CCCTCACTAT ACCTCACCAC CTTTGTGTCT GATATTATGT        240
GGAAAGTGTA GGTCTGACTC GTAGTTGTTC CTGTTAAGGT TCTCGGTTCA AAAGAAATTT        300
TACTTGTCAG ACGTTAGATT ACTGTGTCGG TATATAATGA CACGGTCTCG GGAGTGGATG        360
ATACTAATGC TCAAACGAAT GACCCCGGTT CCCTGAGACC AGTGACAGAG ACGT             414

(2) INFORMATION FOR SEQ ID NO: 105:

(i) SEQUENCE CHARACTERISTICS:
        (A) LENGTH: 416 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 105:

| | | | | | |
|---|---|---|---|---|---|
| TTCGAACGGC | GGTGGTACTC | CCGGGGACGA | GTCAAAGAAC | CGAAGAACGA | AAAGACCTAA | 60 |
| GGTCGGAGGT | CTTCACTGTA | GAACGACTGA | GTCAGAGGTC | AGTAGGACAG | ACACTCAGGT | 120 |
| CCTCTTTCTC | AGTCAAAGAG | GACGTCCCGG | TCAGTCTCAT | AACCGTGTTT | GTATGTGACC | 180 |
| ATAGTCGTTT | CTTGTTTACC | AAGAGGTTCC | GAAGAGTATT | TCATACGAAG | ACTCAGATAG | 240 |
| AGACCCTAGG | GAAGGTCCAA | ATCACCGTCA | CCTAGTCCCT | GTCTAAAATG | AGAATCGTAG | 300 |
| TTGTCACACC | TCAGACTTCT | ATAACGTCTA | ATAATGACAG | TTGTTTTATT | ATTGACCGGT | 360 |
| TGGTGCAAGC | CACGACCCTG | GTTCGACCTC | GACTTTGCAC | TCACCTAGGA | AGATCT | 416 |

(2) INFORMATION FOR SEQ ID NO: 106:

(i) SEQUENCE CHARACTERISTICS:
        (A) LENGTH: 442 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 106:

| | | | | | |
|---|---|---|---|---|---|
| TTCGAACGGC | GGTGGTACCG | ACAGAACCCC | GACGAGAAGA | CGGACCACTG | TAAGGGTTCG | 60 |
| ACACAGGATA | GGGTCCACGT | CGACTTCGTC | AGTCCTGGAC | CGGATCACGT | CGGGAGTGTC | 120 |
| TCGGACAGGT | AGTGGACGTG | TCAGAGACCA | AAGAGTAATT | GATTGATACC | ACATGTGACC | 180 |
| CAAGCGGTCA | GAGGTCCTTT | CCCAGACCTC | ACCGACCCTC | ACTATACCTC | ACCACCTTTG | 240 |
| TGTCTGATAT | TATGTGGAAA | GTGTAGGTCT | GACTCGTAGT | TGTTCCTGTT | AAGGTTCTCG | 300 |
| GTTCAAAAGA | AATTTTACTT | GTCAGACGTT | AGATTACTGT | GTCGGTATAT | AATGACACGG | 360 |
| TCTCGGGAGT | GGATGATACT | AATGCTCAAA | CGAATGACCC | CGGTTCCCTG | AGACCAGTGA | 420 |
| CAGAGACGTC | CACTCACCTA | GG | | | | 442 |

(2) INFORMATION FOR SEQ ID NO: 107:

(i) SEQUENCE CHARACTERISTICS:
        (A) LENGTH: 416 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 107:

| | | | | | |
|---|---|---|---|---|---|
| TTCGAACGGC | GGTGGTACCA | TAGGTGTGGA | CTCAAGGAAC | ATAAAAACGA | AAAGACCTAA | 60 |
| GGTCGGAGGT | CTCCACTGTA | GAACGACTGA | GTCAGAGGTC | AGTAGGACAG | ACACTCAGGT | 120 |
| CCTCTTTCTC | AGTCAAAGAG | GACGTCCCGG | TCAGTCTCAT | AACCGTGTTT | GTATGTGACC | 180 |
| ATAGTCGTTT | CTTGTTTACC | AAGAGGTTCC | GAAGAGTATT | TCATACGAAG | ACTCAGATAG | 240 |
| AGACCCTAGG | GAAGGTCCAA | ATCACCGTCA | CCTAGTCCCT | GTCTAAAATG | AGAATCGTAG | 300 |

| | |
|---|---|
| TTGTCACACC TCAGACTTCT ATAACGTCTA ATAATGACAG TTGTTTTATT ATTGACCGGT | 360 |
| TGGTGCAAGC CACGACCCTG GTTCGACCTC GACTTTGCAC TCACCTAGGA AGATCT | 416 |

(2) INFORMATION FOR SEQ ID NO: 108:

(i) SEQUENCE CHARACTERISTICS:
        (A) LENGTH: 416 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 108:

| | |
|---|---|
| TTCGAACGGC GGTGGTACCT TCGGGTCGA GTCGAAGAGA AGGAGAACGA AGAGACCGAG | 60 |
| GGTCTATGGT GGCCTCTTTA GCATGACTGA GTCAGAGGTC GGTGGGACAG AAACTCAGGT | 120 |
| CCTCTTTCTC GGTGGGAGAG GACGTCCCGG TCAGTCTCAT AACCGTGTTT GTATGTGACC | 180 |
| ATAGTCGTTT CTGGACCGGT CCGAGGTTCC GAAGAGTATT TCATACGAAG ACTCAGATAG | 240 |
| AGACCTTAGG GACGGTCCAA ATCACCGTCA CCTAGTCCCT GTCTAAAATG AGAATGGTAG | 300 |
| TCGTCAGACC TCGGACTTCT AAAACGTCAA ATAATGACAG TTGTTTTATT ATTGACCGGT | 360 |
| TGGTGCAAGC CACCTCCCTG GTTCCACCTC TAGTTTGCAC TCACCTAGGA AGATCT | 416 |

(2) INFORMATION FOR SEQ ID NO: 109:

(i) SEQUENCE CHARACTERISTICS:
        (A) LENGTH: 442 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 109:

| | |
|---|---|
| TTCGAACGGC GGTGGTACCT CAAACCCGAC TCGACCGAAA AAGAACACCG ATAAAATTTT | 60 |
| CCACAGGTCA CACTCCACGT CGACCAGCTC AGACCCCCTC CGAACCATGT CGGACCCCCC | 120 |
| AGGGACTCTG AGAGGACACG TCAGAGGCCT AAGAGTAATT GATTGATACC ACATGTGACC | 180 |
| CAAGCGGTCC GATGTCCTTT CCCAGACCTC ACCGACCCTC ACTATACCTC ACCACCTTTG | 240 |
| TGTCTGATAT TATGTGGAAA GTGTTCAGCT GACTGGTAGA GGTTCCTTTT ACGGTTCTTG | 300 |
| AGGGACATAG ACGTTTACTT GTCAGAGTCT CGGCCCCTGT GTCGGCACAT AATGACACGG | 360 |
| TCTCGGGAGT GGATGATACT AATGCTCAAA CGAATGACCC CGGTTCCCTG ATACCAGTGA | 420 |
| CAGAGAAGTC CACTCACCTA GG | 442 |

(2) INFORMATION FOR SEQ ID NO: 110:

(i) SEQUENCE CHARACTERISTICS:
        (A) LENGTH: 20 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 110:

Met Val Ser Thr Pro Gln Phe Leu Val Phe Leu Leu Phe Trp
                 5                  10
Ile Pro Ala Ser Arg Gly
15                  20

(2) INFORMATION FOR SEQ ID NO: 111:

(i) SEQUENCE CHARACTERISTICS:
            (A) LENGTH: 11 amino acids
            (B) TYPE: amino acid
            (C) STRANDEDNESS: not relevant
            (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 111:

Ala Leu Thr Tyr Tyr Asp Tyr Glu Phe Ala Tyr
                 5                  10

(2) INFORMATION FOR SEQ ID NO: 112:

(i) SEQUENCE CHARACTERISTICS:
            (A) LENGTH: 9 amino acids
            (B) TYPE: amino acid
            (C) STRANDEDNESS: not relevant
            (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 112:

Gln Gln Asn Asn Asn Trp Pro Thr Thr
                 5

(2) INFORMATION FOR SEQ ID NO: 113:

(i) SEQUENCE CHARACTERISTICS:
            (A) LENGTH: 107 amino acids
            (B) TYPE: amino acid
            (C) STRANDEDNESS: not relevant
            (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 113:

Glu Ile Val Leu Thr Gln Ser Pro Ala Thr Leu Ser Leu Ser Pro Gly
1               5                  10                  15
Glu Arg Ala Thr Leu Ser Cys Arg Ala Ser Gln Ser Ile Gly Thr Asn
                20                  25                  30
Ile His Trp Tyr Gln Gln Arg Pro Gly Gln Ala Pro Arg Leu Leu Ile
                35                  40                  45

```
Lys Tyr Ala Ser Glu Ser Ile Ser Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Asn Asn Asn Trp Pro Leu
                 85                  90                  95

Thr Phe Gly Gly Gly Thr Lys Val Glu Ile Lys
            100                 105
```

(2) INFORMATION FOR SEQ ID NO: 114:

(i) SEQUENCE CHARACTERISTICS:
        (A) LENGTH: 107 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 114:

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Ile Gly Thr Asn
                 20                  25                  30

Ile His Trp Tyr Gln Gln Arg Pro Gly Gln Ala Pro Arg Leu Leu Ile
             35                  40                  45

Tyr Tyr Ala Ser Glu Ser Ile Ser Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Asn Asn Asn Trp Pro Thr
                 85                  90                  95

Thr Phe Gly Gly Gly Thr Lys Val Glu Ile Lys
            100                 105
```

(2) INFORMATION FOR SEQ ID NO: 115:

(i) SEQUENCE CHARACTERISTICS:
        (A) LENGTH: 119 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 115:

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                 20                  25                  30

Gly Val His Trp Val Arg Gln Ala Thr Gly Lys Gly Leu Glu Trp Val
             35                  40                  45

Ser Val Ile Trp Ser Gly Gly Asn Thr Asp Tyr Asn Thr Pro Phe Thr
 50                  55                  60
```

-continued

```
Ser Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Met Val Thr Val Ser Ser
        115
```

(2) INFORMATION FOR SEQ ID NO: 116:

(i) SEQUENCE CHARACTERISTICS:
        (A) LENGTH: 119 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 116:

```
Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Ser Leu Thr Asn Tyr
                 20                  25                  30

Gly Val His Trp Val Arg Gln Ala Thr Gly Lys Gly Leu Glu Trp Leu
             35                  40                  45

Gly Val Ile Trp Ser Gly Gly Asn Thr Asp Tyr Asn Thr Pro Phe Thr
 50                  55                  60

Ser Arg Leu Thr Ile Ser Lys Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Met Val Thr Val Ser Ser
        115
```

(2) INFORMATION FOR SEQ ID NO: 117:

(i) SEQUENCE CHARACTERISTICS:
        (A) LENGTH: 119 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 117:

```
Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Ser Leu Thr Asn Tyr
                 20                  25                  30

Gly Val His Trp Val Arg Gln Ala Pro Gly Lys Gly Leu Glu Trp Leu
             35                  40                  45
```

-continued

```
Gly Val Ile Trp Ser Gly Gly Asn Thr Asp Tyr Asn Thr Pro Phe Thr
    50                  55                  60

Ser Arg Leu Thr Ile Ser Lys Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Met Val Thr Val Ser Ser
            115
```

(2) INFORMATION FOR SEQ ID NO: 118:

(i) SEQUENCE CHARACTERISTICS:
        (A) LENGTH: 119 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 118:

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Asn Tyr
            20                  25                  30

Gly Val His Trp Val Arg Gln Ala Thr Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Met Val Thr Val Ser Ser
            115
```

(2) INFORMATION FOR SEQ ID NO: 119:

(i) SEQUENCE CHARACTERISTICS:
        (A) LENGTH: 119 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 119:

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Asn Tyr
            20                  25                  30
```

```
-continued

Gly Val His Trp Val Arg Gln Ala Pro Gly Lys Gly Leu Glu Trp Leu
        35              40              45

Gly Val Ile Trp Ser Gly Gly Asn Thr Asp Tyr Asn Thr Pro Phe Thr
        50              55              60

Ser Arg Leu Ser Ile Asn Lys Glu Asn Ala Lys Asn Ser Leu Tyr Leu
65              70              75              80

Gln Met Asn Ser Leu Arg Ala Gly Asp Thr Ala Val Tyr Tyr Cys Ala
                85              90              95

Arg Ala Leu Thr Tyr Tyr Asp Tyr Glu Phe Ala Tyr Trp Gly Gln Gly
                100             105             110

Thr Met Val Thr Val Ser Ser
        115

(2) INFORMATION FOR SEQ ID NO: 120:

(i) SEQUENCE CHARACTERISTICS:
        (A) LENGTH: 119 amino acids
        (B) TYPE: amino acid
        (C) STRANDEDNESS: not relevant
        (D) TOPOLOGY: not relevant (ii) MOLECULE TYPE: peptide (iii) HYPOTHETICAL: NO (v) FRAGMENT TYPE: internal (xi) SEQUENCE DESCRIPTION: SEQ ID NO: 120:

Glu Val Gln Leu Val Glu Ser Gly Gly Gly Leu Val Gln Pro Gly Gly
1               5               10              15

Ser Leu Arg Leu Ser Cys Ala Val Ser Gly Phe Ser Leu Thr Asn Tyr
        20              25              30

Gly Val His Trp Val Arg Gln Ala Thr Gly Lys Gly Leu Glu Trp Leu
        35              40              45

Gly Val Ile Trp Ser Gly Gly Asn Thr Asp Tyr Asn Thr Pro Phe Thr
        50              55              60

Ser Arg Leu Thr Ile Ser Lys Glu Asn Ala Lys Asn Ser Val Tyr Leu
65              70              75              80

Gln Met Asn Ser Leu Arg Ala Gly Asp Thr Ala Val Tyr Tyr Cys Ala
                85              90              95

Arg Ala Leu Thr Tyr Tyr Asp Tyr Glu Phe Ala Tyr Trp Gly Gln Gly
                100             105             110

Thr Met Val Thr Val Ser Ser
        115
```